US009493840B2

(12) United States Patent
Hao et al.

(10) Patent No.: US 9,493,840 B2
(45) Date of Patent: Nov. 15, 2016

(54) CHARACTERIZING MELANOMA

(71) Applicant: University of Louisville Research Foundation, Inc., Louisville, KY (US)

(72) Inventors: Hongying Hao, Louisville, KY (US); Kelly M. McMasters, Crestwood, KY (US); Deyi Xiao, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 14/354,801

(22) PCT Filed: Oct. 26, 2012

(86) PCT No.: PCT/US2012/062181
§ 371 (c)(1),
(2) Date: Apr. 28, 2014

(87) PCT Pub. No.: WO2013/063439
PCT Pub. Date: May 2, 2013

(65) Prior Publication Data
US 2014/0308674 A1 Oct. 16, 2014

Related U.S. Application Data

(60) Provisional application No. 61/552,222, filed on Oct. 27, 2011.

(51) Int. Cl.
*C12Q 1/68* (2006.01)

(52) U.S. Cl.
CPC ....... *C12Q 1/6886* (2013.01); *C12N 2310/141* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2009/0220969 | A1* | 9/2009 | Chiang et al. | 435/6 |
| 2010/0151480 | A1* | 6/2010 | Taylor et al. | 435/6 |
| 2010/0196426 | A1  | 8/2010 | Skog et al. | |
| 2012/0309645 | A1* | 12/2012 | Keller | C12Q 1/6886 506/9 |

FOREIGN PATENT DOCUMENTS

| WO | WO 2009015357 A1 * | 1/2009 | C12Q 1/6809 |
| WO | 2009080437 A1 | 7/2009 | |

OTHER PUBLICATIONS

Taylor et al. (MicroRNA signatures of tumor-derived exosomes as diagnostic biomarkers of ovarian cancer, Gynecol Oncol. Jul. 2008;110(1):13-21).*
Leidinger et al. (High-throughput miRNA profiling of human melanoma blood samples, BMC Cancer. Jun. 7, 2010;10:262. doi: 10.1186/1471-2407-10-262).*
CPMC (Treatment Options for Melanoma, attached, available at http://www.cpmc.org/services/cancer/melanoma/treatment/, Mar. 16, 2011).*
Chan et al. (MicroRNA signatures differentiate melanoma subtypes, Cell Cycle. Jun. 1, 2011;10(11):1845-52. Epub Jun. 1, 2011).*
Philippidou et al. (Signatures of MicroRNAs and Selected MicroRNA Target Genes in Human Melanoma, Cancer Res. May 15, 2010;70(10):4163-73. Epub May 4, 2010).*
Mueller et al. (miRNA Expression Profiling in Melanocytes and Melanoma Cell Lines Reveals miRNAs Associated with Formation and Progression of Malignant Melanoma, J Invest Dermatol. Jul. 2009:129(7)1 740-51. doi: 10.1038/jid.2008.452. Epub Feb. 12, 2009).*
Caramuta et al. (MicroRNA Expression Profiles Associated with Mutational Status and Survival in Malignant Melanoma, J Invest Dermatol. Aug. 2010;130(8):2062-70. doi: 10.1038/jid.2010.63. Epub Apr. 1, 2010).*
Worley et al. (Micro-RNAs associated with metastasis in uveal melanoma identified by multiplexed microarray profiling, Melanoma Res. Jun. 2008;18(3):184-90).*
Segura et al. (Melanoma MicroRNA Signature Predicts Post-Recurrence Survival, Clin Cancer Res. Mar. 1, 2010;16(5):1577-86. doi: 10.1158/1078-0432.CCR-09-2721. Epub Feb. 23, 2010).*
Hood et al. (Exosomes Released by Melanoma Cells Prepare Sentinel Lymph Nodes for Tumor Metastasis, Cancer Res. Jun. 1, 2011;71(11):3792-801. Epub Apr. 8, 2011).*
Palmer et al. (Circulating Serologic and Molecular Biomarkers in Malignant Melanoma, Mayo Clin Proc. Oct. 2011;86(10):981-90).*
Yang et al. (The Roles of Tumor-Derived Exosomes in Cancer Pathogenesis, Clinical and Developmental Immunology, vol. 2011 (2011), Sep. 2011).*
Keller et al. (Body fluid derived exosomes as a novel template for clinical diagnostics, J Transl Med. Jun. 8, 2011;9:86. doi: 10.1186/1479-5876-9-86).*
Chan, Elcie, et al. "MicroRNA Signatures Differentiate Melanoma Subtypes", Cell Cycle, Jun. 1, 2011, vol. 10, No. 11, pp. 1845-1852.
Xiao, Deyi, et al., "Identifying mRNA, MicroRNA and Protein Profiles of Melanoma Exosomes", PLoS One, Oct. 9, 2012, vol. 7, Issue 10, p. e46874.

* cited by examiner

*Primary Examiner* — Aaron Priest
(74) *Attorney, Agent, or Firm* — Stites & Harbison, PLLC; Mandy Wilson Decker; Rachel D. Rutledge

(57) ABSTRACT

The presently disclosed subject matter provides methods of characterizing a melanoma in a subject by measuring amounts of one or more RNAs, miRNAs, and/or polypeptides present in cancer-derived microvesicles isolated from a biological sample from the subject.

4 Claims, 10 Drawing Sheets

CHARACTERIZING MELANOMA

RELATED APPLICATIONS

This application claims priority from U.S. Provisional Application Ser. No. 61/552,222 filed Oct. 27, 2011, the entire disclosure of which is incorporated herein by this reference.

TECHNICAL FIELD

The presently disclosed subject matter relates to methods for characterizing melanoma in a subject. In particular, the presently-disclosed subject matter relates to methods of characterizing a melanoma in a subject by measuring amounts of one or more RNAs and/or proteins present in melanoma-derived microvesicles isolated from a biological sample from the subject.

INTRODUCTION

The identification of cancer biomarkers suitable for the early detection and diagnosis of cancer holds great promise to improve the clinical outcome of subjects. It is especially important for subjects presenting with vague or no symptoms or with rapidly-progressing cancers. Despite considerable effort directed at early detection, few reliable and cost-effective screening tests have been developed that can diagnose cancer at an early stage.

Melanoma is characterized by both a rapidly-rising incidence and a growing lifetime risk. Melanoma treatment is confounded as a rather heterogeneous disease and very wide variability of prognosis, with subsets of patients undergoing unexpectedly poor prognosis. Lack of a precise prognostic tool results in the imprecise application of adjuvant therapy by both under-treatment of those patients who are at high risk of recurrence and over-treatment of those who are actually at low risk.

At present, melanoma prognosis is based on clinicopathologic factors and a population-based staging system. The histological and clinicopathological factors include Breslow thickness, primary tumor ulceration, primary tumor anatomic site, age, gender, number of positive lymph nodes, the largest diameter of metastatic foci in the sentinel lymph node, and distant metastasis. The standard staging system is the American Joint Committee on Cancer (AJCC) TNM classification. It is based on the combination of 3 factors: (1) tumor thickness (T), as described by Breslow thickness (expressed in millimeters); (2) lymph node status (N); and (3) distant metastasis (M). The TNM staging system identifies 4 stages associated with different clinical outcomes. These histological and clinicopathological prognostic factors should only serve as the primary stratification criteria. There, however, still remains significant variability in overall risk assessment for individual patients. Development of more precise biomarkers will not only have clinical utility for individualized treatment, but will have the potential impact to lead to discovery of molecular pathways that may be exploited to a therapeutic advantage.

Early diagnosis and accurate prognostic assessment is central to the process of making rational treatment recommendations for melanoma patients in order to optimize quality of life as well as survival. Unfortunately, barriers exist in this research area. One is that direct access to molecular information contained within the melanoma cells is, by definition, invasive in nature, i.e., occurs through biopsy or surgical removal of melanoma tissue, neither of which is amenable to frequent and longitudinal monitoring. In addition, sampling of melanoma tissue relies on the assumption that the collected fragments are representative of the entire lesion, which is not always the case due to the regional tissue heterogeneity.

As such, there is an unmet need for new biomarkers that individually, or in combination with other biomarkers or diagnostic modalities, deliver the required sensitivity and specificity for early detection and prognosis of melanoma. In particular, simple tests for melanoma biomarkers that can be performed on readily-accessible biological fluids are needed.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes a method for characterizing a melanoma in a subject, which involves isolating melanoma-derived microvesicles from a biological sample of the subject; determining a presence or an amount of one or more microRNAs in the isolated microvesicles; and comparing the presence or the amount of the one or more microRNAs to a reference, wherein the melanoma is characterized based on a measurable difference in the presence or the amount of the one or more microRNAs from the isolated microvesicles as compared to the reference. In some embodiments, a method for characterizing a melanoma in a subject involves determining the presence or amount of one or more microRNAs in a sample containing extracellular melanoma-derived microvesicles from the subject; and comparing the presence or amount of the one or more microRNAs in the sample to a reference, wherein the melanoma is characterized based on a measurable difference in the presence or the amount of the one or more microRNAs in the sample from the subject as compared to the reference. In some embodiments, such methods further include determining a presence or an amount of one or more RNAs and/or polypeptides in the isolated microvesicles. In some embodiments, the melanoma can be characterized based on an expression signature of the one or more RNAs and/or polypeptides. In some embodiments, the melanoma can be characterized based on a measurable difference in the presence or the amount of the one or more RNAs and/or polypeptides from the isolated microvesicles as compared to the reference.

The presently-disclosed subject matter further includes a method for characterizing a melanoma in a subject, which involves isolating melanoma-derived microvesicles from a biological sample of the subject; determining a presence or an amount of one or more melanoma biomarkers in the isolated microvesicles; and comparing the presence or the amount of the one or more melanoma biomarkers to a reference, wherein the melanoma is characterized based on a measurable difference in the presence or the amount of the one or more melanoma biomarkers from the isolated microvesicles as compared to the reference. In some embodiments, a method for characterizing a melanoma in a subject involves determining the presence or amount of one or more melanoma biomarkers in a sample containing extracellular melanoma-derived microvesicles from the subject; and comparing the presence or amount of the one or more melanoma biomarkers in the sample to a reference, wherein the melanoma is characterized based on a measurable difference in the presence or the amount of the one or more melanoma biomarkers in the sample from the subject as compared to the reference.

The presently-disclosed subject matter further includes a method for evaluating treatment efficacy and/or progression of a melanoma in a subject, which includes isolating microvesicles from a biological sample of the subject; determining a presence or an amount of one or more melanoma biomarkers in the isolated microvesicles; and comparing the presence or the amount of the one or more melanoma biomarkers to a reference, wherein the treatment efficacy and/or progression of the melanoma is evaluated based on a measurable difference in the presence or the amount of the one or more melanoma biomarkers as compared to the reference. In some embodiments, a method for assessing a presence or an amount of one or more biomarkers of a melanoma biomarker signature involves isolating microvesicles from a biological sample; and determining the presence or the amount of the one or more melanoma biomarkers in said microvesicles. The microvesicles can be shed from melanoma cells. The biological sample can include a cell culture sample. The method can further involve determining an expression profile of two or more biomarkers. The method can further involve comparing the expression profile with a profile from a selected reference to determine the presence or the amount of two or more biomarkers in said microvesicles. Melanoma biomarkers can be selected from mRNA, miRNA, polypeptide, or combinations thereof.

Various references can be used, to which the presence or amount of a biomarker, e.g., micro RNA, in a sample can be compared. In some embodiments, the reference comprises a level of the one or more microRNAs in one or more samples from one or more individuals without the cancer. In some embodiments, the reference comprises a level of the one or more microRNAs in a sample from the subject taken over a time course. In some embodiments, the reference comprises a sample from the subject collected prior to initiation of treatment for the melanoma and/or onset of the melanoma and the biological sample is collected after initiation of the treatment or onset of the melanoma. In some embodiments, the reference comprises a standard sample. In some embodiments, the reference comprises control data.

In some embodiments, the biological sample comprises milk, blood, serum, plasma, ascites, cyst fluid, pleural fluid, peritoneal fluid, cerebral spinal fluid, tears, urine, saliva, sputum, or combinations thereof.

When determining the presence or amount of the one or more microRNAs in a sample, any method known to one of ordinary skill in the art can be used. In some embodiments, determining the presence or amount of the one or more microRNAs comprises labeling the one or more microRNAs. In some embodiments, determining the presence or amount of the one or more microRNAs comprises capturing the one or more microRNAs with one or more polynucleotide probes that each selectively bind the one or more microRNAs. In some embodiments, determining the presence or amount of the one or more microRNAs comprises using a real-time polymerase chain reaction to quantitate the presence or amount of the one or more microRNAs. In some embodiments, the method is performed in vitro.

When used herein, the term "melanoma biomarker" refers to mRNA, miRNA, polypeptide, or combinations thereof. Specific examples of melanoma biomarkers are set forth herein, including in Tables A-E and in the Tables 1-8 in the Examples.

A non-limiting list of exemplary miRNAs useful to the presently-disclosed subject matter include those set forth in Tables A-E In some embodiments of the presently disclosed subject matter it can be useful to determine the presence of the amount of a melanoma biomarker associated with a particular stage of melanoma. In this regard, in some embodiments the one or more miRNAs is associated with a stage I melanoma, e.g., miRNAs set forth in Table C and/or Table E. In some embodiments of the presently-disclosed methods, the melanoma is characterized as a stage I melanoma. In some embodiments, the melanoma is characterized as not being a stage I melanoma.

In some embodiments the one or more miRNAs is associated with a stage IV melanoma, e.g., miRNAs set forth in Table D and/or Table E. In some embodiments of the presently-disclosed methods, the melanoma is characterized as a stage IV melanoma. In some embodiments, the melanoma is characterized as not being a stage IV melanoma. In some embodiments, the melanoma is characterized as being either a stage I melanoma, a stage IV melanoma, neither a stage I nor a stage IV melanoma, or not a melanoma (e.g., "characterizing a melanoma" as not a melanoma could occur, for example, if the sample is found to correlate with a reference that is a non-cancer control or normal control).

The presently-disclosed subject matter further includes systems and kits, which are useful for practicing embodiments of the methods as described herein. In some embodiments a kit is provided, which is useful for determining a presence or an amount of one or more biomarkers, e.g., micro RNAs, which includes a probe for determining the presence or amount of each of one or more mircroRNAs in a sample. In some embodiment, the probe(s) are polynucleotides. In some embodiments a primer pair is used to determine the amount of the one or more microRNAs. In some embodiments, the probe(s) is provided on a substrate. In some embodiments the kit includes a probe for each of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, or 114 miRNAs. In some embodiments, the kit includes probes and/or primer pairs for one or more miRNAs set forth in Tables A-E. In some embodiments, kits of the presently-disclosed subject matter further include a reference standard sample to obtain a presence or amount of the one or more microRNAs for use as a control to which the sample (e.g., sample from the subject) can be compared. In some embodiments, the systems further include control data of a presence or level of the one or more microRNAs for use as a control to which the sample (e.g., sample from the subject) can be compared. Standard sample or control data can be, for example, for melanoma, for noncancer, or for a particular stage of melanoma, e.g., Stage I, Stage IV. In some embodiments, the systems further include reference data for one or more clinicopathologic features useful for characterizing a cancer-of-interest.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
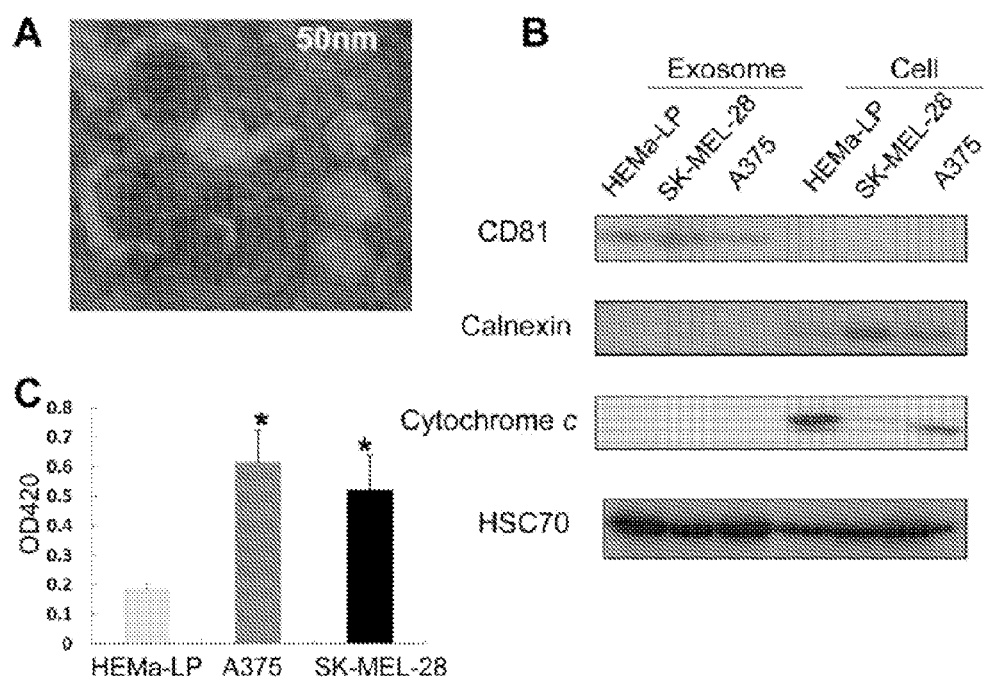
FIG. 1. Identification and characterization of exosomes. Exosomes were isolated using a combination of ultrafiltration and ultracentrifugation. (A). Morphological characterization of exosomes derived from A375 cells by transmission electron microscopy. The image shows small vesicles ranging in size from 50 nm-100 nm in diameter. The scale bar indicates 50 nm. (B). Molecular characterization of exosomes derived from HEMa-LP, SK-MEL-28 and A375 cells by Western blotting. Protein extracts (50 µg) from cells or exosomes were assessed using antibodies against exosomal protein marker (CD81), endoplasmic reticulum marker (Calnexin), and mitochondrial protein marker (cytochrome c). HSC70, a protein expressed both in cells and exosomes, was used as a loading control. (C) Isolated exosomes from an average of 500 ml supernatant of HEMa-LP cells, SK-MEL-28 cells and A375 cells were resuspended in 100 µl of PBS and their quantities were determined using a Nanodrop ND-1000 spectrophotometer reading at OD420.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

In recent years, expression profiling technologies have identified new biomarkers with diagnostic applications. One such biomarker group is a class of small non-coding RNAs, termed microRNAs (miRNAs) (Iorio et al. 2007; De Cecco et al., 2004; Calin & Croce, 2006). MicroRNAs, small (e.g., 17-25 nucleotides in length) non-coding RNAs, suppress the translation of target mRNAs by binding to their 3' untranslated region. Post-transcriptional silencing of target genes by miRNA can occur either by cleavage of homologous mRNA or by specific inhibition of protein synthesis.

All tumors analyzed by miRNA profiling have exhibited significantly distinct miRNA signatures, compared with normal cells from the same tissue (Iorio et al. 2007; Calin & Croce, 2006a; Calin & Croce, 2006b). Lu et al. (2005) performed an analysis of leukemias and solid cancers and determined that miRNA-expression profiles could classify human cancers by developmental lineage and differentiation state. The expressions of individual miRNAs and specific miRNA signatures have now been linked to the diagnosis and prognosis of many human cancers.

Using tissue specimens, Iorio et al. (2007) demonstrated that, in comparison to normal ovary, specific miRNAs were aberrantly expressed in ovarian cancer, with miR-141, miR-200a, miR-200b, and miR-200c being the most significantly overexpressed. They further demonstrated the hypomethylation in ovarian tumors resulted in the up-modulation of miR-21, miR-203, and miR-205, compared with normal ovary. Two of these up-modulated miRNAs, miR-200a and miR-200c, were enhanced in all the three histologic types examined (serous, endometrioid, and clear cell), whereas miR-200b and miR-141 up-modulation was shared by endometrioid and serous histologic types. In general, the miRNA signatures obtained comparing different histologic types of ovarian cancers (serous, endometrioid, clear cell, and mixed) with the normal tissue were overlapping in most cases. Their analysis of ovarian tumors also demonstrated the absence of differentially expressed miRNAs in relation to tumor stage or grade, which could have resulted from their set of samples being primarily derived from advanced stage tumors.

A recently described characteristic of cancer cells is their ability to release or shed intact, vesicular portions of the plasma membrane, known in the art as membrane fragments, membrane vesicles, or microvesicles. Disclosed herein are miRNAs and other biomarkers associated with microvesicles originating from melanoma. The presently disclosed subject matter further discloses that miRNA isolated from such melanoma-derived microvesicles exhibits expression levels in subjects suffering from melanoma that differ (e.g., increased or decreased) from miRNA expression levels measured in subjects free of melanoma. Further, the presently-disclosed subject matter discloses that miRNA isolated from such melanoma-derived microvesicles from subjects with different stages of melanoma exhibit differing expression levels (e.g., increased or decreased in Stage I and Stage IV).

The presently-disclosed subject matter includes methods of characterizing a melanoma in a subject, which make use of melanoma biomarkers. In some embodiments, the melanoma biomarkers are from a microvesicle from the biological sample of the subject. The microvesicle can be derived from a melanoma, e.g., melanoma-derived exosome. As used herein, characterizing is inclusive of providing a diagnosis, prognosis and/or theranosis of the cancer.

The term "melanoma" is taken to mean a tumor arising from the melanocytic system of the skin and other organs. Melanomas include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma subungal melanoma, and superficial spreading melanoma.

"Exosomes" are microvesicles released from a variety of different cells, including cancer cells (i.e., "cancer-derived exosomes" or "melanoma-derived exosomes"). These small vesicles (50-100 nm in diameter) derive from large multivesicular endosomes and are secreted into the extracellular milieu. The precise mechanisms of exosome release/shedding remain unclear; however, this release is an energy-requiring phenomenon, modulated by extracellular signals. They appear to form by invagination and budding from the limiting membrane of late endosomes, resulting in vesicles that contain cytosol and that expose the extracellular domain of membrane-bound cellular proteins on their surface. Using electron microscopy, studies have shown fusion profiles of multivesicular endosomes with the plasma membrane, leading to the secretion of the internal vesicles into the extracellular environment. The rate of exosome release is significantly increased in most neoplastic cells and occurs continuously. Increased release of exosomes and their accumulation appear to be important in the malignant transformation process.

Although extracellular shedding of exosomes occurs in other types of cells, under specific physiological conditions, the accumulation of exosomes from non-neoplastic cells is rarely observed in vivo. In contrast, exosomes released by tumor cells accumulate in biologic fluids, including in sera, ascites, and pleural fluids. Exosome release and its accumulation appear to be important features of the malignant transformation. Shed cancer-derived exosomes do not necessarily mirror the general composition of the plasma membrane of the originating tumor cell, but represent "micromaps," with enhanced expression of tumor antigens.

The release of exosomes appears to be an important feature of intercellular communication. Since released exosomes express molecules with biologic activity (such as Fas ligand, PD-1, MICA/B, mdr1, MMPs, CD44, and autoreactive antigens), the ability of these microvesicles to modulate lymphocyte and monocyte functions have been analyzed in several models. It has been theorized that these released exosomes modulate lymphocyte functions by mimicking "activation induced cell death" (AICD). Lymphoid cells appear to release exosomes following activation and these appear to play an essential role in immunoregulation, by preventing excessive immune responses and the development of autoimmunity. It has been postulated that exosome release by tumor cells is a re-expression of the fetal cell exosomes and that both constitute pathways to circumvent immunosurveillance.

In some embodiments of the presently-disclosed subject matter, the melanoma biomarkers are selected from mRNA, miRNA, protein, or combinations thereof. Such melanoma biomarkers can be from melanoma-derived microvesicles. In some embodiments, the melanoma biomarkers are microRNAs (miRNAs).

MicroRNAs are naturally occurring, small non-coding RNAs that are about 17 to about 25 nucleotide bases (nt) in length in their biologically active form. miRNAs post-transcriptionally regulate gene expression by repressing target mRNA translation. It is thought that miRNAs function as negative regulators, i.e. greater amounts of a specific miRNA will correlate with lower levels of target gene expression.

There are three forms of miRNAs existing in vivo, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nt overhang at the 3' end. The cleavage product, the premature miRNA (pre-miRNA) is about 60 to about 110 nt long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nt in length.

MicroRNAs function by engaging in base pairing (perfect or imperfect) with specific sequences in their target genes' messages (mRNA). The miRNA degrades or represses translation of the mRNA, causing the target genes' expression to be post-transcriptionally down-regulated, repressed, or silenced. In animals, miRNAs do not necessarily have perfect homologies to their target sites, and partial homologies lead to translational repression, whereas in plants, where miRNAs tend to show complete homologies to the target sites, degradation of the message (mRNA) prevails.

MicroRNAs are widely distributed in the genome, dominate gene regulation, and actively participate in many physiological and pathological processes. For example, the regulatory modality of certain miRNAs is found to control cell proliferation, differentiation, and apoptosis; and abnormal miRNA profiles are associated with oncogenesis. Additionally, it is suggested that viral infection causes an increase in miRNAs targeted to silence "pro-cell survival" genes, and a decrease in miRNAs repressing genes associated with apoptosis (programmed cell death), thus tilting the balance towards gaining apoptosis signaling.

Thousands of mRNA are under this selection pressure by hundreds of miRNA species identified so far. This selection process is instrumental in dampening specific groups of gene expressions which, for example, may no longer be needed, to allow cells to channel their physiological program direction to a new pathway of gene expression. The miRNA-dependent dampening of target groups of gene expression is a robust and rapid regulation to allow cells to depart from an old, and transition to a new, program. A typical example of this is demonstrated during embryonic development, when a particular group of cells is directed to become unique specialized cell types such as neurons, cardiomyocytes, muscle, etc.

It is thought that expression levels of roughly a third of human genes are regulated by miRNAs, and that the miRNA regulation of unique gene expressions is linked to the particular signaling pathway for each specific cell type. For example, the apoptosis signaling pathway may be dictated by a group of miRNAs targeted to destabilize pro-survival gene messages, allowing alternative pro-apoptosis genes to gain dominance and thus activate the death program. Another example is the control of cancer growth; a recent discovery has shown that miRNAs may also be essential in preventing cells from becoming neoplastic. For example, two oncogenes, cMyc and cRas, are found to share control by one miRNA species, whose expression is down-regulated in cancer. In other words, lack of this miRNA allows the unchecked expression of cMyc and cRas, thus permitting these two genes to become abundantly present in cancer cells, allowing them to acquire uncontrolled cell proliferating ability, and set the stage for neoplastic growth. Additionally, it has been reported that a miRNA mutation is responsible for a phenotype of muscularity in sheep of Belgian origin, suggesting that mutations associated with genetic disorders could be found in miRNAs, where no evidence of mutations have been found in promoter regions, coding areas, and slicing sites.

It is possible that a coordinated orchestration of multiple pathways serves to control a particular cellular state, wherein certain molecular "hubs" may be involved, which are functionally manipulated by hierarchical orders and redundancy of molecular control. Indeed, dozens of miRNAs may operate to ensure that these "hubs" can exert either major or minor functions in cells, by simply repressing the expression of either themselves or their functional opponents. Thus, one gene product may function as a major "hub" for one signaling pathway in one type of cell, and in another cell type, it may be a minor "hub," or may not be used at all. MicroRNA control of "hub" gene expressions may then be an expedient mechanism to provide such versatility for various molecules to serve as either major or minor "hubs," or not at all, for different types of cellular operational modalities.

Given the role of miRNAs in gene regulation, and in many physiological and pathological processes, information about their interactive modes and their expression patterns is desirable to obtain. Systems and methods of quantitating and identifying which groups of putative miRNAs are in operation in a particular cell type, or in association with a particular process or condition of interest, can provide information useful for understanding how each cellular state evolves and is maintained, and how dysfunctional maintenance is abetted by improper decreases or increases of unique sets of miRNAs to regulate the expression of key genes. Such understanding can prove useful in the diagnosis and characterization of a number of disorders, including cancer.

As potential clinical diagnostic tools miRNAs have been shown to be important and accurate determinants for many if not all cancers. Increasing evidence shows that expression of miRNA genes is deregulated in human cancer. The expression of miRNAs is highly specific for tissues and developmental stages and has allowed recently for molecular classification of tumors. To date, all tumors analyzed by miRNA profiling have shown significantly different miRNA profiles compared with normal cells from the same tissue.

Flow-cytometric miRNA profiling demonstrated that miRNA-expression profiles classify human cancers according to the developmental lineage and differentiation state of the tumors. Specific over- or underexpression has been shown to correlate with particular tumor types. MicroRNA overexpression could result in down-regulation of tumor suppressor genes, whereas their underexpression could lead to oncogene up-regulation. Using large-scale microarray analysis, cancer cells have shown distinct miRNA profiles compared with normal cells with some miRNA genes overexpressed and other miRNAs downregulated in cancer cells versus normal cells. Hierarchical clustering analyses showed that miRNA signatures enable the tumor samples to be grouped on the basis of their tissue of origin. Genome-wide profiling studies have been performed on various cancer types, including CLL, breast cancer, glioblastoma, thyroid papillary carcinoma, hepatocellular carcinoma, ovarian cancer, colon cancer, and endocrine pancreatic tumors. As disclosed herein, methods for making use of miRNA biomarkers for diagnosis and prognosis of melanoma are disclosed.

In some embodiments of the presently disclosed subject matter, a method for characterizing a melanoma in a subject is provided. Characterizing can include providing a diagnosis, prognosis, and/or theragnosis of the cancer. In some embodiments of the presently-disclosed subject matter, a method for evaluation treatment efficacy and/or progression of a melanoma in a subject is provide. In some embodiments of the presently-disclosed subject matter, a method for assessing the presence of one or more melanoma biomarkers, including microRNAs, mRNAs, and/or polypeptides of a melanoma is provided (e.g., a miR signature or miR expression profile; a mRNA signature or mRNA expression profile; a polypeptide signature or a polypeptide expression profile, for example, including HAPLN1, GRP78, syntenin-1, annexin A1, annexin A2, and/or other polypeptides of interest).

In some embodiments, a method for characterizing a melanoma in a subject involves isolating melanoma-derived microvesicles from a biological sample of the subject; determining a presence or an amount of one or more microRNAs in the isolated microvesicles; and comparing the presence or the amount of the one or more microRNAs to a reference, wherein the melanoma is characterized based on a measurable difference in the presence or the amount of the one or more microRNAs from the isolated microvesicles as compared to the reference. In some embodiments, a method for characterizing a melanoma in a subject involves determining the presence or amount of one or more microRNAs in a sample containing extracellular melanoma-derived microvesicles from the subject; and comparing the presence or amount of the one or more microRNAs in the sample to a reference, wherein the melanoma is characterized based on a measurable difference in the presence or the amount of the one or more microRNAs in the sample from the subject as compared to the reference. In some embodiments such methods can further involve determining a presence or an amount of one or more RNAs (e.g., mRNAs) and/or polypeptides in the isolated microvesicles, wherein the melanoma is characterized based on an expression signature of the one or more RNAs and/or polypeptides. In some embodiments the methods can involve determining a presence or an amount of one or more RNAs and/or polypeptides in the isolated microvesicles, wherein the melanoma is characterized based on a measurable difference in the presence or the amount of the one or more RNAs and/or polypeptides from the isolated microvesicles as compared to the reference.

In some embodiments of the presently-disclosed subject matter a method for characterizing a melanoma in a subject can include isolating melanoma-derived microvesicles from a biological sample of the subject; determining a presence or an amount of one or more melanoma biomarkers in the isolated microvesicles; and comparing the presence or the amount of the one or more melanoma biomarkers to a reference, wherein the melanoma is characterized based on a measurable difference in the presence or the amount of the one or more melanoma biomarkers from the isolated microvesicles as compared to the reference. In some embodiments of the presently-disclosed subject matter a method for characterizing a melanoma in a subject involves determining the presence or amount of one or more melanoma biomarkers in a sample containing extracellular melanoma-derived microvesicles from the subject; and comparing the presence or amount of the one or more melanoma biomarkers in the sample to a reference, wherein the melanoma is characterized based on a measurable difference in the presence or the amount of the one or more melanoma biomarkers in the sample from the subject as compared to the reference.

The presently-disclosed subject matter further includes a method for evaluating treatment efficacy and/or progression of a melanoma in a subject, which involves isolating microvesicles from a biological sample of the subject; determining a presence or an amount of one or more melanoma biomarkers in the isolated microvesicles; and comparing the presence or the amount of the one or more melanoma biomarkers to a reference, wherein the treatment efficacy and/or progression of the melanoma is evaluated based on a measurable difference in the presence or the amount of the one or more melanoma biomarkers as compared to the reference. In some embodiments, methods as disclosed herein can further include selecting a treatment or modifying a treatment for the melanoma based on the presence or amount of the one or more micro RNAs determined.

The presently-disclosed subject matter further includes a method for assessing a presence or an amount of one or more biomarkers of a melanoma biomarker signature, which involves isolating microvesicles from a biological sample; and determining the presence or the amount of the one or more melanoma biomarkers in said microvesicles. The microvesicles can be shed from melanoma cells. In some embodiments, the method also involves determining an expression profile of two or more biomarkers. In some embodiments, the method also includes comparing the expression profile with a profile from a selected reference sample to determine the presence or the amount of two or more biomarkers in said microvesicles.

When used herein, the term "melanoma biomarker" refers to mRNA, miRNA, polypeptide, or combinations thereof. Specific examples of melanoma biomarkers are set forth herein, including in Tables A-E and in the Tables 1-8 in the Examples.

A non-limiting list of exemplary miRNAs useful to the presently-disclosed subject matter include those set forth in Tables A-E

TABLE A miRNAs

| | | | | |
|---|---|---|---|---|
| let-7a-5p | miR-146a-5p | miR-2110 | miR-342-5p | miR-515-3p |
| miR-103-3p | miR-1470 | miR-221-5p | miR-345-5p | miR-532-5p |
| miR-106b-3p | miR-150-5p | miR-222-3p | miR-361-3p | miR-548c-3p |
| miR-122-3p | miR-151 | miR-223-3p | miR-361-5p | miR-548o-3p |
| miR-1228-3p | miR-151a-5p | miR-22-3p | miR-382-5p | miR-548u |
| miR-1245a | miR-155-3p | miR-2355-5p | miR-409-3p | miR-556-3p |
| miR-1246 | miR-16-5p | miR-23a-5p | miR-423-3p | miR-570-3p |
| miR-1249 | miR-17-5p | miR-23b-3p | miR-423-5p | miR-574-3p |
| miR-125b-5p | miR-1825 | miR-25-5p | miR-425-3p | miR-584-5p |
| miR-1263 | miR-182-5p | miR-27b-3p | miR-4258 | miR-603 |
| miR-126-3p | miR-183-3p | miR-28-3p | miR-4269 | miR-628 |
| miR-1272 | miR-185-5p | miR-296-5p | miR-4275 | miR-652-3p |
| miR-127-3p | miR-18b-5p | miR-301a-3p | miR-429 | miR-709 |
| miR-1278 | miR-1912 | miR-30c-5p | miR-4299 | miR-744-5p |
| miR-1280 | miR-1913 | miR-3118 | miR-4310 | miR-744-5p |
| miR-1281 | miR-191-5p | miR-3124-5p | miR-432 | miR-877-3p |
| miR-1294 | miR-1953 | miR-3178 | miR-433 | miR-877-5p |
| miR-1301 | miR-195-3p | miR-320d | miR-450b-5p | miR-885-3p |
| miR-1307-3p | miR-196a-3p | miR-324-5p | miR-451 | miR-92a-3p |
| miR-132-3p | miR-197-3p | miR-331-3p | miR-4794 | miR-93-3p |
| miR-139-5p | miR-199a-3p | miR-339-3p | miR-486-3p | miR-940 |
| miR-140-3p | miR-200b-5p | miR-339-5p | miR-500a-3p | miR-99a-5p |
| miR-145-5p | miR-2110 | miR-342-3p | miR-501-3p | |

TABLE B

Stage I and IV Common miRNAs

| | | | | |
|---|---|---|---|---|
| let-7a-5p | miR-151a-5p | miR-17-5p | miR-27b-3p | miR-744-5p |
| miR-126-3p | miR-155-3p | miR-23b-3p | miR-342-3p | miR-940 |
| miR-151* | | | | |

TABLE C

Stage I vs. Normal

| | | | | |
|---|---|---|---|---|
| let-7a-5p | miR-145-5p | miR-200b-5p | miR-342-3p | miR-501-3p |
| miR-103-3p | miR-146a-5p | miR-2110 | miR-342-5p | miR-515-3p |
| miR-106b-3p | miR-150-5p | miR-22-3p | miR-345-5p | miR-548o-3p |
| miR-1228-3p | miR-151 | miR-222-3p | miR-361-3p | miR-548u |
| miR-1245a | miR-151a-5p | miR-223-3p | miR-361-5p | miR-574-3p |
| miR-1246 | miR-155-3p | miR-23a-5p | miR-382-5p | miR-584-5p |
| miR-1249 | miR-16-5p | miR-23b-3p | miR-409-3p | miR-603 |
| miR-125b-5p | miR-17-5p | miR-27b-3p | miR-423-3p | miR-628 |
| miR-126-3p | miR-182-5p | miR-28-3p | miR-423-5p | miR-652-3p |
| miR-1263 | miR-1825 | miR-296-5p | miR-425-3p | miR-744-5p |
| miR-127-3p | miR-185-5p | miR-301a-3p | miR-4258 | miR-877-3p |
| miR-1278 | miR-18b-5p | miR-30c-5p | miR-429 | miR-885-3p |
| miR-1280 | miR-191-5p | miR-3118 | miR-4299 | miR-92a-3p |
| miR-1281 | miR-1912 | miR-3178 | miR-432 | miR-93-3p |
| miR-1301 | miR-1913 | miR-320d | miR-433 | miR-940 |
| miR-1307-3p | miR-195-3p | miR-324-5p | miR-451 | miR-99a-5p |
| miR-132-3p | miR-1953 | miR-331-3p | miR-4794 | |
| miR-139-5p | miR-197-3p | miR-339-3p | miR-486-3p | |
| miR-140-3p | miR-199a-3p | miR-339-5p | miR-500a-3p | |

TABLE D

Stage IV vs. Normal

| | | | | |
|---|---|---|---|---|
| let-7a-5p | miR-155-3p | miR-222-3p | miR-4258 | miR-570-3p |
| miR-103-3p | miR-16-5p | miR-2355-5p | miR-4269 | miR-603 |
| miR-1228-3p | miR-17-5p | miR-23b-3p | miR-4275 | miR-628 |
| miR-126-3p | miR-1825 | miR-25-5p | miR-4299 | miR-709 |
| miR-1263 | miR-183-3p | miR-27b-3p | miR-4310 | miR-744-5p |
| miR-1272 | miR-185-5p | miR-3124-5p | miR-450b-5p | miR-885-3p |
| miR-1278 | miR-191-5p | miR-324-5p | miR-451 | miR-92a-3p |
| miR-1280 | miR-195-3p | miR-331-3p | miR-486-3p | miR-940 |
| miR-1294 | miR-200b-5p | miR-342-3p | miR-548c-3p | |
| miR-140-3p | miR-2110 | miR-361-5p | miR-548o-3p | |
| miR-151 | miR-22-3p | miR-423-3p | miR-548u | |
| miR-151a-5p | miR-221-5p | miR-423-5p | miR-556-3p | |

TABLE E

Stage IV vs. Stage I

| | | | | |
|---|---|---|---|---|
| let-7a-5p | miR-1470 | miR-1913 | miR-3124-5p | miR-4794 |
| miR-106b-3p | miR-150-5p | miR-196a-3p | miR-339-5p | miR-532-5p |
| miR-122-3p | miR-151 | miR-2355-5p | miR-342-3p | miR-744-5p |
| miR-1246 | miR-151a-5p | miR-23a-5p | miR-345-5p | miR-877-5p |
| miR-126-3p | miR-155-3p | miR-23b-3p | miR-382-5p | miR-940 |
| miR-1301 | miR-17-5p | miR-27b-3p | miR-409-3p | |
| miR-132-3p | miR-182-5p | miR-28-3p | miR-425-3p | |
| miR-139-5p | miR-183-3p | miR-296-5p | miR-4269 | |
| miR-146a-5p | miR-18b-5p | miR-3118 | miR-432 | |

In some embodiments of the presently disclosed subject matter it can be useful to determine the presence of the amount of a melanoma biomarker associated with a particular stage of melanoma. In this regard, in some embodiments the one or more miRNAs is associated with a stage I melanoma, e.g., miRNAs set forth in Table C and/or Table E. In some embodiments of the presently-disclosed methods, the melanoma is characterized as a stage I melanoma. In some embodiments, the melanoma is characterized as not being a stage I melanoma.

In some embodiments the one or more miRNAs is associated with a stage IV melanoma, e.g., miRNAs set forth in Table D and/or Table E. In some embodiments of the presently-disclosed methods, the melanoma is characterized as a stage IV melanoma. In some embodiments, the melanoma is characterized as not being a stage IV melanoma. In some embodiments, the melanoma is characterized as being either a stage I melanoma, a stage IV melanoma, neither a stage I nor a stage IV melanoma, or not a melanoma (e.g., "characterizing a melanoma" as not a melanoma could occur, for example, if the sample is found to correlate with a reference that is a non-cancer control or normal control).

In some embodiments, methods of the presently-disclosed subject matter include determining an expression profile or a signature of two or more melanoma biomarkers. In some embodiments, the methods can include comparing the expression profile with a profile from a selected reference to determine the presence or the amount of two or more melanoma biomarkers in said microvesicles.

A biomarker expression profile or biomarker signature for a sample can include information about the identities of biomarkers contained in the sample, quantitative levels of biomarkers contained in the sample, and/or changes in quantitative levels of biomarkers relative to another sample or control. For example, a biomarker signature or profile for a sample can include information about the identities, quantitative levels, and/or changes in quantitative levels of biomarkers from an cancer-derived extracellular microvesicles from a biological sample of particular subject. In some embodiments, a biomarker signature or profile relates to information about two or more biomarkers in a sample (e.g., biomarker signature or profile consisting of 2 biomarkers). In some embodiments, a biomarker signature or profile consists of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, or 114 biomarkers.

In some embodiments, the one or more biomarkers of the expression profile or signature include one or more biomarkers set forth in Tables 1-8. In some embodiments, the one or more biomarkers of the expression profile or signature include one or more microRNAs selected from those set forth in Tables A-E.

As will be recognized by one or ordinary skill in the art, in some embodiments, methods of the presently-disclosed subject matter can be performed in vitro.

The term "biological sample" as used herein refers to a sample that comprises a biomolecule and/or is derived from a subject. Representative biomolecules include, but are not limited to total DNA, RNA, miRNA, mRNA, and polypeptides. The biological sample can be used for the detection of the presence and/or expression level of a miRNA of interest associated with melanoma-derived microvesicles. Any cell, group of cells, cell fragment, or cell product can be used with the methods of the presently claimed subject matter, although biological fluids and organs that would be predicted to contain cancer-derived microvesicles exhibiting differential expression of miRNAs as compared to a reference are best suited. In some embodiments, the biological sample is a relatively easily obtained biological sample, such as for example blood or a component thereof. In some embodiments, the biological sample comprises milk, blood, serum, plasma, ascites, cyst fluid, pleural fluid, peritoneal fluid, cerebral spinal fluid, tears, urine, saliva, sputum, or combinations thereof. In some embodiments, the sample includes a cell culture sample.

In some embodiments, size exclusion chromatography is used to isolate the cancer-derived microvesicles. Size exclusion chromatography techniques are known in the art. In some embodiments, a void volume fraction is isolated and comprises the microvesicles of interest. Further, in some embodiments, the melanoma-derived microvesicles can be further isolated after chromatographic separation by centrifugation techniques (of one or more chromatography fractions), as is generally known in the art. In some embodiments, for example, density gradient centrifugation can be used to further isolate the microvesicles. Still further, in some embodiments, it can be desirable to further separate the melanoma-derived isolated microvesicles from microvesicles of other origin. For example, the cancer-derived microvesicles can be separated from non-cancer-derived microvesicles by immunosorbent capture using an anti-cancer antigen antibody. In some embodiments, the microvesicles can be isolated from the biological sample, for example, using methods as described in U.S. Patent Application Publication Nos. 2010/0298151 and 2010-0151480.

The terms "diagnosing" and "diagnosis" as used herein refer to methods by which the skilled artisan can estimate and even determine whether or not a subject is suffering from a given disease or condition. The skilled artisan often makes a diagnosis on the basis of one or more diagnostic indicators, such as for example a biomarker (e.g., an miRNA expression level), the amount (including presence or absence) of which is indicative of the presence, severity, or absence of the condition.

Along with diagnosis, clinical cancer prognosis is also an area of great concern and interest. It is important to know the aggressiveness of the cancer cells and the likelihood of tumor recurrence in order to plan the most effective therapy. Some types of melanoma, for example, are managed by several alternative strategies. Current treatment decisions for individual cancer subjects can be based on (1) the number of lymph nodes involved with disease, (2) cancer marker(s) status, (3) the size of the primary tumor, and (4) stage of disease at diagnosis. However, even with these factors, accurate prediction of the course of disease for all melanoma subjects is not possible. If a more accurate prognosis can be made, appropriate therapy, and in some instances less severe therapy, for the patient can be chosen. Measurement of melanoma-derived microvesicle miRNA levels disclosed herein can be useful in order to categorize subjects according to advancement of melanoma who will benefit from particular therapies and differentiate from other subjects where alternative or additional therapies can be more appropriate. Treatment related diagnostics are sometimes referred to as "theranosics." As such, in some embodiments of the presently disclosed subject matter, a method for characterizing a melanoma in a subject is provided. In some embodiments, the method comprises providing a biological sample from a subject; isolating melanoma-derived microvesicles comprising micro-RNAs (miRNAs) from the biological sample; determining an amount of one or more of the miRNAs; and comparing the amount of the one or more miRNAs to a reference. In such embodiments, the melanoma can be characterized based on a measurable difference in the amount of the one or more miRNAs from the melanoma-derived microvesicles as compared to a reference. In some embodiments, characterizing the melanoma comprises determining a type, a grade, and/or a stage of the cancer.

"Making a diagnosis" or "diagnosing," as used herein, is further inclusive of making a prognosis, which can provide for predicting a clinical outcome (with or without medical treatment), selecting an appropriate treatment (or whether treatment would be effective), or monitoring a current treatment and potentially changing the treatment, based on the measure of melanoma-derived microvesicle diagnostic miRNA levels. Diagnostic testing that involves treatment, such as treatment monitoring or decision making can be referred to as "theranosis." Further, in some embodiments of the presently disclosed subject matter, multiple determination of amounts of one or more miRNAs over time can be made to facilitate diagnosis (including prognosis), evaluating treatment efficacy, and/or progression of a cancer. A temporal change in one or more melanoma-derived microvesicle miRNA levels (i.e., miRNA amounts in a biological sample) can be used to predict a clinical outcome, monitor the progression of the melanoma, and/or efficacy of administered melanoma therapies. In such an embodiment for example, one could observe a decrease in the amount of particular miRNAs in a biological sample over time during the course of a therapy, thereby indicating effectiveness of treatment.

The presently disclosed subject matter further provides in some embodiments a method for theranostic testing, such as evaluating treatment efficacy and/or progression of a melanoma in a subject. In some embodiments, the method comprises providing a series of biological samples over a time period from the subject; isolating melanoma-derived microvesicles comprising miRNAs from the series of biological samples; determining an amount of one or more of the miRNAs in each of the biological samples from the series; and determining any measurable change in the amounts of the one or more miRNAs in each of the biological samples from the series to thereby evaluate treatment efficacy and/or progression of the melanoma in the subject. Any changes in the amounts of measured miRNAs over the time period can be used to predict clinical outcome, determine whether to initiate or continue the therapy for the cancer, and whether a current therapy is effectively treating the cancer. For example, a first time point can be selected prior to initiation of a treatment and a second time point can be selected at some time after initiation of the treatment. miRNA levels can be measured in each of the samples taken from different time points and qualitative and/or quantitative differences noted. A change in the amounts of one or more of the measured miRNA levels from the first and second samples can be correlated with prognosis, theranosis, determining treatment efficacy, and/or progression of the disease in the subject.

The terms "correlated" and "correlating," as used herein in reference to the use of diagnostic and prognostic miRNA levels associated with melanoma, refers to comparing the presence or quantity of the miRNA levels in a subject to a reference. By way of nonlimiting examples, a reference can be the presence or quantity of the miRNAs in subjects known to suffer from a melanoma, or in subjects known to be free of the melanoma, i.e. "normal subjects" or "control subjects." For example, a level of one or more miRNAs in a biological sample can be compared to a miRNA level for each of the specific miRNAs tested and determined to be correlated with a melanoma. The sample's one or more miRNA levels is said to have been correlated with a diagnosis; that is, the skilled artisan can use the miRNA level(s) to determine whether the subject suffers from the melanoma and respond accordingly. Alternatively, the sample's miRNA level(s) can be compared to control miRNA level(s) known to be associated with a good outcome (e.g., the absence of cancer), such as an average level found in a population of normal subjects.

In some embodiments of the presently disclosed subject matter, the reference includes a level of the one or more microRNAs in one or more samples from one or more individuals without the cancer. In some embodiments, the reference includes a level of the one or more microRNAs in a sample from the subject taken over a time course. In some embodiments, the reference includes a sample from the subject collected prior to initiation of treatment for the melanoma and/or onset of the melanoma and the biological sample is collected after initiation of the treatment or onset of the melanoma. In some embodiments the reference includes a standard sample. In some embodiments the reference includes control data.

In certain embodiments, a miRNA level is correlated to a melanoma by merely its presence or absence. In other embodiments, a threshold level of the miRNA can be established, and the level of the miRNA in a subject sample can simply be compared to the threshold level.

As noted, in some embodiments, multiple determinations of one or more miRNA levels can be made, and a temporal change in the levels can be used to characterize the melanoma. For example, specific miRNA level(s) can be determined at an initial time, and again at a second time. In such embodiments, an increase in the miRNA level(s) from the initial time to the second time can be diagnostic of the melanoma, or a given prognosis. Likewise, a decrease in the miRNA level(s) from the initial time to the second time can be indicative of the melanoma, or a given prognosis. Furthermore, the degree of change of one or more miRNA level(s) can be related to the severity of the cancer and/or timeline of disease progression and future adverse events.

The skilled artisan will understand that, while in certain embodiments comparative measurements can be made of the same miRNA level(s) at multiple time points, one can also measure given miRNA level(s) at one time point, and second miRNA level(s) at a second time point, and a comparison of these levels can provide diagnostic information.

The phrase "determining the prognosis" as used herein refers to methods by which the skilled artisan can predict the course or outcome of a condition in a subject. The term "prognosis" can refer to the ability to predict the course or outcome of a condition with up to 100% accuracy, or predict that a given course or outcome is more or less likely to occur based on the presence, absence or levels of a biomarker. The term "prognosis" can also refer to an increased probability that a certain course or outcome will occur; that is, that a course or outcome is more likely to occur in a subject exhibiting a given condition, when compared to those individuals not exhibiting the condition. For example, in individuals not exhibiting the condition (e.g., not expressing the miRNA level(s) or expressing miRNA level(s) at a reduced level), the chance of a given outcome (e.g., suffering from cancer) may be very low (e.g., <1%), or even absent. In contrast, in individuals exhibiting the condition (e.g., expressing the miRNA level(s) or expressing miRNA level(s) at a level greatly increased over a control level), the chance of a given outcome (e.g., suffering from a form/stage of cancer) may be higher. In certain embodiments, a prognosis is about a 5% chance of a given expected outcome, about a 7% chance, about a 10% chance, about a 12% chance, about a 15% chance, about a 20% chance, about a 25% chance, about a 30% chance, about a 40% chance, about a 50% chance, about a 60% chance, about a 75% chance, about a 90% chance, or about a 95% chance.

The skilled artisan will understand that associating a prognostic indicator with a predisposition to an adverse outcome can be performed using statistical analysis. For example, miRNA level(s) (e.g., quantity of one or more miRNAs in a sample) of greater or less than a control level in some embodiments can signal that a subject is more likely to suffer from a cancer than subjects with a level less than or equal to the control level, as determined by a level of statistical significance. Additionally, a change in miRNA level(s) from baseline levels can be reflective of subject prognosis, and the degree of change in marker level can be related to the severity of adverse events. Statistical significance is often determined by comparing two or more populations, and determining a confidence interval and/or a p value. See, e.g., Dowdy and Wearden, Statistics for Research, John Wiley & Sons, New York, 1983, incorporated herein by reference in its entirety. Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001. When performing multiple statistical tests, e.g., determining differential expression of a panel of miRNA levels, p values can be corrected for multiple comparisons using techniques known in the art.

In other embodiments, a threshold degree of change in the level of a prognostic or diagnostic miRNA level(s) can be established, and the degree of change in the level of the indicator in a biological sample can simply be compared to the threshold degree of change in the level. A preferred threshold change in the level for miRNA level(s) of the presently disclosed subject matter is about 5%, about 10%, about 15%, about 20%, about 25%, about 30%, about 50%, about 60%, about 75%, about 100%, or about 150%. In yet other embodiments, a "nomogram" can be established, by which a level of a prognostic or diagnostic indicator can be directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

The identity and relative quantity of miRNAs in a sample can be used to provide miRNA profiles for a particular sample. An miRNA profile for a sample can include information about the identities of miRNAs contained in the sample, quantitative levels of miRNAs contained in the sample, and/or changes in quantitative levels of miRNAs relative to another sample. For example, an miRNA profile for a sample can include information about the identities, quantitative levels, and/or changes in quantitative levels of miRNAs associated with a melanoma.

Further with respect to the diagnostic methods of the presently disclosed subject matter, a preferred subject is a vertebrate subject. A preferred vertebrate is warm-blooded; a preferred warm-blooded vertebrate is a mammal. A mammal is most preferably a human. As used herein, the term "subject" includes both human and animal subjects. Thus, veterinary therapeutic uses are provided in accordance with the presently disclosed subject matter.

As such, the presently disclosed subject matter provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

As noted hereinabove, the presently disclosed subject matter provides for the determination of the amount of melanoma-derived microvesicle miRNAs correlated with melanoma within biological fluids of a subject, and in particular, from serological samples from a subject, such as for example blood. This provides the advantage of biological samples for testing that are easily acquired from the subject. The amount of one or more miRNAs of interest in the biologic sample can then be determined using any of a number of methodologies generally known in the art and compared to miRNA control levels.

The "amount" of one or more miRNAs determined refers to a qualitative (e.g., present or not in the measured sample) and/or quantitative (e.g., how much is present) measurement of the one or more miRNAs. The "control level" is an amount (including the qualitative presence or absence) or range of amounts of one or more miRNAs found in a comparable biological sample in subjects not suffering from cancer. As one non-limiting example of calculating the control level, the amount of one or more miRNAs of interest present in a normal biological sample (e.g., blood) can be calculated and extrapolated for whole subjects.

An exemplary methodology for measuring miRNA levels from microvesicles in a biological sample is microarray technique, which is a powerful tool applied in gene expression studies. The technique provides many polynucleotides with known sequence information as probes to find and hybridize with the complementary strands in a sample to thereby capture the complementary strands by selective binding.

The term "selective binding" as used herein refers to a measure of the capacity of a probe to hybridize to a target polynucleotide with specificity. Thus, the probe comprises a polynucleotide sequence that is complementary, or essentially complementary, to at least a portion of the target polynucleotide sequence. Nucleic acid sequences which are "complementary" are those which are base-pairing according to the standard Watson-Crick complementarity rules. As used herein, the term "complementary sequences" means nucleic acid sequences which are substantially complementary, as can be assessed by the same nucleotide comparison set forth above, or as defined as being capable of hybridizing to the nucleic acid segment in question under relatively stringent conditions such as those described herein. A particular example of a contemplated complementary nucleic acid segment is an antisense oligonucleotide. With regard to probes disclosed herein having binding affinity to miRNAs, the probe can be 100% complementary with the target polynucleotide sequence. However, the probe need not necessarily be completely complementary to the target polynucleotide along the entire length of the target polynucleotide so long as the probe can bind the target polynucleotide with specificity and capture it from the sample.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by the skilled artisan. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. Determining appropriate hybridization conditions to identify and/or isolate sequences containing high levels of homology is well known in the art. For the purposes of specifying conditions of high stringency, preferred conditions are a salt concentration of about 200 mM and a temperature of about 45° C.

Data mining work is completed by bioinformatics, including scanning chips, signal acquisition, image processing, normalization, statistic treatment and data comparison as well as pathway analysis. As such, microarray can profile hundreds and thousands of polynucleotides simultaneously with high throughput performance. Microarray profiling analysis of mRNA expression has successfully provided valuable data for gene expression studies in basic research. And the technique has been further put into practice in the pharmaceutical industry and in clinical diagnosis. With increasing amounts of miRNA data becoming available, and with accumulating evidence of the importance of miRNA in gene regulation, microarray becomes a useful technique for high through-put miRNA studies.

The analysis of miRNA correlated with melanoma can be carried out separately or simultaneously with multiple polynucleotide probes within one test sample. For example, several probes can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in miRNA levels over time. Increases or decreases in miRNA levels, as well as the absence of change in levels, can provide useful information about the disease status.

In some embodiments, a panel consisting of polynucleotide probes that selectively bind melanoma-derived microvesicle miRNAs correlated with one or more cancers can be constructed to provide relevant information related to the diagnosis or prognosis of cancer and management of subjects with cancer. Such a panel can be constructed, for example, using 1, 2, 3, 4, 5, 6, 7, 8, 9, 10, 15, 20, 30, 40, 50, 75, 100, 150, 200, 250, 300, 400, 500, or 1,000 individual polynucleotide probes. In some cases, a panel comprises more than 1,000 individual polynucleotide probes. The analysis of a single probe or subsets of probes comprising a larger panel of probes could be carried out by one skilled in the art to optimize clinical sensitivity or specificity in various clinical settings. These include, but are not limited to ambulatory, urgent care, critical care, intensive care, monitoring unit, in-subject, out-subject, physician office, medical clinic, and health screening settings. Furthermore, one skilled in the art can use a single probe or a subset of additional probes comprising a larger panel of probes in combination with an adjustment of the diagnostic threshold in each of the aforementioned settings to optimize clinical sensitivity and specificity. The clinical sensitivity of an assay is defined as the percentage of those with the disease that the assay correctly predicts, and the specificity of an assay is defined as the percentage of those without the disease that the assay correctly predicts.

In some embodiments, determining the amount of the one or more miRNAs comprises labeling the one or more miRNAs. The labeled miRNAs can then be captured with one or more polynucleotide probes that each selectively bind the one or more miRNAs.

As used herein, the terms "label" and "labeled" refer to the attachment of a moiety, capable of detection by spectroscopic, radiologic, or other methods, to a probe molecule. Thus, the terms "label" or "labeled" refer to incorporation or attachment, optionally covalently or non-covalently, of a detectable marker into/onto a molecule, such as a polynucleotide. Various methods of labeling polypeptides are known in the art and can be used. Examples of labels for polynucleotides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for antibodies, metal binding domains, epitope tags, etc.). In some embodiments, labels are attached by spacer arms of various lengths to reduce potential steric hindrance.

The analysis of miRNA levels using polynucleotide probes can be carried out in a variety of physical formats as well. For example, the use of microtiter plates or automation can be used to facilitate the processing of large numbers of test samples. Alternatively, single sample formats could be developed to facilitate immediate treatment and diagnosis in a timely fashion.

In some embodiments, the plurality of polynucleotide probes are each bound to a substrate. In some embodiments, the substrate comprises a plurality of addresses. Each address can be associated with at least one of the polynucleotide probes of the array. An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" miRNA can be referenced as a moiety in a mobile phase (typically fluid), to be detected by probes ("target probes") which are bound to the substrate at the various regions.

Biopolymer arrays (e.g., polynucleotide microarrays) can be fabricated by depositing previously obtained biopolymers (such as from synthesis or natural sources) onto a substrate, or by in situ synthesis methods. Methods of depositing obtained biopolymers include, but are not limited to, loading then touching a pin or capillary to a surface, such as described in U.S. Pat. No. 5,807,522 or deposition by firing from a pulse jet such as an inkjet head, such as described in PCT publications WO 95/25116 and WO 98/41531, and elsewhere. The in situ fabrication methods include those described in U.S. Pat. No. 5,449,754 for synthesizing peptide arrays, and in U.S. Pat. No. 6,180,351 and WO 98/41531 and the references cited therein for polynucleotides, and may also use pulse jets for depositing reagents. Further details of fabricating biopolymer arrays by depositing either previously obtained biopolymers or by the in situ method are disclosed in U.S. Pat. Nos. 6,242,266, 6,232,072, 6,180,351, and 6,171,797. In fabricating arrays by depositing previously obtained biopolymers or by in situ methods, typically each region on the substrate surface on which an array will be or has been formed ("array regions") is completely exposed to one or more reagents. For example, in either method the array regions will often be exposed to one or more reagents to form a suitable layer on the surface that binds to both the substrate and biopolymer or biomonomer. In in situ fabrication the array regions will also typically be exposed to the oxidizing, deblocking, and optional capping reagents. Similarly, particularly in fabrication by depositing previously obtained biopolymers, it can be desirable to expose the array regions to a suitable blocking reagent to block locations on the surface at which there are no features from non-specifically binding to target.

Determining the amount of melanoma-derived microvesicle miRNAs can alternatively, or in addition to microarray analysis, comprise using real-time polymerase chain reaction (PCR). Real-time PCR (RT-PCR) can provide accurate and rapid data as to presence and amount of miRNAs present in a sample.

The presently-disclosed subject matter is inclusive of uses of reagents as described herein and reagents known to those of ordinary skill in the art to carry out the methods as disclosed herein and described in the claims. The presently-disclosed subject matter further includes kits that include reagents as described herein and reagents known to those of ordinary skill in the art to carry out the methods as disclosed herein and described in the claims.

The presently-disclosed subject matter further includes systems and kits, which are useful for practicing embodiments of the methods as described herein. In some embodiments a kit is provided, which is useful for determining a presence or an amount of one or more biomarkers, e.g., micro RNAs, which includes a probe for determining the presence or amount of each of one or more mircroRNAs in a sample. In some embodiment, the probe(s) are polynucleotides. In some embodiments a primer pair is used to determine the amount of the one or more microRNAs. In some embodiments, the probe(s) is provided on a substrate. In some embodiments the kit includes a probe for each of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, or 114 miRNAs. In some embodiments, the kit includes probes and/or primer pairs for one or more miRNAs set forth in Tables A-E.

In some embodiments, kits of the presently-disclosed subject matter further include a reference standard sample to obtain a presence or amount of the one or more microRNAs for use as a control to which the sample (e.g., sample from the subject) can be compared. In some embodiments, the systems further include control data of a presence or level of the one or more microRNAs for use as a control to which the sample (e.g., sample from the subject) can be compared. Standard sample or control data can be, for example, for melanoma, for noncancer, or for a particular stage of melanoma, e.g., Stage I, Stage IV. In some embodiments, the systems further include reference data for one or more clinicopathologic features useful for characterizing a cancer-of-interest.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

In certain instances, microRNAs (miRNAs) disclosed herein are identified with reference to names assigned by the miRBase Registry (available at www.mirbase.org). The sequences and other information regarding the identified miRNAs as set forth in the miRBase Registry are expressly incorporated by reference as are equivalent and related miRNAs present in the miRBase Registry or other public databases. Also expressly incorporated herein by reference are all annotations present in the miRBase Registry associated with the miRNAs disclosed herein. Unless otherwise indicated or apparent, the references to the miRBase Registry are references to the most recent version of the database as of the filing date of this Application (i.e., mirBase 19, released Aug. 1, 2012).

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Materials and Methods

Cell Lines and Culture Reagents.
Two normal human epidermal melanocytes, HEMa-LP and NHEM-c cells, were purchased from Life Technologies (Carlsbad, Calif.) and PromoCell (Heidelberg, Germany), respectively. The human malignant melanoma cell lines A375 and SK-MEL-28 were purchased from American Type Culture Collection (Rockville, Md.). A375 cells and SK-MEL-28 cells were maintained in Dulbecco's Modified Eagle Medium (DMEM) and a minimal essential medium (α-MEM), respectively, supplemented with 10% exosome-depleted fetal bovine serum (FBS) and penicillin (100 U/mL)/streptomycin (100 µg/mL). FBS was depleted of exosomes by ultracentrifugation at 100,000×g for 16 h at 4° C. HEMa-LP cells and NHEM-c cells were cultured in Medium 254 supplemented with Human Melanocyte Growth Supplement-2 (HMGS-2) and Melanocyte Growth Medium M2 supplemented with Supplement Mix (Promo-Cell, Heidelberg, Germany), respectively, in a 5% $CO_2$ incubator at 37° C. All other cell culture reagents were obtained from Life Technologies.

Preparation and Isolation of Exosomes.

Exosomes were purified from cell culture supernatants by a combination of ultrafiltration and ultracentrifugation. A three-step approach was used to isolate exosomes from culture media as described previously [19]. Initially, culture medium was collected and centrifuged at 400×g for 10 min to remove whole cells. The supernatant was then centrifuged at 15,000×g for 20 min to remove debris. The resulting cell-free medium was concentrated by ultrafiltration using Amicon stirred cell Model 8200 with a molecular weight cutoff membrane of 500,000 Daltons (Millipore, Billerica, Mass.). This concentrated material was then ultracentrifuged at 100,000×g for 90 min at 4° C. to generate an exosome pellet. The pellet was resuspended and washed twice with PBS. Exosome quantity was determined using Nanodrop ND-1000 spectrophotometer at 420 nm (Thermo Fisher Scientific, Pittsburgh, Pa.).

Another exosome isolation method was performed using Exoquick-TC precipitation (System Biosciences, Mountain View, Calif.). Briefly, 10 ml of cell culture supernatant was centrifuged at 3000×g for 30 minutes to remove cells and cell debris. The supernatant was mixed with 2 ml of Exoquick-TC and refrigerated overnight. The Exoquick-TC/Cell supernatant mixture was then centrifuged at 10,000×g for 30 minutes at 4° C. The exosome pellet was washed twice with PBS and resuspended in serum-free media to be used in migration/invasion assay.

Transmission Electron Microscopy (TEM).

Isolated exosomes were collected, washed in cacodylate buffer, and fixed in 4% glutaraldehyde (Polysciences, Warrington, Pa.) in cacodylate buffer overnight at 4° C., dehydrated with graded alcohol steps, and flat embedded in LX-112 epoxy resin (Ladd Industries, Burlington, Vt.). Sections were cut with an ultramicrotome. Mounted sections (70-80 nm) were collected on copper grids, stained with saturated solution of uranyl acetate, and submitted for imaging using a Philips CM12 Transmission Electron Microscope operating at 60 kV [20].

RNA Isolation and Microarray Analysis.

Total RNA from cells and exosomes were isolated using mirVana total RNA isolation kit (Life Technologies) according to the manufacturer's guidelines. This protocol effectively recovers both mRNA and miRNA. RNA was quantified using Nanodrop ND-1000 (Thermo Fisher Scientific). The integrity of these total RNAs was assessed using Agilent 2100 Bioanalyzer (Agilent, Santa Clara, Calif.). Total high-quality RNA was converted to cDNA, transcribed and labeled, and then hybridized to human HG-U133 plus 2 arrays (Affymetrix, Santa Clara, Calif.) then scanned according to the standard protocol recommended by Affymetrix. The miRNA array profiling was performed by using the Affymetrix GeneChip miRNA Array 1.0. Two different RNA preparations from two cell lines and their exosomes were used, except that only one RNA preparation was used for HEMa-LP exosome miRNA array. Due to the limited number of passages (approximately 10), adequate exosomal RNA and proteins from HEMa-LP cells for multiple analyses was not available.

mRNA and miRNA Expression Validation by Semi-Quantitative Reverse Transcription-PCR.

Briefly, total RNA (100 ng) from cell lines and exosomes were reverse transcribed with the SuperScript III First-Strand Synthesis System for RT-PCR (Life Technologies) for gene expression validation. mRNA primers were purchased from Life Technologies. For miRNA expression validation, total RNA (10 ng) was converted into cDNA using specific miRNA primers and miRNA reverse transcription kit (Life Technologies) and further amplified according to the manufacturer's protocol. Quantitative RT-PCR reactions were completed on a 7500 Fast Real Time PCR system (Life Technologies). The relative quantity of the target mRNA or miRNA was normalized to an endogenous gene (GAPDH) or control miRNA and, relative to a calibrator; then fold changes were calculated with the $2^{-\Delta\Delta Ct}$ method. Samples were run in triplicate and at least 3 independent experiments were performed. Data are presented as mean±SD. A p value of <0.05 was considered to be statistically significant.

miRNA Target Gene Prediction.

TargetScanHuman 6.0 (www.targetscan.org) was used for miRNA target gene predictions. Predicted target genes in combination with miRNA and whole-genome microarray data were used to visualize possible biological miRNA/mRNA interactions correlating to melanoma development and/or progression.

Proteomic Analysis.

The concentration of the exosome protein extracts were determined by protein assay and analyzed by 2-D DIGE (two-dimensional difference in gel electrophoresis). Equal amounts of protein extracts (25 µg) from A375 and HEMa-LP exosomes were labeled with Cy5 and Cy3, respectively. The two labeled exosome samples were simultaneous separated on a single 2-D gel, using isoelectric focusing (IEF) in the first dimension and SDS polyacrylamide gel electrophoresis (SDS-PAGE) in the second dimension. The gel was scanned using a Typhoon image scanner. ImageQuant software was used to generate the single and overlay images. Quantitative and comparative analysis of all spots was performed by using DeCyder "in-gel" analysis software to generate protein expression ratios between A375 and HEMa-LP exosomes. Protein spots of interest were picked from the 2-D gel and identified by mass spectrometry. Protein identification was based on peptide fingerprint mass mapping (using MS spectra) and peptide fragmentation mapping (using MS/MS spectra). Combined MS and MS/MS spectra were then submitted for database search using GPS Explore software to identify proteins from primary sequence database.

Confocal Microscopy.

HEMa-LP cells and isolated A375 exosomes were labeled using the green lipophilic fluorescent dye PKH67, and the red lipophilic fluorescent dye PKH26 (Sigma-Alrich, St Louis, Mo.), respectively, according to the manufacturer's instructions. Briefly, HEMa-LP cells were trypsinized and resuspended. The quantities of exosomes were determined by optical density at 420 nm. The re-suspended cells and exosomes were incubated with the two different dyes respectively for 5 min at room temperature. The reaction was stopped by addition of 2 ml FBS. After washing with PBS, the green PKH67-labelled HEMa-LP cells were seeded on cover slips in 24-well plates and incubated with the red PKH26-labelled exosomes for 24 h. HEMa-LP cells were then washed with PBS and mounted with Mowiol (Calbiochem, La Jolla, Calif.). The scans were performed in a sequential mode to avoid channel crosstalk. Pictures were taken on an Olympus Fluoview 500 confocal microscope.

MTT Assay.

MTT (3-[4,5-Dimethylthiazol-2-Yl]-2,5-Diphenyltetrazolium Bromide) assay was conducted to assess cell survival and growth. HEMa-LP and NHEM-c cells were incubated with 20 μl of A375 or SK-MEL-28 melanoma exosomes (OD420=0.01), or cycloheximide (0.1 μg/ml) for 5 days of treatment. MTT assay was conducted as described previously [21].

In Vitro Migration/Invasion Assay.

BD BioCoat Matrigel control chambers and invasion chambers (BD Biosciences) were used according to the manufacturer's protocol, and as previously described [22, 23]. Briefly, 28,000 HEMa-LP cells or NHEM-c cells were plated in each chamber in a 24-well plate. The next day, isolated A375 exosomes or SK-MEL-28 exosomes were resuspended in serum-free media. 100 ul of exosomes with an OD420 reading of 0.01 were added to each well. Serum-free media was used as a control. After 5 days of incubation, non-invading cells were removed from the upper surface of the membrane. Migrating cells in the control chamber and invading cells in the invasion chamber were fixed and stained with Diff-Quick (Siemens Healthcare Diagnostics, Deerfield, Ill.) and then counted in each insert. Protein synthesis inhibitor cycloheximide {3-[2-(3,5-dimethyl-2-oxocyclohexyl)-2-hydroxyethyl]glutarimide} was purchased from Sigma Chemical Co. (St. Louis, Mo.). Cycloheximide was prepared fresh in 0.9% saline, and used at a final concentration of 0.1 μg/ml where indicated. DNase, RNase A, and Protease K were purchased from Sigma Chemical Co. (St. Louis, Mo.), and used at final concentration of 100 μg/ml. Each invasion assay experiment was performed in triplicate and repeated three times. Results are presented as percent invasion, which was calculated by dividing the number of the cells that invaded through the invasion chamber by the number of the cells that migrated through the control chamber and multiplying by 100.

To check mRNA expression by RT-PCR analysis after invasion assay, HEMa-LP cells were plated in a 6-well plate. The next day, 500 μl of isolated A375 exosomes or SK-MEL-28 exosomes with an OD420 reading of 0.01 were added to each well. 500 μl of serum-free media was used as a control. After 5 days of incubation, culture media was removed. Cellular RNA was isolated as described in mRNA expression validation by semi-quantitative reverse transcription-PCR.

Statistical Analysis.

The mRNA and miRNA array data were analyzed using Partek Genomics Suite v6.5 (Partek Inc., St. Louis, Mo.). A False Discovery Rate (FDR) corrected p-value of <0.01 and a fold change of >2 were defined as upregulation, while a FDR corrected p-value of <0.01 and a fold change of <−2 were defined as downregulation unless otherwise stated. Ingenuity Pathway Analysis (IPA) software (Ingenuity Systems, Redwood City, Calif.) was used for gene network and pathway analysis. The statistical score of a pathway is defined as −log (P value) from Fisher's exact test analysis.

For other experiments, data from three independent experiments were analyzed by Student t-test and are given as mean±SD. A p-value of <0.05 was considered to be statistically significant.

Accession Number.

The mRNA array and miRNA array data have been deposited in NCBI's Gene Expression Omnibus (GEO, http://www.ncbi.nlm.nih.gov/geo) and are accessible through GEO series accession number GSE 35389.

Results

Identification and Characterization of Exosomes.

Exosomes are released into a variety of body fluids in vivo, and into the media of cultured cells in vitro, in order to execute important biological functions. Previously, the most common method for isolating exosomes from cultured cell-media was differential centrifugation, which is very time-consuming and labor-intensive. The present inventors used a technique combining ultrafiltration and ultracentrifugation, which allows for efficient exosome isolation from cultured media [19]. Purified vesicles from A375 cell culture supernatants were first examined by transmission electron microscopy (TEM), which showed that the isolated membrane-bound round-shaped vesicles ranged in size from about 50-100 nm in diameter (FIG. 1A). This size range is consistent with exosomes. Western blot revealed that the exosome-specific protein, CD81, was enriched in all exosome samples but not in cell lysates—confirming these vesicles as exosomes (FIG. 1B). Calnexin, an endoplasmic reticulum protein, was detectable in whole cell lysates but absent in the exosomes, indicating that the exosome preparations were not contaminated with other vesicles (FIG. 1B). A similar result was obtained for a mitochondrial protein, cytochrome c (FIG. 1B), demonstrating that there was no contamination with apoptotic vesicles. HSC70, which has been shown to be present in both cells and exosomes [24] was used as a loading control (FIG. 1B). These results confirmed the identification and characterization of isolated vesicles as exosomes. Exosome yields from A375 and SK-MEL-28 melanoma cells were much greater than those from HEMa-LP normal melanocytes as shown by OD420 values (FIG. 1C), confirming enhanced exosome secretion from tumor cells.

Differential mRNA Expression Profiles of Exosomes Versus Cell Lines, and A375 Versus HEMa-LP Exosomes.

Figure 2A:
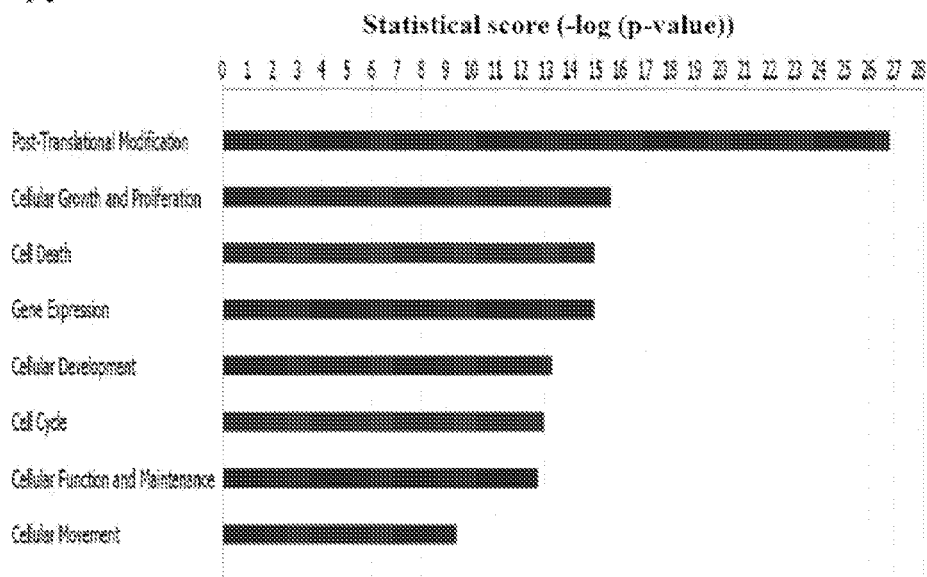
FIG. 2. Differentially expressed mRNAs in exosomes versus cell lines, and A375 versus HEMa-LP exosomes by Ingenuity Analysis. Biological functions (A) and pathway analysis (B) of differentially expressed mRNAs in HEMa-LP exosomes versus HEMa-LP cells. Biological functions (C) and pathway analysis (D) of differentially expressed mRNAs in A375 exosomes versus A375 cells. Biological functions (E) and pathway analysis (F) of differentially expressed mRNAs in A375 exosomes versus HEMa-LP exosomes.
Figure 2B:
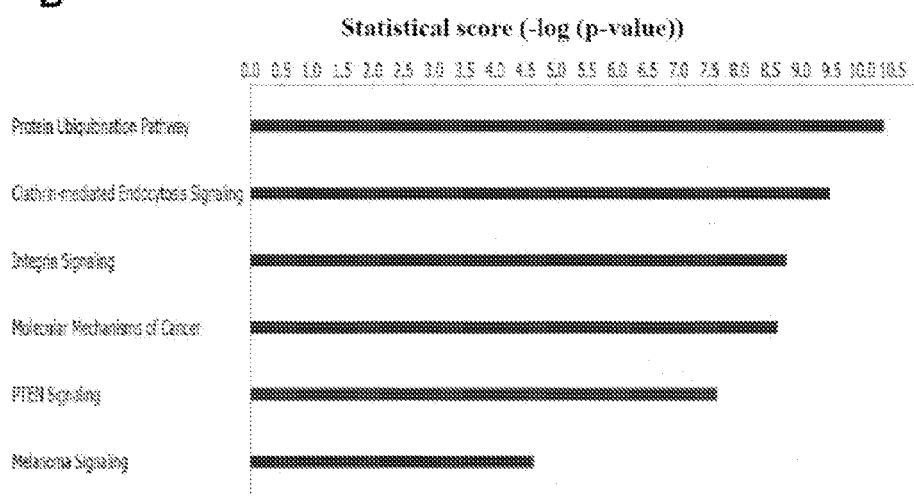
Figure 3:
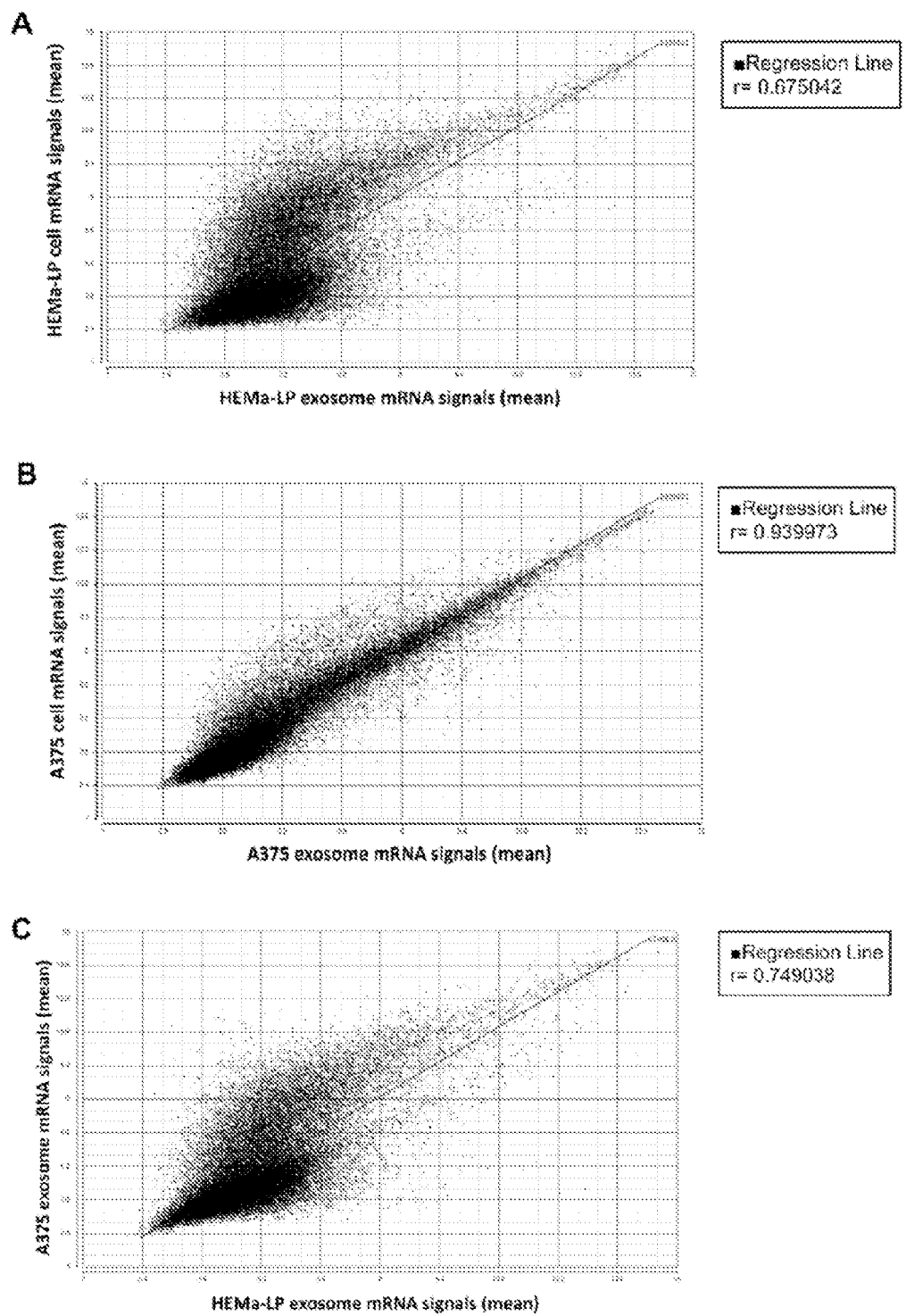
FIG. 3. Correlation of mRNA signals between cells and exosomes. Affymetrix HU133 plus 2 arrays were used to analyze mRNA signals in HEMa-LP melanocytes and A375 melanoma cells as well as exosomes from the two cell lines. Two different arrays were performed from two different RNA preparations for each sample. Scatterplots of mRNA signals in HEMa-LP exosomes compared with their originating cells (A), A375 exosomes compared with their originating cells (B), and A375 exosomes compared with HEMa-LP exosomes (C). Regression analysis showed that mRNA signals in cells versus exosomes were correlated. mRNA signals in A375 exosomes were also correlated with those in HEMa-LP exosomes.

Whole-genome mRNA arrays were performed to identify genes differentially expressed in exosomes versus cell lines, and A375 exosomes versus HEMa-LP exosomes. Using Partek Genomics Suite for differential gene expression analysis, the present inventors identified 14,784 probe sets that were upregulated, and 13,671 probe sets that were downregulated in normal human melanocyte HEMa-LP exosomes versus HEMa-LP cells. In order to further analyze the genes that were differentially expressed in HEMa-LP exosomes versus HEMa-LP cells, the present inventors restricted the criteria of upregulation as a FDR corrected p-value of <0.01 and a fold change of >5, and downregulation as a FDR corrected p-value of <0.01 and a fold change of <−5. This resulted in 913 probe sets (813 genes) that were upregulated and 4921 probe sets (3642 genes) downregulated in HEMa-LP exosomes versus HEMa-LP cells (Table 3). Some of the genes in the array have multiple probe sets representing various splice forms that may have differential biological function. Ingenuity pathway analysis showed involvement of differentially expressed genes in post-translational modification (506 molecules), cellular growth and proliferation (975 molecules), cell death (778 molecules), gene expression (744 molecules), and cellular development (816 molecules) (FIG. 2A). Those differentially expressed genes were involved in the protein ubiquitination (statistical score=10.359), clathrin-mediated endocytosis signaling (statistical score=9.472), and integrin signaling pathways (statistical score=8.758) (FIG. 2B). Regression analysis showed that mRNA signals between HEMa-LP cells and exosomes were correlated (r=0.675) (FIG. 3A).

Figure 2C:
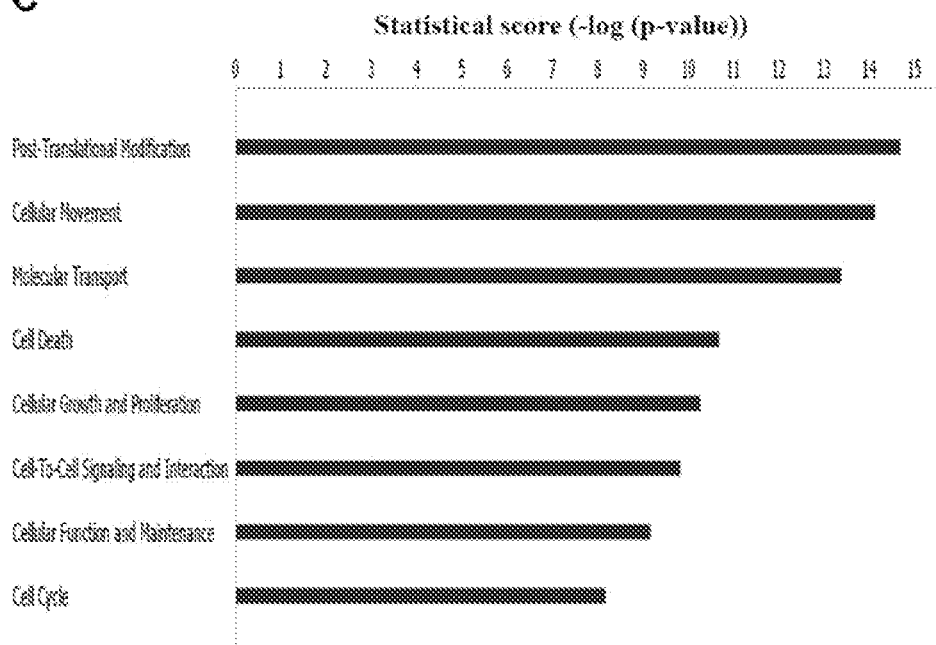
Figure 2D:
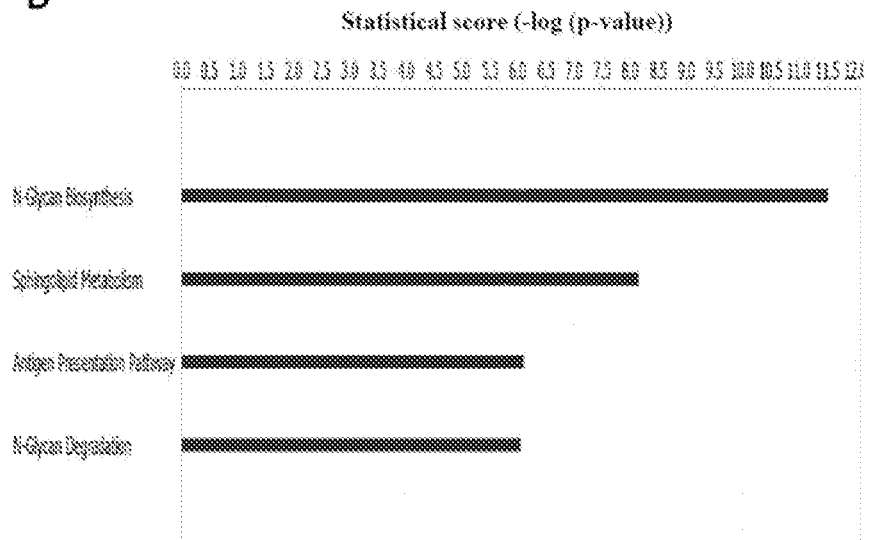

The present inventors also identified 842 probe sets (721 genes) upregulated and 3,678 probe sets (2564 genes) downregulated in human melanoma cell line A375 exosomes versus A375 cells. The complete list of upregulated and downregulated genes (and their different splice-forms of probe sets) is given in Table 4. Ingenuity analysis showed involvement of those differentially expressed genes functioning in post-translational modification (344 molecules), cellular movement (402 molecules), molecular transport (396 molecules), cell death (556 molecules) and cellular growth and proliferation (698 molecules) (FIG. 2C). Those differentially expressed genes were involved in N-glycan biosynthesis (statistical score=11.505), sphingolipid metabolism (statistical score=8.148), and antigen presentation pathways (statistical score=6.1) (FIG. 2D). Among these identified pathways, the N-glycan pathway has been shown to be involved in tyrosinase and melanin synthesis in melanoma cells as well as melanoma cell metastasis [25, 26]. Sphingolipid has been involved in a lipogenic pathway to boost Akt signaling [27]. A strong correlation of mRNA signals between A375 cells and exosomes was found (r=0.93997) (FIG. 3B). These results show that normal cell-derived exosomes and melanoma cell-derived exosomes contain many mRNAs related to cellular growth and proliferation, cellular movement, and gene expression. Even though some of the mRNAs are differentially expressed between the cells and the cell-derived exosomes, the exosomal mRNAs have a strong correlation with the cellular mRNAs. This correlation was stronger between A375 melanoma cells and exosomes. These data suggest that exosome mRNA signatures may reveal information about gene signatures from within their parent cells.

Figure 2E:
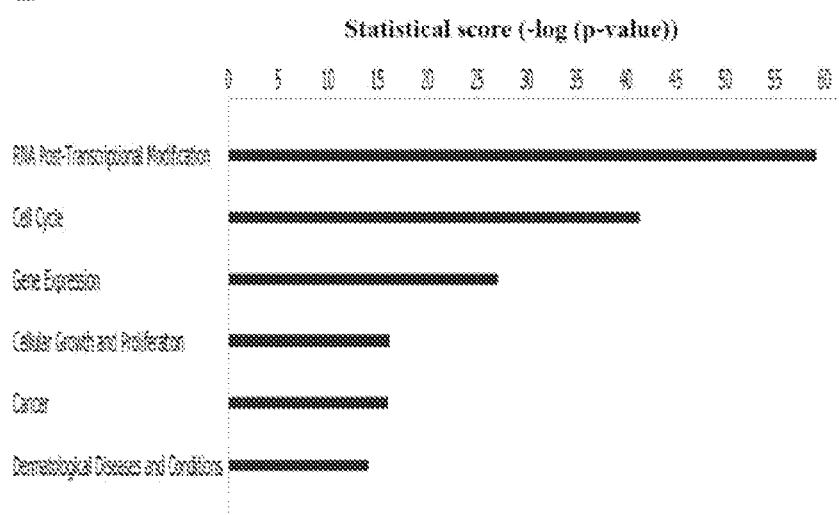
Figure 2F:
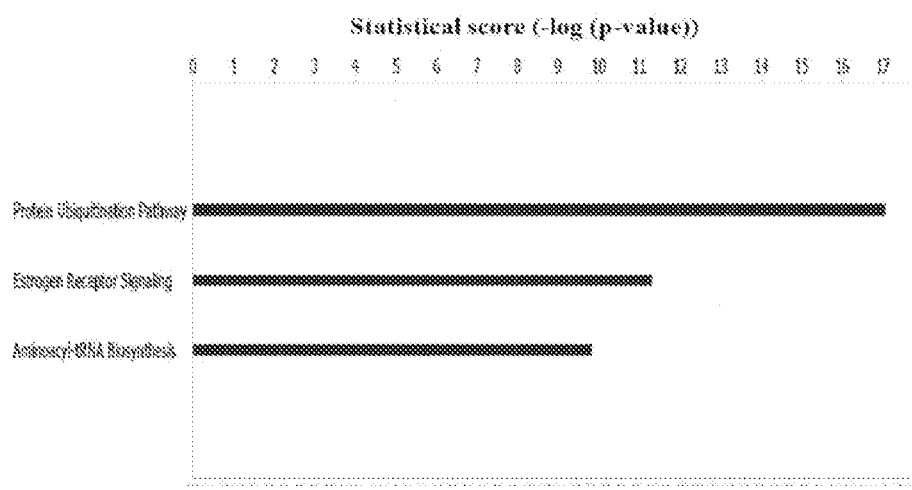

After the present inventors compared the gene signatures between cells and exosomes, the present inventors were interested in exploring the difference between mRNA expression profiles of melanoma cell-derived exosomes and normal melanocyte-derived exosomes. For these analyses the present inventors once again defined upregulation as a FDR corrected p-value of <0.01 and a fold change of >5, and downregulation as a FDR corrected p-value of <0.01 and a fold change of <−5. The present inventors identified 3553 probe sets (2813 genes) upregulated, and 379 probe sets (333 genes) downregulated in A375 exosomes versus HEMa-LP exosomes (Table 5). Ingenuity analysis showed that 945 differentially expressed genes are associated with cancer, and 364 differentially expressed genes are associated with dermatological diseases and conditions (FIG. 2E). Among the upregulated genes were TOP1 (DNA topoisomerase I), which is associated with advanced melanomas and poor prognosis [28]. Among the downregulated genes were TYRP1 (tyrosinase-related protein 1) and ABCB5 (ATP-binding cassette, sub-family B, member 5), both of which are related to melanoma progression and initiation [29-31]. Ingenuity analysis showed that those differentially expressed genes function in RNA post-transcriptional modification (198 molecules), cell cycle (481 molecules), gene expression (656 molecules), and cellular growth and proliferation (756 molecules) (FIG. 2E). Those differentially expressed genes are involved in protein ubiquitination (statistical score=17.066), estrogen receptor signaling (statistical score=11.313), and aminoacyl-tRNA biosynthesis (statistical score=9.84) pathways, all of which have been shown to be involved in melanoma growth and progression (FIG. 2F). Even though regression analysis showed that mRNA signals in A375 exosomes were somewhat correlated with those in HEMa-LP exosomes (r=0.749038) (FIG. 3C), these results suggest that melanoma cell-derived exosomes have distinct mRNA profiles that differ from those of normal melanocyte-derived exosomes. Those differentially expressed mRNAs in melanoma exosomes may play important roles in tumor initiation, progression, and metastasis. This also implies that those exosomal mRNAs may serve as biomarkers to differentiate melanoma from normal melanocytes.

Differential miRNA Expression Profiles of Exosomes Versus Cell Lines and A375 Versus HEMa-LP Exosomes.

Figure 4A:
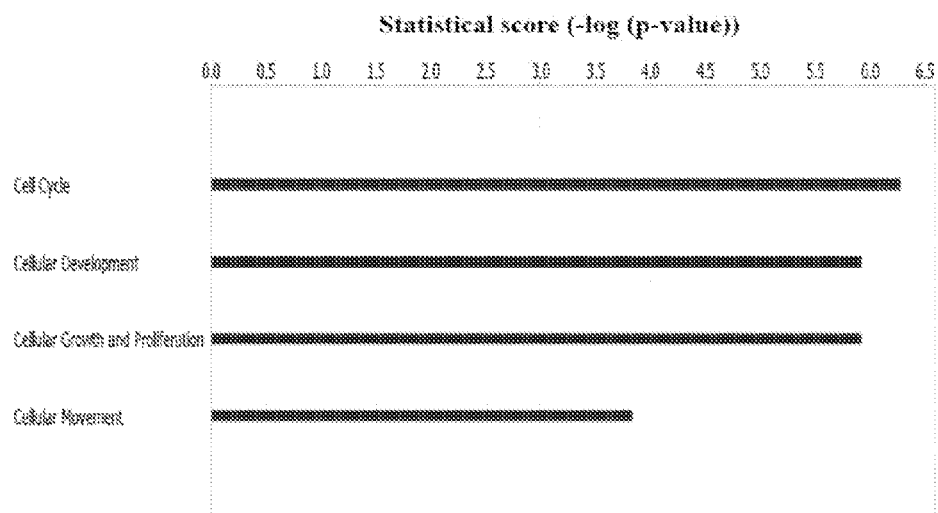
FIG. 4. Differentially expressed miRNAs in exosomes versus cell lines, and A375 versus HEMa-LP exosomes by Ingenuity Analysis. Biological functions of differentially expressed miRNAs in HEMa-LP exosomes versus HEMa-LP cells (A) and in A375 exosomes versus HEMa-LP exosomes (B).
Figure 5:
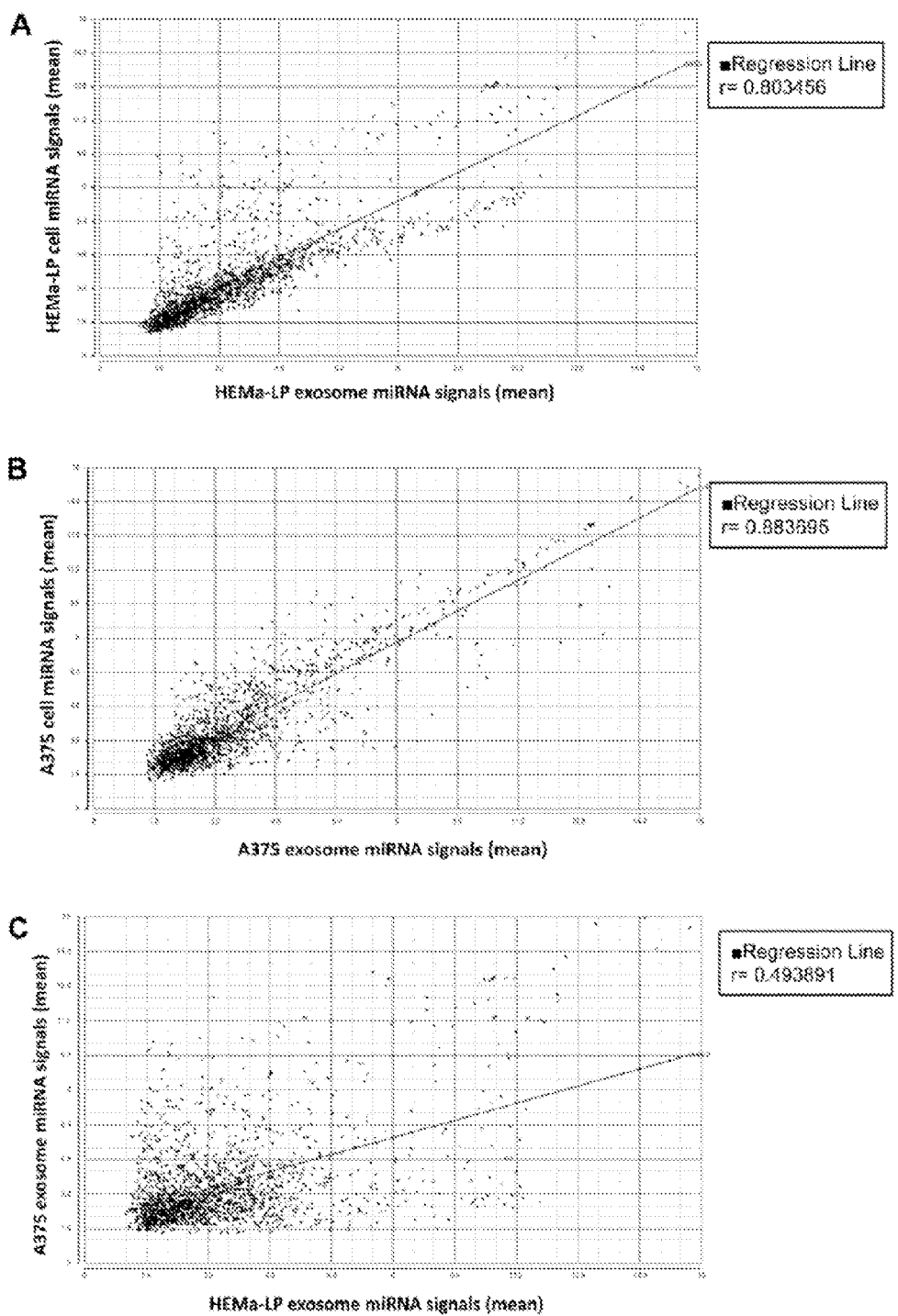
FIG. 5. Correlation of miRNA signals between cells and exosomes. Affymetrix miRNA 1.0 arrays were used to analyze miRNA signals in HEMa-LP melanocytes and A375 melanoma cells, as well as exosomes from the two cell lines. Two different arrays were performed from two different RNA preparations for each sample, except for only one RNA preparation for HEMa-LP exosomal miRNA array. Scatterplots of miRNA signals in HEMa-LP exosomes compared with their originating cells (A), A375 exosomes compared with their originating cells (B), and A375 exosomes compared with HEMa-LP exosomes (C). Regression analysis showed that miRNA signals in HEMa-LP cells versus HEMa-LP exosomes, and A375 cells versus A375 exosomes were correlated, whereas miRNA signals in A375 exosomes versus HEMa-LP exosomes were not well correlated.

Emerging evidence shows that exosome miRNA have close relationships with tumorigenesis and metastasis [1, 9, 18]. In order to shed light on exosome miRNA profiles, miRNA arrays were performed to identify differentially expressed miRNAs in exosomes versus cell lines and A375 exosomes versus HEMa-LP exosomes. Using Partek Genomics Suite, the present inventors identified 14 miRNAs upregulated and 75 miRNAs downregulated in HEMa-LP exosomes versus HEMa-LP cells (Table 6). Ingenuity analysis showed the involvement of those differentially expressed miRNAs functioning in cell cycle (9 miRNAs), cellular development (12 miRNAs), cellular growth and proliferation (16 miRNAs), and cellular movement (11 miRNAs) (FIG. 4A). A strong correlation of miRNA signals between HEMa-LP cells and exosomes was found (r=0.803456) (FIG. 5A).

The present inventors also identified 28 miRNAs upregulated and 5 miRNAs downregulated in A375 exosomes versus A375 cells (Table 7). Ingenuity analysis showed many of these differentially expressed miRNA are associated with cancer (hsa-miR-1228, -125b-5p/-125a-5p/-125b, -195/-16-2, -339-5p/-3586-5p, -346, -494, -638). Other differentially expressed miRNAs also function in cellular growth and proliferation (hsa-miR-125 and hsa-miR-346), cellular development (hsa-miR-346), cellular movement (hsa-miR-125), and cell death (has-miR-193). A strong correlation of miRNA signals between A375 cells and exosomes was found (r=0.883695) (FIG. 5B). The miRNA signatures of HEMa-LP exosomes versus HEMa-LP cells, and A375 exosomes versus A375 cells correlate well with those of their respective mRNA profiles. These results suggested that strong correlations of miRNA profiles exist between cells and cell-derived exosomes, suggesting that the exosomal miRNome largely represents miRNA signatures within their originating cells. Exosomes also contain many miRNAs that are linked with cellular growth and proliferation, cellular development and cellular movement.

Figure 4B:
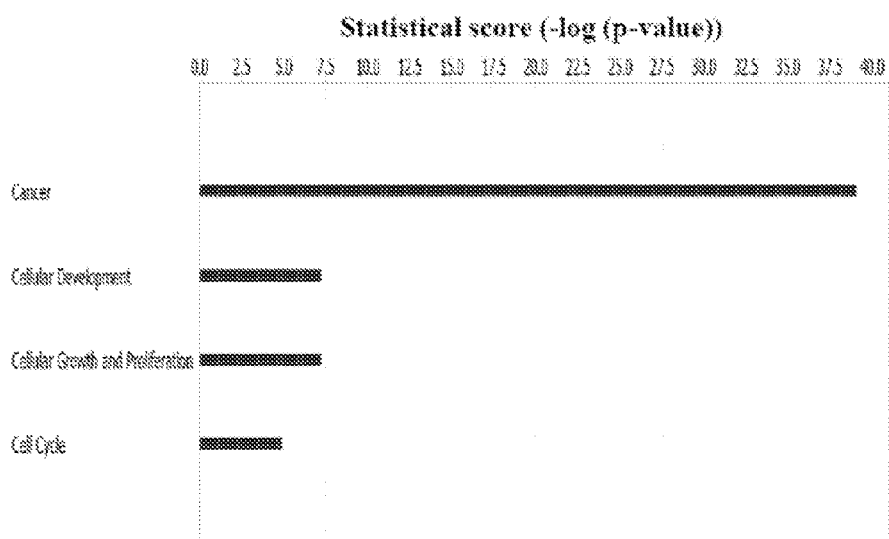

To distinguish miRNA signatures between melanoma cell-derived exosomes and normal melanocyte-derived exosomes, the present inventors compared the miRNome in A375 and HEMa-LP exosomes. The present inventors identified 130 miRNAs upregulated and 98 miRNAs downregulated in A375 versus HEMa-LP exosomes (Table 8). Ingenuity analysis showed that many differentially expressed miRNAs were associated with cancer (70 miRNAs) (FIG. 4B). These differentially expressed miRNAs also function in cellular growth and proliferation (22 miRNAs), cellular development (15 miRNAs), cellular movement (13 miRNAs), and cell cycle (9 miRNAs) (FIG. 4B). Among the dysregulated miRNAs were hsa-miR-31 and -185, which are related to regulation of aggressive features of melanoma [32], and hsa-miR-34b, which has been shown to be involved in melanoma invasiveness [33]. The present inventors listed 15 dysregulated miRNAs that are known to be associated with melanoma metastasis after ingenuity analysis (Table 1). Regression analysis showed that miRNA signals were less correlated between A375 and HEMa-LP exosomes (r=0.493891) (FIG. 5C). These results suggest that a substantial difference in miRNA expression profile exists between normal melanocyte-derived exosomes and melanoma cell-derived exosomes. Melanoma exosomes express a group of miRNAs that may play important roles in melanoma progression and metastasis.

Differential Protein Expression Signatures of A375 and HEMa-LP Exosomes.

Figure 6:
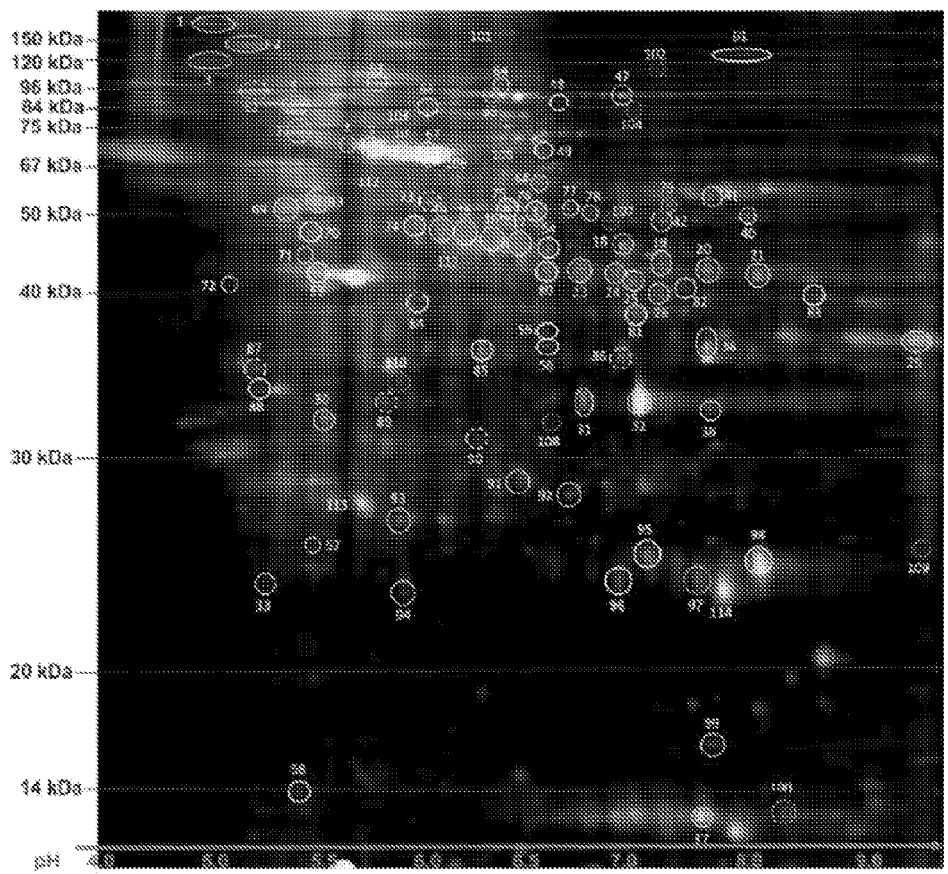
FIG. 6. 2-D DIGE analysis of A375 exosomes versus HEMa-LP exosomes. 25 µg of proteins from A375 exosomes (labeled with Cy5, red) and HEMa-LP exosomes (labeled with Cy3, green) were separated by isoelectric focusing (IEF) in the first dimension and SDS polyacrylamide gel electrophoresis (SDS-PAGE) in the second dimension. Overlay image was generated by ImageQuant software. Differentially expressed protein spots were circled and stored for further protein identification.

Functional mRNAs in exosomes can be translated and post-transcriptionally modified into protein to exert their function. miRNAs are upstream regulators that can simultaneously target large numbers of protein-coding genes and multiple cancer pathways. On the other hand, miRNAs are the direct functional product of the corresponding gene. Exosomal mRNAs, miRNAs, and proteins are woven together to form a large network of messengers and mediators for melanoma progression. Unveiling the protein profile in exosomes is the last necessary step toward the understanding of melanoma exosomes. To this end, the present inventors analyzed the protein profiles between the A375 and HEMa-LP exosomes. FIG. 6 shows the 2-D overlapping image of A375 and HEMa-LP exosome protein expression. Selected proteins have been identified and are listed in Table 2. Among the identified proteins were annexin A1, annexin A2, syntenin-1, and hyaluronan and proteoglycan link protein 1 (HAPLN1), which all have functions related to angiogenesis, melanoma cell invasion, migration, and metastasis [23, 31, 34, 35]. Interestingly, annexin A1 was upregulated while annexin A2 was downregulated in A375 exosomes. These results show that tumor exosomes have some distinctive proteins that may have significant and specific activities during melanoma progression and metastasis.

Correlation of Expression Levels of Selected miRNAs with their Predicted Targeted Genes.

Figure 7:
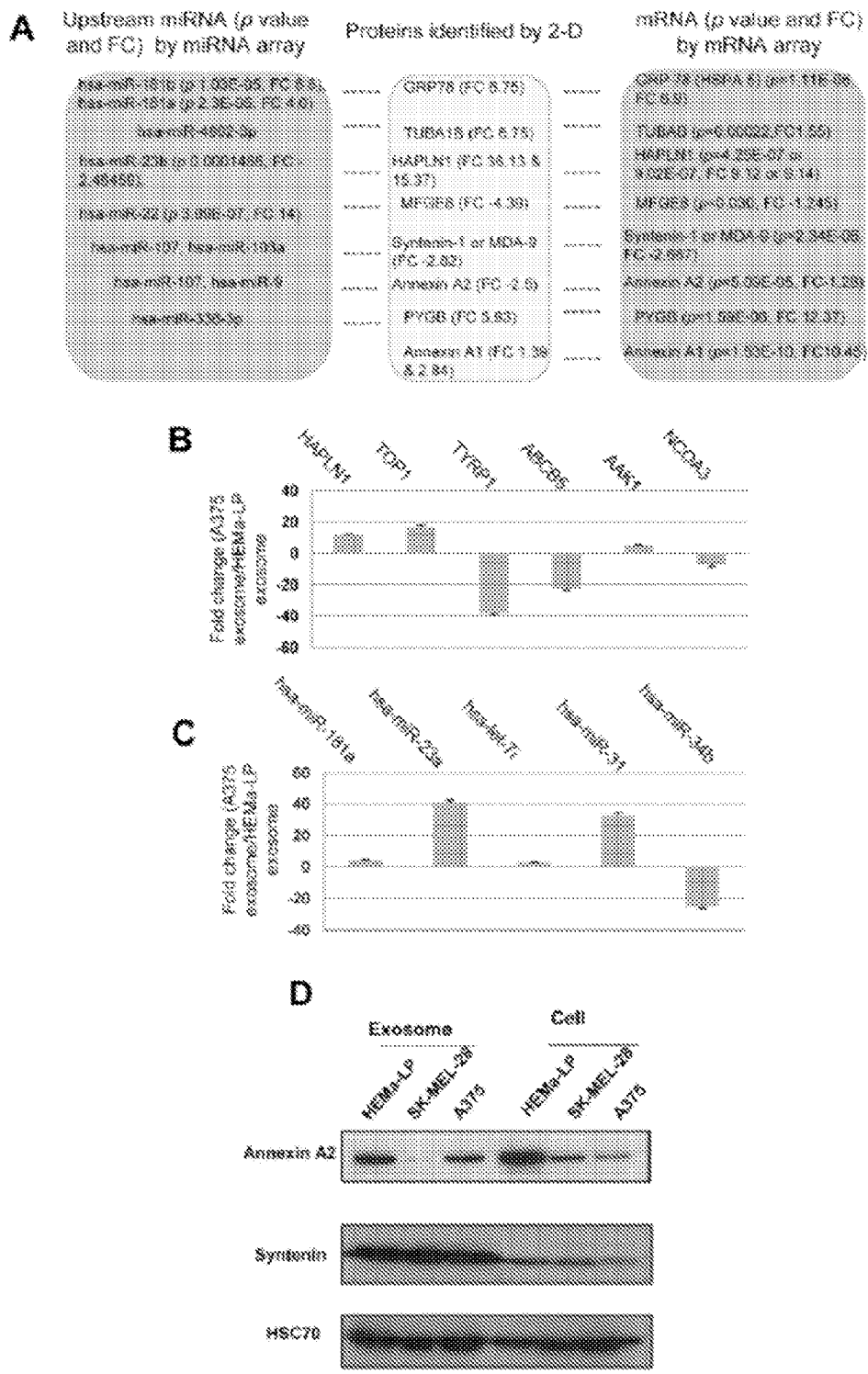
FIG. 7. Interaction and validation of differentially expressed mRNAs, miRNAs, and proteins in A375 versus HEMa-LP exosomes. (A) Correlation of differentially expressed mRNAs, miRNAs, and proteins in A375 exosomes versus HEMa-LP exosomes (FC=fold change). Total exosomal RNA was reverse transcribed to cDNA for mRNA and miRNA validation. Expression levels of mRNA (B) or miRNA (C) were analyzed by RT-PCR. Samples were run in triplicate with at least 3 independent experiments. The bars represent normalized percentage (%) of fold change values with mean±SD between A375 and HEMa-LP exosomes. (D) Total exosomal protein was extracted for Western blotting analysis using antibodies as designated. HSC70 was used as a loading control.

Having identified exosomal mRNA, miRNA, and protein signatures, the interactions among these differentially expressed mRNAs, miRNAs, and proteins were investigated. The present inventors focused on expression signatures between A375 exosomes and HEMa-LP exosomes. FIG. 7A lists some of these mass spectrometry-identified proteins and correlates them with their differentially expressed genes in mRNA array, and their upstream miRNAs. Except for ferritin (heavy polypeptide 1), the alterations of the mRNA expression levels parallel their protein expression levels. The present inventors found no correlating mRNA probes for ferritin (heavy polypeptide 1) in mRNA array. However, another mRNA isoform of ferritin (light polypeptide) was found downregulated by 1.56 fold with a p value of 1.27E-06.

The present inventors also searched for the upstream miRNAs that may target identified differentially expressed proteins, using TargetScanHuman 6.0. Some of the upstream miRNAs were inversely expressed with their targeted proteins. These results implied that exosomal mRNAs, miRNAs, and proteins form an intricate network to execute signal transduction and melanoma progression.

The present inventors have confirmed some of the differentially expressed mRNA (FIG. 7B) and miRNA (FIG. 7C) by semi-quantitative real time RT-PCR. The present inventors also confirmed that 5 of the randomly-chosen non-differentially expressed mRNAs, or miRNAs, were not significantly expressed in this real time RT-PCR experiment (data not shown). Some of the differentially expressed protein levels were confirmed by Western blotting (FIG. 7D). These results validate the mRNA, miRNA array and 2-D proteomic results.

Normal Melanocytes Acquire Invasiveness Through Uptaking of Melanoma Cell-Derived Exosomes.

Figure 8:
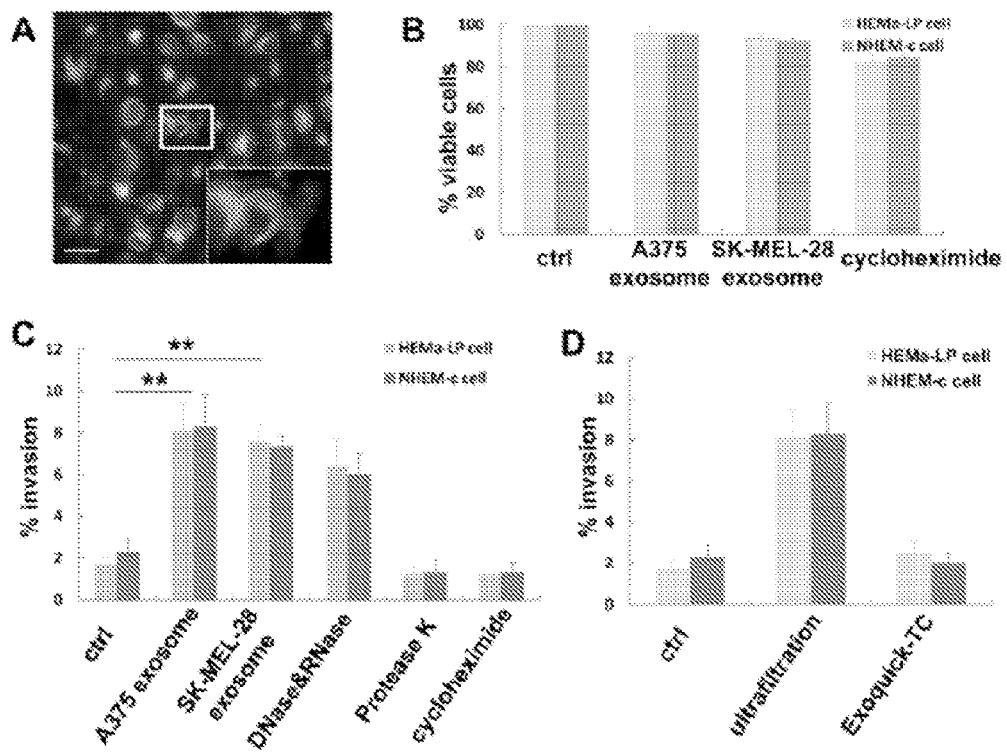
FIG. 8. Melanoma exosomes are taken up by normal melanocytes and conferred invasion ability on normal melanocytes. (A) HEMa-LP cells and A375 exosomes were labeled using the green fluorescent dye PKH67 and the red fluorescent dye PKH26 respectively. After incubating the labeled A375 exosomes with HEMa-LP cells for 24 h, confocal microscopy images were taken (magnification, ×600). The overlay image shows A375 exosomes (red) were internalized by HEMA-LP cells (green). The insert represents higher magnification of the boxed area (scale bar=20 µm). (B) MTT assay of HEMa-LP and NHEM-c cells incubating with media only (control), A375 exosomes, SK-MEL-28 exosomes, and cycloheximide. (C) Percent invasion of HEMa-LP and NHEM-c cells after incubation of 5 days with A375 exosomes, SK-MEL-28 exosomes, pretreatment of DNase and RNase A with A375 exosomes, pretreatment of Protease K with A375 exosomes, and treatment of A375 exosomes with cycloheximide. (D) Comparison of percent invasion in HEMa-LP cells and NHEM-c cells using exosomes isolated by a combination of ultrafiltration and ultracentrifugation and by Exoquick-TC precipitation. Each invasion assay experiment was performed in triplicate, and data from three independent experiments are presented. (**$p<0.01$, significant in comparison with control).

In order to clarify how tumor-derived exosomes transport their active molecules into the cells and subsequently affect the function of the cells, the present inventors incubated A375 or SK-MEL-28 melanoma exosomes with normal melanocytes HEMa-LP and NHEM-c. The present inventors first checked whether cells can internalize exosomes in vitro. After incubation for 24 h, confocal microscopy demonstrated that red-fluorescent vesicles were internalized in green fluorescent-labeled cells, suggesting uptake of A375 exosomes by HEMa-LP cells (FIG. 8A).

The present inventors then examined whether melanoma exosomes affect the growth and proliferation of normal melanocytes. MTT analysis showed that both A375 and SK-MEL-28 exosomes have no obvious effects on HEMa-LP and NHEM-c cell growth and proliferation (FIG. 8B). Because the migration/invasion assay also controls for proliferation, the present inventors used this method to further support the MTT results, and to evaluate the invasion ability of normal melanocytes after uptake of melanoma exosomes. After incubation of A375 or SK-MEL-28 exosomes with HEMa-LP cells or NHEM-c cells for 5 days, results from the migration/invasion assay showed that the percent invasion of HEMa-LP cells or NHEM-c cells was significantly greater than those of the control cells (FIG. 8C). To ensure the exosome transfer mediates this invasion ability of normal melanocytes, the present inventors pretreated melanoma exosomes with DNase and RNase A or protease K, and then incubated with normal melanocytes. The results showed that pretreatment of melanoma exosomes with DNase and RNase A have no significant effects on the increased invasion ability of normal melanocytes. But protease K pretreatment did decrease the invasion ability of normal melanocytes (FIG. 8C). Interestingly, the addition of cycloheximide (at 0.1 µg/ml), a protein synthesis inhibitor, to HEMa-LP cell or NHEM-c cell media inhibited the invasion ability of HEMa-LP cells or NHEM-c cells promoted by A375 or SK-MEL-28 exosomes (FIG. 8C) without significantly inhibiting HEMa-LP or NHEM-c cell growth (more than 80% viable cells; FIG. 8B). These data suggest that melanoma exosomes can transport functionally active mRNA, miRNA and proteins into normal melanocytes and so provide normal cells with invasion ability. This process is dependent on new protein synthesis.

The present inventors compared the migration/invasion inducing capacity of exosomes isolated by another method, exosome precipitation by Exoquick-TC, with the method of combination of ultrafiltration and ultracentrifugation. The results showed that A375 or SK-MEL-28 exosomes precipitated from 10 ml of cell culture supernatant by Exoquick-TC have barely any effects on the invasion abilities of HEMa-LP or NHEM-c cells (FIG. 8D). This suggested that exosomes precipitated from 10 ml cell culture media may not be enough to induce the invasion ability of normal melanocytes. Sufficient melanoma exosomes might be needed to confer this normal cell invasion ability.

Gene Expression Changes in Normal Melanocytes after Uptake of Melanoma Cell-Derived Exosomes.

Figure 9:
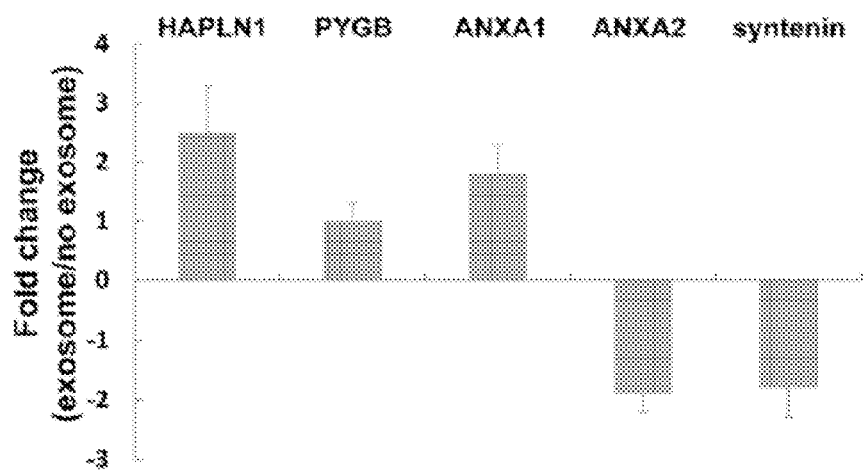
FIG. 9. Gene expression changes of normal melanocyte after taking-up melanoma cell-derived exosomes. HEMa-LP cells were seeded in a 6-well plate. The next day, A375 exosomes were added into the plate. No exosome media was used as a control. After 5 days, total HEMa-LP cell RNA was isolated by mirVana kit and reverse transcribed to cDNA. Expression levels of mRNA were analyzed by RT-PCR. Samples were run in triplicate with at least 3 independent experiments. The bars represent normalized percentage (%) of fold change values with mean±SD between HEMa-LP cells with exosomes and with no exosomes.

The present inventors further investigated if there were any gene expression changes in HEMa-LP cells after HEMa-LP cells acquired invasion ability through co-incubation with A375 melanoma exosomes. The present inventors focused on those genes that have distinguished differential expression in A375 exosomes: HAPLN1, PYGB, syntenin (MDA-9), ANXA1, and ANXA2. The present inventors expected that those highly expressed proteins in A375 melanoma exosomes might be detected in HEMa-LP cells after co-incubation. RT-PCR results showed that after incubating with A375 exosomes, ANXA2 and syntenin in HEMa-LP cells were modestly downregulated by 1.9 fold and 1.5 fold, respectively. HAPLN1, PYGB, and ANXA1 in HEMa-LP cells were upregulated by 2.5, 1, and 1.8 fold, respectively (FIG. 9). These changes suggest that after exosomes transfer their molecules into the cells, cell function is fine-tuned.

TABLE 1

Differentially expressed miRNAs related to melanoma metastasis between A375 exosomes and HEMa-LP exosomes

| Probe ID | Genes in dataset | Fold Change |
|---|---|---|
| hsa-let-7c_st | let-7a/let7f/let-7c (includes others) | 61.026 |
| hsa-miR-138_st | miR-138 | 51.192 |
| hsa-miR-125b_st | miR-125b-5p/miR-125a-5p/miR-125b (includes others) | 43.944 |
| hsa-miR-130a_st | miR-130a/miR-130b/miR-301a (includes others) | 39.317 |
| hsa-miR-34a_st | miR-449a/miR-34a/miR-34c (includes others) | 34.025 |
| hsa-miR-196a_st | miR-196a/miR-196b | 18.635 |
| hsa-miR-199b-3p_st | miR-199a-3p | 8.677 |
| hsa-miR-25_st | miR-92a/miR-92b/miR-32 (includes others) | 6.089 |
| hsa-miR-27a_st | miR-27b/miR-27a | 5.906 |
| hsa-miR-200b_st | miR-429/miR-200b/miR-200c | −2.356 |
| hsa-miR-23b_st | miR-23b/miR-23a/miR-23c (includes others) | −2.465 |
| hsa-miR-146a_st | miR-146a/miR-146b/miR-146b-5p | −2.694 |
| hsa-miR-613_st | miR-1/miR-206/miR-1a | −18.102 |
| hsa-miR-205_st | miR-205 | −18.922 |
| hsa-miR-149_st | miR-149 | −67.514 |

TABLE 2

Identities of differentially expressed proteins in A375 exosomes versus HEMa-LP exosomes

| Assigned spot # | Ratio of A375 exosome/HEMa-LP exosome | Proteins identified | Protein accession number |
|---|---|---|---|
| 7 | 6.75 | 78 KDa glucose-regulated protein precursor (GRP78) | gi\|16507237 |
| 13 | 2.79 | Tublin, alpha 1A (TUBA1B) | gi\|18204869 |
| 17 & 14 | 36.13 & 15.37 | Hyaluronan and proteoglycan link protein 1 (HAPLN1) | gi\|4503053 |
| 21 | −4.39 | milk fat globule-EGF factor 8 protein (MFGE8) | gi\|119622432 |
| 32 | −2.82 | Syntenin-1 isoform 1 (SDCBP, MDA-9) | gi\|55749490 |
| 36 | −2.5 | Annexin A2 (ANXA2) | gi\|50845388 |
| 48 | 5.93 | brain glycogen phosphorylase(PYGB) | gi\|62087740 |
| 55 & 56 | 1.39 & 2.84 | Annexin A1 (ANXA1) | gi\|119582950, gi\|4502101 |
| 62 | 2.78 | Endoplasmin precursor (gp 96) | gi\|4507677 |
| 79 | −2.08 | 3-oxoacid CoA transferase (OXCT) | gi\|48146215 |
| 94 | 2.96 | ferritin, heavy polypeptide 1, isoform CRA_e | gi\|119594401 |

TABLE 3

Differentially expressed mRNA probe sets in HEMa-LP exosomes versus HEMa-LP cells (FDR corrected p < 0.01 and FC > 5 or FC < −5)

| Probe Set ID | Gene Symbol | Gene Title | p-value | Fold Change |
|---|---|---|---|---|
| 1558579_at | FLJ37786 | hypothetical LOC642691 | 3.37E−07 | 138.905 |
| 242344_at | GABRB2 | gamma-aminobutyric acid (GABA) A receptor, beta 2 | 3.30E−08 | 68.9541 |
| 232034_at | LOC203274 | Hypothetical protein LOC203274 | 3.80E−09 | 47.5815 |
| 243689_s_at | FRG1B | FSHD region gene 1 family, member B | 4.74E−07 | 46.7441 |
| 1553186_x_at | RASEF | RAS and EF-hand domain containing | 5.62E−09 | 43.9333 |
| 1553185_at | RASEF | RAS and EF-hand domain containing | 1.16E−08 | 43.4978 |
| 211565_at | SH3GL3 | SH3-domain GRB2-like 3 | 1.07E−07 | 42.523 |
| 222891_s_at | BCL11A | B-cell CLL/lymphoma 11A (zinc finger protein) | 2.98E−08 | 40.1701 |
| 232523_at | MEGF10 | multiple EGF-like-domains 10 | 5.28E−10 | 40.0672 |
| 244631_at | LOC389834 | ankyrin repeat domain 57 pseudogene | 2.64E−07 | 36.8863 |

TABLE 3-continued

Differentially expressed mRNA probe sets in HEMa-LP exosomes versus HEMa-LP cells
(FDR corrected p < 0.01 and FC > 5 or FC < −5)

| Probe Set ID | Gene Symbol | Gene Title | p-value | Fold Change |
| --- | --- | --- | --- | --- |
| 228260_at | ELAVL2 | ELAV (embryonic lethal, abnormal vision, *Drosophila*)-like-2 (Hu antigen B) | 1.86E−08 | 36.609 |
| 1560431_at | PGM5P1 | phosphoglucomutase 5 pseudogene 1 | 2.96E−07 | 36.0777 |
| 220167_s_t | TP53TG3 /// TP53TG3B | TP53 target 3 /// TP53 target 3B | 6.13E−08 | 35.2851 |
| 1564856_s_at | LOC727924 | hypothetical LOC727924 | 2.86E−08 | 32.4877 |
| 242712_x_at | RANBP2 /// RGPD1 /// RGPD2 /// RGPB3 /// RGPD4 /// RGPD5 /// RGPB6 /// RGPD8 | RAN binding protein 2 /// RANBP2-like and GRIP domain containing 1 /// RANBP2-li | 3.92E−07 | 31.0186 |
| 210800_at | TIMM8A | translocase of inner mitochondrial membrane 8 homolog A (yeast) | 2.34E−06 | 30.4349 |
| 234911_s_at | DCBLD2 | discoidin, CUB and LCCL domain containing 2 | 2.03E−09 | −61.3369 |
| 221730_at | COL5A2 | collagen, type V, alpha 2 | 3.69E−09 | −61.8503 |
| 225673_at | MYADM | myeloid-associated differentiation marker | 2.06E−06 | −61.9353 |
| 203042_at | LAMP2 | lysosomal-associated membrane protein 2 | 4.94E−08 | −62.4991 |
| 213241_at | PLXNC1 | plexin C1 | 4.10E−07 | −63.0386 |
| 226675_s_at | MALAT1 | metastasis associated lung adenocarcinoma transcript 1 (non-protein coding) | 2.89E−05 | −63.4635 |
| 200900_s_at | M6PR | mannos-6-phosphate receptor (cation dependent) | 1.91E−07 | −64.7081 |
| 235197_s_at | OSTM1 | osteopetrosis associated transmembrane protein 1 | 3.00E−07 | −65.3892 |
| 208689_s_at | RPN2 | ribophorin II | 5.04E−10 | −66.0527 |
| 211936_at | HSPA5 | heat shock 70 kDa protein 5 (glucose-regulated protein, 78 kDa) | 1.08E−08 | −66.7859 |
| 201324_at | EMP1 | epithelial membrane protein 1 | 8.48E−08 | −67.0523 |
| 227048_at | LAMA1 | laminin, alpha 1 | 5.55E−09 | −67.934 |
| 1555579_s_at | PTPRM | protein tyrosine phosphatase, receptor type, M | 2.47E−08 | −68.3192 |
| 224967_at | UGCG | UDP-glucose ceramide glucosyltransferase | 6.35E−09 | −68.8794 |
| 220924_s_at | SLC38A2 | solute carrier family 38, member 2 | 1.26E−08 | −71.6044 |
| 201847_at | LIPA | lipase A, lysosomal acid, cholesterol esterase | 9.35E−12 | −73.6834 |
| 201149_s_at | TIMP3 | TIMP metallopeptidase inhibitor 3 | 8.58E−10 | −76.6155 |
| 202283_at | SERPINF1 | serpin peptidase inhibitor, clade F (alpha-2 antiplasmin, pigment epithelium der | 5.90E−08 | −76.6953 |
| 201300_s_at | PRNP | prion protein | 1.48E−08 | −77.0587 |
| 228776_at | GJC1 | gap junction protein, gamma 1, 45 kDa | 2.50E−09 | −77.9266 |
| 203041_s_at | LAMP2 | lysosomal-associated membrane protein 2 | 2.72E−09 | −79.2481 |
| 201325_s_at | EMP1 | epithelial membrane protein 1 | 4.93E−08 | −79.5754 |
| 213067_at | MYH10 | myosin, heavy chain 10, non-muscle | 1.94E−10 | −81.2182 |
| 201662_s_at | ACSL3 | acyl-CoA synthetase long-chain family member 3 | 6.01E−08 | −84.8046 |
| 202068_s_at | LDLR | low density lipoprotein receptor | 5.27E−10 | −85.271 |
| 204602_at | DKK1 | dickkopf homolog 1 (*Xenopus laevis*) | 1.53E−09 | −85.4836 |
| 223940_x_at | MALAT1 | metastasis associated lung adenocarcinoma transcript 1 (non-protein coding) | 9.81E−08 | −86.9581 |
| 206638_at | HTR2B | 5-hydroxytryptamine (serotonin) receptor 2B | 2.36E−08 | −89.1755 |
| 201005_at | CD9 | CD9 molecule | 2.00E−08 | −93.3099 |
| 1555505_a_at | TYR | tyrosinase (oculocutaneous albinism IA) | 1.26E−06 | −95.6084 |

TABLE 3-continued

Differentially expressed mRNA probe sets in HEMa-LP exosomes versus HEMa-LP cells
(FDR corrected p < 0.01 and FC > 5 or FC < −5)

| Probe Set ID | Gene Symbol | Gene Title | p-value | Fold Change |
|---|---|---|---|---|
| 1557910_at | HSP90AB1 | heat shock protein 90 kDa alpha (cytosolic), class B member 1 | 1.68E−07 | −115.499 |
| 201147_s_at | TIMP3 | TIMP metallopeptidase inhibitor 3 | 2.19E−11 | −123.392 |
| 1558678_s_at | MALAT1 | metastasis associated lung adenocarcinoma transcript 1 (non-protein coding) | 4.80E−08 | −138.785 |
| 200598_s_at | HSP90B1 | heat shock protein 90 kDa beta (Grp94), member 1 | 6.29E−11 | −139.732 |
| 221577_x_at | GDF15 /// LOC100292463 | growth differentiation factor 15 /// similar to growth differentiation factor 15 | 1.18E−09 | −149.921 |
| 224568_x_at | MALAT1 | metastasis associated lung adenocarcinoma transcript 1 (non-protein coding) | 1.97E−06 | −155.517 |
| 201150_s_at | TIMP3 | TIMP metallopeptidase inhibitor 3 | 1.27E−08 | −169.633 |
| 224567_x_at | MALAT1 | metastasis associated lung adenocarcinoma transcript 1 (non-protein coding) | 4.94E−07 | −195.082 |

FC = Fold change
See also, Table S1 of Xiao, et al., "Identifying mRNA, MicroRNA and Protein Profiles of Melanoma Exosomes," PLOS ONE (2012) 7(10): 1-15, which is incorporated herein by this reference.

TABLE 4

Differentially expressed mRNA probe sets in A375 exosomes versus A375 cells
(FDR corrected p < 0.01 and FC > 2 or FC < −2)

| Probeset ID | Gene Symbol | Gene Title | p-value | Fold Change |
|---|---|---|---|---|
| 226018_at | C7orf41 | chromosome 7 open reading frame 41 | 1.55E−07 | 35.256 |
| 202125_s_at | TRAK2 | trafficking protein, kinesin binding 2 | 2.52E−11 | 23.9552 |
| 235054_at | NUDT16 | nudix (nucleoside diphosphate linked moiety X)-type motif 16 | 5.57E−10 | 23.4812 |
| 202437_s_at | CYP1B1 | cytochrome P450, family 1, subfamily B, polypeptide 1 | 6.97E−07 | 23.0524 |
| 219309_at | CTA-216E10.6 | hypothetical FLJ23584 | 1.77E−07 | 22.5127 |
| 225283_at | ARRDC4 | arrestin domain containing 4 | 3.17E−09 | 22.3204 |
| 219011_at | PLEKHA4 | pleckstrin homology domain containing, family A | 1.68E−08 | 20.9104 |
| 202436_s_at | CYP1B1 | cytochrome P450, family 1, subfamily B, polypeptide 1 | 4.77E−08 | 20.6014 |
| 202124_s_at | TRAK2 | trafficking protein, kinesin binding 2 | 1.63E−08 | 18.9632 |
| 228937_at | C13orf31 | chromosome 13 open reading frame 31 | 2.50E−06 | 17.4971 |
| 213252_at | SH3PXD2A | SH3 and PX domains 2A | 1.89E−06 | 14.5224 |
| 212845_at | SAMD4A | sterile alpha motif domain containing 4A | 4.76E−11 | 14.145 |
| 226234_at | GDF11 | growth differentiation, factor 11 | 7.70E−09 | 14.0506 |
| 226977_at | C5orf53 | chromosome 5 open reading frame 53 | 5.18E−09 | 13.6913 |
| 201929_s_at | PKP4 | plakophilin 4 | 6.60E−08 | 13.2348 |
| 223469_at | PGPEP1 | pyroglutamyl-peptidase I | 1.43E−06 | 12.307 |
| 228857_at | GNL1 /// LOC285331 | guanine nucleotide binding protein-like 1 /// hypothetical protein LOC285831 | 1.51E−07 | 11.8758 |
| 236429_at | ZNF83 | zinc finger protein 83 | 1.09E−05 | 11.6237 |
| 201829_at | NET1 | neuroepithelial cell transforming 1 | 3.63E−06 | 11.244 |
| 228231_at | LOC100287081 | similar to hCG1999172 | 1.49E−07 | 11.1814 |
| 208740_at | SAP18 | Sin3A-associated protein, 18 kDa | 2.88E−08 | 11.1473 |
| 202435_s_at | CYP1B1 | cytochrome P450, family 1, subfamily B, polypeptide 1 | 2.52E−07 | 10.3664 |
| 214414_x_at | HBA1 /// HBA2 | hemoglobin, alpha 1 /// hemoglobin, alpha 2 | 1.78E−08 | 9.909 |
| 212764_at | ZEB1 | zinc finger E-box binding homeobox 1 | 4.27E−05 | 9.12679 |
| 226656_at | CRTAP | cartilage associated protein | 8.06E−10 | 8.8118 |
| 224817_at | SH3PXD2A | SH3 and PX domains 2A | 1.64E−09 | 8.52468 |
| 208741_at | SAP18 | Sin3A-associated protein 18 kDa | 2.44E−06 | 8.47444 |
| 209311_at | BCL2L2 | BCL2-like 2 | 1.26E−07 | 8.25949 |
| 204426_at | TMED2 | transmembrane emp24 domain trafficking protein 2 | 2.28E−05 | −12.1006 |
| 202012_s_at | EXT2 | exostoses (multiple) 2 | 7.70E−08 | −12.1215 |
| 207332_s_at | TFRC | transferrin receptor (p90, CD71) | 6.95E−09 | −12.2876 |
| 230265_at | SEL1L | Sel-1 suppressor of lin-12-like (C. elegans) | 9.24E−06 | −12.3784 |

TABLE 4-continued

Differentially expressed mRNA probe sets in A375 exosomes versus A375 cells
(FDR corrected p < 0.01 and FC > 2 or FC < −2)

| Probeset ID | Gene Symbol | Gene Title | p-value | Fold Change |
|---|---|---|---|---|
| 219479_at | KDELC1 | KDEL (Lys-Asp-Glu-Leu) containing 1 | 2.53E−08 | −12.588 |
| 201324_at | EMP1 | epithelial membrane protein 1 | 1.67E−06 | −12.7525 |
| 208783_s_at | CD46 | CD46 molecule, complement regulatory protein | 5.74E−06 | −12.9425 |
| 209278_s_at | TFPI2 | tissue factor pathway inhibitor 2 | 1.92E−08 | −12.9541 |
| 216942_s_at | CD58 | CD58 molecule | 5.79E−08 | −13.0048 |
| 201940_at | CPD | carboxypeptidase D | 1.27E−06 | −13.1105 |
| 229899_s_at | C20orf199 | chromosome 20 open reading frame 199 | 3.59E−06 | −13.2474 |
| 217777_s_at | PTPLAD1 | protein tyrosine phosphatase-like A domain containing 1 | 7.98E−07 | −13.2558 |
| 1555120_at | CD96 | CD96 molecule | 1.81E−06 | −13.284 |
| 202236_s_at | SLC16A1 | solute carrier family 16, member 1 (monocarboxylic acid transporter 1) | 4.99E−08 | −13.3239 |
| 222404_x_at | PTPLAD1 | protein tyrosine phosphatase-like A domain containing 1 | 1.61E−08 | −13.3564 |
| 210764_s_at | CYR61 | cysteine-rich, angiogenic inducer, 61 | 5.09E−08 | −13.7628 |
| 207345_at | FST | follistatin | 5.23E−06 | −13.9206 |
| 218652_s_at | PIGG | phosphatidylinositol glycan anchor biosynthesis, class G | 2.29E−07 | −14.2021 |
| 202223_at | STT3A | STT3, subunit of the oligosaccharyltransferase complex, homolog A (*S. cerevisiae*) | 5.41E−07 | −14.3758 |
| 1555460_a_at | SLC39A6 | solute carrier family 39 (zinc transporter), member 6 | 2.61E−06 | −14.9944 |
| 213649_at | SFRS7 | splicing factor, arginine/serine-rich 7, 35 kDa | 4.44E−07 | −14.9967 |
| 204427_s_at | TMED2 | transmembrane emp24 domain trafficking protein 2 | 5.31E−06 | −15.0798 |
| 217743_s_at | TMEM30A | transmembrane protein 30A | 7.32E−06 | −15.3259 |
| 215177_s_at | ITGA6 | integrin, alpha 6 | 5.62E−06 | −15.4727 |
| 234000_s_at | PTPLAD1 | protein tyrosine phosphatase-like A domain containing 1 | 3.88E−08 | −15.709 |
| 203803_at | PCYOX1 | prenylcysteine oxidase 1 | 2.32E−06 | −15.9148 |
| 221730_at | COL5A2 | collagen, type V, alpha 2 | 3.95E−08 | −16.0241 |
| 202089_s_at | SLC39A6 | solute carrier family 39 (zinc transporter), member 6 | 6.70E−08 | −16.0417 |
| 200990_s_at | M6PR | mannose-6-phosphate receptor (cation dependent) | 2.14E−06 | −16.0601 |
| 222853_at | FLRT3 | fibronectin leucine rich transmembrane protein 3 | 1.43E−05 | −16.3719 |
| 207431_s_at | DEGS1 | degenerative spermatocyte homolog 1, lipid desaturase (*Drosophila*) | 5.37E−06 | −16.5093 |
| 227517_s_at | GAS5 | growth arrest-specific 5 (non-protein coding) | 5.07E−09 | −16.6185 |
| 214895_s_at | ADAM10 | ADAM metallopeptidase domain 10 | 1.86E−06 | −16.619 |
| 224917_at | MIR21 | microRNA 21 | 6.74E−06 | −16.7312 |
| 1555878_at | RPS24 | Ribosomal protein S24 | 2.25E−07 | −16.9962 |
| 1554679_a_at | LAPTM4B | lysosomal protein transmembrane 4 beta | 1.16E−07 | −17.4328 |
| 201108_s_at | THBS1 | thrombospondin 1 | 9.04E−06 | −17.546 |
| 201444_s_at | ATP6AP2 | ATPase, H+ transporting, lysosomal accessory protein 2 | 7.52E−07 | −18.1079 |
| 201110_s_at | THBS1 | thrombospondin 1 | 5.46E−06 | −18.6687 |
| 235086_at | THBS1 | Thrombospondin 1 | 4.16E−07 | −19.59 |
| 228496_s_at | CRIM1 | Cysteine rich transmembrane BMP regulator 1 (chordin-like) | 9.19E−07 | −21.4683 |
| 208097_s_at | TMX1 | thioredoxin-related transmembrane protein 1 | 5.46E−08 | −21.5641 |
| 222040_at | HNRNPA1 | heterogeneous nuclear ribonucleoprotein A1 | 2.60E−10 | −22.3148 |
| 202551_s_at | CRIM1 | cysteine rich transmembrane BMP regulator 1 (chordin-like) | 5.20E−08 | −23.2588 |
| 201109_s_at | THBS1 | thrombospondin 1 | 4.47E−09 | −27.9195 |
| 204602_at | DKK1 | dickkopf homolog 1 (*Xenopus laevis*) | 3.36E−09 | −49.5911 |

FC = Fold change

See also, Table S2 of Xiao, et al., "Identifying mRNA, MicroRNA and Protein Profiles of Melanoma Exosomes," PLOS ONE (2012) 7(10): 1-15, which is incorporated herein by this reference.

TABLE 5

Differentially expressed mRNA probe sets in A375 exosomes versus HEMa-LP exosomes
(FDR corrected p < 0.01 and FC > 5 or FC < −5)

| Probeset ID | Gene Symbol | Gene Title | p-value | Fold Change |
|---|---|---|---|---|
| 206172_at | IL13RA2 | interleukin 13 receptor, alpha 2 | 2.29E−08 | 252.587 |
| 214254_at | MAGEA4 | melanoma antigen family A, 4 | 2.25E−08 | 151.952 |
| 214451_at | TFAP2B | transcription factor AP-2 beta (activating enhancer binding protein 2 beta) | 2.96E−11 | 147.491 |
| 1557910_at | HSP90AB1 | heat shock protein 90 kDa alpha (cytosolic), class B member 1 | 1.46E−07 | 129.662 |
| 205047_s_at | ASNS | asparagine synthetase (glutamine-hydrolyzing) | 2.22E−08 | 127.13 |
| 1567912_s_at | CT45A1 /// CT45A2 /// CT45A3 /// CT45A4 /// CT45A5 /// CT45A6 /// LOC100133581 | cancer/testis antigen family 45, member A1 /// cancer/testis antigen family 45, | 2.82E−08 | 110.883 |
| 212764_at | ZEB1 | zinc finger E-box binding homeobox 1 | 5.98E−07 | 97.902 |
| 210467_x_at | MAGEA12 | melanoma antigen family A, 12 | 3.63E−10 | 96.4183 |
| 264698_at | ISG20 | interferon stimulated exonuclease gene 20 kDa | 6.48E−10 | 92.4454 |
| 209258_s_at | SMC3 | structural maintenance of chromosomes 3 | 9.39E−08 | 91.0301 |
| 235700_at | CT45A5 | cancer/testis antigen family 45, member A3 | 1.04E−07 | 85.6778 |
| 202237_at | NNMT | nicotinamide N-methyltransferase | 3.78E−11 | 84.6153 |
| 209942_x_at | MAGEA3 | melanoma antigen family A, 3 | 1.60E−08 | 82.9397 |
| 211674_x_at | CTAG1A /// CTAG1B | cancer/testis antigen 1A /// cancer/testis antigen 1B | 7.06E−09 | 82.7485 |
| 206201_s_at | MEOX2 | mesenchyme homeobox 2 | 3.15E−07 | 79.6159 |
| 203186_s_at | S100A4 | S100 calcium binding protein A4 | 4.72E−10 | 76.4952 |
| 1553394_a_at | TFAP2B | transcription, factor AP-2 beta (activating enhancer binding protein 2 beta) | 7.67E−10 | 75.9662 |
| 208835_s_at | LUC7L3 | LUC7-like 3 (S. cerevisiae) | 3.14E−10 | 70.2199 |
| 202157_s_at | CELF2 | CUGBP, Elav-like family member 2 | 2.95E−08 | −43.7686 |
| 214475_x_at | CAPN3 | calpain 3, (p94) | 6.37E−10 | −46.3977 |
| 237070_at | TRPM1 | transient receptor potential cation channel, subfamily M, member 1 | 4.22E−06 | −48.6691 |
| 213638_at | PHACTR1 | phosphatase and actin regulator 1 | 7.19E−09 | −48.8598 |
| 201909_at | RPS4Y1 | ribosomal protein S4, Y-linked 1 | 6.33E−10 | −77.5149 |
| 210944_s_at | CAPN3 | calpain 3, (p94) | 5.88E−10 | −78.1748 |
| 206426_at | MLANA | melan-A | 1.19E−07 | −151.066 |
| 206427_s_at | MLANA | melan-A | 1.04E−10 | −289.633 |
| 205694_at | TYRP1 | tyrosinase-related protein 1 | 1.01E−08 | −377.17 |

See also, Table S3 of Xiao, et al., "Identifying mRNA, MicroRNA and Protein Profiles of Melanoma Exosomes," PLOS ONE (2012) 7(10): 1-15, which is incorporated herein by this reference.

TABLE 6

Differentially expressed miRNAs in HEMa-LP exosomes versus HEMa-LP cells

| Probeset ID | Transcript ID | p-value | Fold change |
|---|---|---|---|
| hsa-miR-1281_st | hsa-mir-1281 | 5.97E−05 | 24.5167 |
| hsa-miR-937_st | hsa-mir-937 | 6.98E−05 | 14.6535 |
| hsa-miR-485-3p_st | hsa-mir-485 | 0.000503 | 13.5511 |
| hsa-miR-149_st | hsa-mir-149 | 0.000281 | 11.4336 |
| hsa-let-7b-star_st | hsa-let-7b | 0.000448 | 11.0758 |
| hsa-miR-411-star_st | hsa-mir-411 | 0.000483 | 9.73162 |
| hsa-miR-138-1-star_st | hsa-mir-138-2 // bsa-mir-138-1 | 0.000141 | 8.52909 |
| hsa-miR-885-5p_st | hsa-mir-885 | 0.000739 | 8.49963 |
| hsa-miR-935_st | hsa-mir-935 | 3.84E−05 | 8.29224 |
| hsa-miR-1178_st | hsa-mir-1178 | 0.000191 | 7.73233 |
| hsa-miR-605_st | hsa-mir-605 | 0.000653 | 5.01592 |
| hsa-miR-105_st | hsa-mir-105-1 // hsa-mir-105-2 | 4.30E−05 | 4.79352 |
| hsa-miR-574-3p_st | hsa-mir-574 | 0.000586 | 4.43565 |
| hsa-miR-345_st | hsa-mir-345 | 5.31E−07 | 4.43372 |
| hsa-miR-92a_st | hsa-mir-92a-1 // hsa-mir-92a-2 | 0.000318 | −2.12635 |
| hsa-miR-93_st | hsa-mir-93 | 0.000446 | −2.51837 |
| hsa-miR-106a_st | hsa-mir-106a | 4.92E−05 | −2.80903 |
| hsa-miR-25_st | hsa-mir-25 | 8.28E−05 | −3.24971 |
| hsa-miR-152_st | hsa-mir-152 | 9.25E−05 | −3.70427 |
| hsa-miR-501-3p_st | hsa-mir-501 | 0.000488 | −4.18186 |
| hsa-miR-221_st | hsa-mir-221 | 5.35E−07 | −4.36727 |
| hsa-miR-222_st | hsa-mir-222 | 1.55E−08 | −4.48084 |

TABLE 6-continued

Differentially expressed miRNAs in HEMa-LP exosomes versus HEMa-LP cells

| Probeset ID | Transcript ID | p-value | Fold change |
|---|---|---|---|
| hsa-miR-425__st | hsa-mir-425 | 0.000103 | −4.70861 |
| hsa-miR-1307__st | hsa-mir-1307 | 0.000652 | −4.96735 |
| hsa-miR-361-5p__st | hsa-mir-361 | 0.000136 | −5.06123 |
| hsa-miR-1275__st | hsa-mir-1275 | 0.00079 | −5.13698 |
| hsa-miR-584__st | hsa-mir-584 | 5.57E−06 | −5.17213 |
| hsa-miR-16__st | hsa-mir-16-1 // hsa-mir-16-2 | 7.15E−09 | −5.19881 |
| hsa-miR-320c__st | hsa-mir-320c-1 // hsa-mir-320c-2 | 1.10E−05 | −5.2862 |
| hsa-miR-26a__st | hsa-mir-26a-2 // hsa-mir-26a-1 | 5.91E−08 | −5.29931 |
| hsa-miR-886-5p__st | hsa-mir-886 | 5.33E−06 | −5.3338 |
| hsa-miR-1231__st | hsa-mir-1231 | 5.23E−05 | −5.38751 |
| hsa-miR-675__at | hsa-mir-675 | 0.00065 | −6.02073 |
| hsa-miR-193b__st | hsa-mir-193b | 0.000743 | −6.26696 |
| hsa-miR-1301__st | hsa-mir-1301 | 9.04E−06 | −6.36714 |
| hsa-miR-151-5p__st | hsa-mir-151 | 6.69E−07 | −6.53045 |
| hsa-miR-100__st | hsa-mir-100 | 4.70E−07 | −6.97581 |
| hsa-miR-509-3p__st | hsa-mir-509-2 // hsa-mir-509-3 // hsa-mir-509-1 | 7.22E−05 | −7.70573 |
| hsa-miR-125b__st | hsa-mir-125b-1 // hss-mfr-125b-2 | 0.000285 | −8.20664 |
| hsa-let-7a__st | hsa-let-7a-2 // hsa-let-7a-3 // hsa-let-7a-1 | 2.54E−05 | −8.29224 |
| hsa-miR-23a-star__st | hsa-mir-23a | 0.000156 | −8.34206 |
| hsa-miR-423-5p__st | hsa-mir-423 | 0.000219 | −8.6186 |
| hsa-miR-508-5p__st | hsa-mir-508 | 0.000807 | −9.60974 |
| hsa-miR-15b__st | hsa-mir-15b | 1.03E−06 | −9.74131 |
| hsa-miR-324-3p__st | hsa-mir-324 | 2.49E−05 | −10.2972 |
| hsa-miR-181a__st | hsa-mir-181a-1 // hsa-mir-181a-2 | 1.71E−07 | −10.4074 |
| hsa-miR-193a-5p__st | hsa-mir-193a | 1.70E−05 | −10.4598 |
| hsa-miR-500-star__st | hsa-mir-500 | 0.000179 | −10.8967 |
| hsa-miR-362-5p__st | hsa-mir-362 | 0.000153 | −10.9894 |
| hsa-miR-28-3p__st | hsa-mir-28 | 6.82E−06 | −10.9904 |
| hsa-miR-532-5p__st | hsa-mir-531 | 4.76E−08 | −11.2502 |
| hsa-miR-652__st | hsa-mir-652 | 1.96E−05 | −11.6938 |
| hsa-miR-140-3p__st | hsa-mir-140 | 1.77E−07 | −12.6096 |
| hsa-miR-210__st | hsa-mir-210 | 0.000183 | −13.3195 |
| hsa-miR-502-3p__st | hsa-mir-502 | 1.90E−05 | −14.5111 |
| hsa-miR-31__st | hsa-mir-31 | 3.18E−07 | −15.0315 |
| hsa-miR-1826__st | hsa-mir-1826 | 3.19E−05 | −15.7061 |
| hsa-miR-27a__st | hsa-mir-27a | 1.88E−07 | −16.1907 |
| hsa-miR-20b__st | hsa-mir-20b | 6.32E−07 | −16.9816 |
| hsa-miR-744__st | hsa-mir-744 | 1.13E−06 | −17.4215 |
| hsa-let-7i__st | hsa-let-7i | 2.21E−05 | −17.56 |
| hsa-miR-423-3p__st | hsa-mir-423 | 2.29E−06 | −17.7594 |
| hsa-miR-638__st | hsa-mir-638 | 2.30E−05 | −18.2626 |
| hsa-miR-28-5p__st | hsa-mir-28 | 2.77E−05 | −18.5953 |
| hsa-miR-130b__st | hsa-mir-130b | 3.10E−06 | −19.2517 |
| hsa-miR-181b__st | hsa-mir-181b-1 // hsa-mir-181b-2 | 2.21E−06 | −19.5105 |
| hsa-miR-324-5p__st | hsa-mir-324 | 4.198−06 | −19.6655 |
| hsa-miR-125a-5p__st | hsa-mir-125a | 4.45E−06 | −19.8658 |
| hsa-miR-1268__st | hsa-mir-1268 | 6.63E−05 | −20.0557 |
| hsa-miR-422a__st | hsa-mir-422a | 1.38E−05 | −21.72 |
| hsa-miR-151-3p__st | hsa-mir-151 | 0.000149 | −21.9186 |
| hsa-miR-20a__st | hsa-mir-20a | 5.17E−07 | −22.8969 |
| hsa-miR-29a__st | hsa-mir-29a | 1.86E−06 | −24.6981 |
| hsa-miR-1207-5p__st | hsa-mir-1207 | 4.38E−05 | −27.1836 |
| hsa-miR-19b__st | hsa-mir-19b-1 // hsa-mir-19b-2 | 5.45E−05 | −27.9059 |
| hsa-miR-378__st | hsa-mir-378 | 8.55E−07 | −29.3103 |
| hsa-miR-22__st | hsa-mir-22 | 8.21E−08 | −31.7421 |
| hsa-miR-30d__st | hsa-mir-30d | 5.55E−06 | −37.9814 |
| hsa-miR-155__st | hsa-mir-155 | 0.000206 | −40.6898 |
| hsa-miR-663__st | hsa-mir-663 | 5.72E−08 | −41.699 |
| hsa-let-7c__st | hsa-mir-7c | 1.01E−07 | −46.9213 |
| hsa-miR-138__st | hsa-mir-138-2 // hsa-mir-138-1 | 4.31E−07 | −65.9011 |
| hsa-miR-18a__st | hsa-mir-18a | 7.53E−08 | −66.776 |
| hsa-miR-320d__st | hsa-mir-320d-1 // hsa-mir-320d-2 | 1.32E−05 | −70.6651 |
| hsa-miR-130a__st | hsa-mir-130a | 3.98E−07 | −86.2747 |
| hsa-miR-1228-star__st | hsa-mir-1228 | 6.17E−06 | −110.902 |
| hsa-miR-106b__st | hsa-mir-106b | 3.35E−08 | −128.764 |
| hsa-miR-34a__st | hsa-mir-34a | 5.84E−07 | −155.528 |
| hsa-miR-768-5p__st | hsa-mir-768 | 0.000278 | −250.527 |

TABLE 7

Differentially expressed miRNAs in A375 exosomes versus A375 cells

| Probeset ID | Transcript ID | p-value | Fold change |
|---|---|---|---|
| hsa-miR-575__st | hsa-mir-575 | 2.61E−05 | 46.3023 |
| hsa-miR-149-star_st | hsa-mir-149 | 7.64E−05 | 38.1905 |
| hsa-miR-1300__st | hsa-mir-1300 | 0.000231 | 32.7947 |
| hsa-miR-297__st | hsa-mir-297 | 3.98E−05 | 24.6012 |
| hsa-miR-1224-5p__st | hsa-mir-1224 | 0.000138 | 23.4908 |
| hsa-miR-1225-5p__st | hsa-mir-1225 | 0.000184 | 23.2575 |
| hsa-miR-1228-star__st | hsa-mir-1228 | 1.70E−05 | 22.8388 |
| hsa-miR-92b-star__st | hsa-mir-92b | 0.00015 | 18.8363 |
| hsa-miR-874__st | hsa-mir-874 | 8.62E−05 | 17.8127 |
| hsa-miR-1246__st | hsa-mir-1246 | 3.39E−06 | 17.7516 |
| hsa-miR-195-star__st | hsa-mir-195 | 3.27E−05 | 15.4636 |
| hsa-miR-1290__st | hsa-mir-1290 | 4.81E−05 | 15.3229 |
| hsa-miR-920__st | hsa-mir-920 | 7.50E−05 | 12.6116 |
| hsa-miR-1202__st | hsa-mir-1202 | 3.25E−05 | 12.5472 |
| hsa-miR-135a-star__st | hsa-mir-135a-2 // hsa-mir-135a-1 | 9.27E−05 | 11.7042 |
| hsa-miR-494__st | hsa-mir-494 | 9.13E−05 | 11.1061 |
| hsa-miR-663__st | hsa-mir-663 | 1.94E−07 | 10.8396 |
| hsa-miR-665__st | hsa-mir-665 | 4.57E−05 | 10.3746 |
| hsa-miR-638__st | hsa-mir-638 | 2.59E−05 | 10.1198 |
| hsa-miR-939__st | hsa-mir-939 | 6.23E−05 | 10.068 |
| hsa-miR-923__st | hsa-mir-923 | 6.78E−07 | 9.24476 |
| hsa-miR-1207-5p__st | hsa-mir-1207 | 0.000148 | 8.13818 |
| hsa-miR-346__st | hsa-mir-346 | 0.000246 | 5.91361 |
| hsa-miR-1268__st | hsa-mir-1268 | 0.000433 | 5.23168 |
| hsa-miR-1308__st | hsa-mir-1308 | 1.20E−05 | 3.7476 |
| hsa-miR-563__st | hsa-mir-563 | 0.000297 | 3.49676 |
| hsa-miR-555__st | hsa-mir-555 | 8.85E−05 | 3.32992 |
| hsa-miR-1231__st | hsa-mir-1231 | 0.000275 | 2.64968 |
| hsa-miR-339-5p__st | hsa-mir-339 | 0.000178 | −2.9755 |
| hsa-miR-193a-5p__st | hsa-mir-193a | 0.00024 | −3.03975 |
| hsa-miR-28-3p__t | hsa-mir-28 | 9.31E−05 | −3.152 |
| hsa-miR-125a-5p__st | hsa-mir-125a | 0.000111 | −3.55086 |
| hsa-miR-935__st | hsa-mir-935 | 2.90E−05 | −6.22801 |

TABLE 8

Differentially expressed miRNAs in A375 exosomes versus HEMa-LP exosomes

| Probeset ID | Transcript ID | p-value | Fold change |
|---|---|---|---|
| hsa-miR-1228-star__st | hsa-mir-1228 | 1.55E−06 | 505.036 |
| hsa-miR-1207-5p__st | hsa-mir-1207 | 2.59E−06 | 350.885 |
| hsa-miR-1246__st | hsa-mir-1246 | 3.17E−07 | 291.088 |
| hsa-miR-1268__st | hsa-mir-1268 | 3.48E−06 | 234.973 |
| hsa-miR-320d__st | hsa-mir-320d-1 // hsa-mir-320d-2 | 4.70E−06 | 190.473 |
| hsa-miR-106b__st | hsa-mir-106b | 2.51E−08 | 171.728 |
| hsa-miR-92b-star__st | hsa-mir-92b | 2.70E−05 | 166.596 |
| hsa-miR-18a__st | hsa-mir-18a | 3.74E−08 | 125.793 |
| hsa-miR-1225-5p__st | hsa-mir-1225 | 6.53E−05 | 118.907 |

TABLE 8-continued

Differentially expressed miRNAs in A375 exosomes versus HEMa-LP exosomes

| Probeset ID | Transcript ID | p-value | Fold change |
|---|---|---|---|
| hsa-miR-574-5p__st | hsa-mir-574 | 0.000230898 | 83.9087 |
| hsa-miR-1275__st | hsa-mir-1275 | 6.73E−06 | 80.5778 |
| hsa-miR-31__st | hsa-mir-31 | 2.91E−08 | 79.5696 |
| hsa-miR-19b__st | hsa-mir-19b-1 // hsa-mir-19b-2 | 1.59E−05 | 72.2847 |
| hsa-miR-1300__st | hsa-mir-1300 | 0.000229558 | 72.2301 |
| hsa-miR-939__st | hsa-mir-939 | 8.71E−06 | 68.3327 |
| hsa-miR-663__st | hsa-mir-663 | 3.15E−08 | 66.9031 |
| hsa-miR-483-5p__st | hsa-mir-483 | 0.000181898 | 65.3621 |
| hsa-miR-149-star__st | hsa-mir-149 | 0.000108949 | 63.2017 |
| hsa-let-7c__st | hsa-let-7c | 7.27E−08 | 61.0263 |
| hsa-miR-140-3p__st | hsa-mir-140 | 1.80E−08 | 55.0637 |
| hsa-miR-25-star__st | hsa-mir-25 | 3.68E−05 | 54.4529 |
| hsa-miR-1224-5p__st | hsa-mir-1224 | 0.000118885 | 53.8878 |
| hsa-miR-138__st | hsa-mir-138-2 // hsa-mir-138-1 | 5.88E−07 | 51.1915 |
| hsa-miR-20a__st | hsa-mir-20a | 1.67E−07 | 50.9196 |
| hsa-miR-885-3p__st | hsa-mir-885 | 0.000330485 | 50.1928 |
| hsa-miR-100__st | hsa-mir-100 | 1.47E−08 | 49.0119 |
| hsa-miR-125b__st | hsa-mir-125b-1 // hsa-mir-125b-2 | 1.66E−06 | 43.9443 |
| hsa-miR-671-5p__st | hsa-mir-671 | 8.02E−05 | 42.4832 |
| hsa-miR-23a-star__st | hsa-mir-23a | 1.00E−05 | 41.3584 |
| hsa-miR-130a__st | hsa-mir-130a | 1.04E−06 | 39.3173 |
| hsa-miR-1826__st | hsa-mir-1826 | 8.06E−06 | 38.1896 |
| hsa-miR-516b__st | hsa-mir-516b-2 // hsa-mir-516b-1 | 7.30E−05 | 36.6498 |
| hsa-miR-1202__st | hsa-mir-1202 | 1.65E−05 | 35.0684 |
| hsa-miR-34a__st | hsa-mir-34a | 3.46E−06 | 34.0248 |
| hsa-miR-17-star__st | hsa-mir-17 | 0.000463554 | 33.1164 |
| hsa-miR-744__st | hsa-mir-744 | 4.12E−07 | 33.102 |
| hsa-miR-638__st | hsa-mir-638 | 9.39E−06 | 32.5748 |
| hsa-miR-182__st | hsa-mir-182 | 3.78E−07 | 30.4335 |
| hsa-miR-151-3p__st | hsa-mir-151 | 9.55E−05 | 29.602 |
| hsa-miR-125b-1-star__st | hsa-mir-125b-1 // hsa-mir-125b-2 | 0.000180706 | 28.2338 |
| hsa-miR-575__st | hsa-mir-575 | 0.00013777 | 28.1233 |
| hsa-miR-30d__st | hsa-mir-30d | 8.60E−06 | 27.9004 |
| hsa-miR-423-5p__st | hsa-mir-423 | 2.80E−05 | 26.9011 |
| hsa-miR-297__st | hsa-mir-297 | 9.36E−05 | 26.8554 |
| hsa-miR-1290__st | hsa-mir-1290 | 5.63E−05 | 25.465 |
| hsa-miR-874__st | hsa-mir-874 | 0.000131947 | 25.2651 |
| hsa-miR-936__st | hsa-mir-936 | 0.000474295 | 24.1406 |
| hsa-miR-658__st | hsa-mir-658 | 0.000765788 | 24.0177 |
| hsa-miR-584__st | hsa-mir-584 | 2.17E−07 | 23.4809 |
| hsa-miR-920__st | hsa-mir-920 | 7.50E−05 | 22.3056 |
| hsa-miR-675__st | hsa-mir-675 | 5.00E−05 | 21.5369 |
| hsa-miR-494__st | hsa-mir-494 | 7.95E−05 | 20.784 |
| hsa-miR-18b__st | hsa-mir-18b | 0.000232157 | 19.0607 |
| hsa-miR-196a__st | hsa-mir-196a-2 // hsa-mir-196a-1 | 0.000363491 | 18.635 |
| hsa-miR-99a__st | hsa-mir-9a | 8.93E−06 | 18.5486 |
| hsa-miR-422a__st | hsa-mir-422a | 1.91E−05 | 17.8381 |
| hsa-miR-21__at | hsa-mir-21 | 0.000775614 | 17.2606 |
| hsa-miR-378__st | hsa-mir-378 | 2.21E−06 | 16.2888 |
| hsa-miR-30a__st | hsa-mir-30a | 0.000313186 | 16.2258 |
| hsa-miR-125a-3p__st | hsa-mir-125a | 0.000113581 | 16.1671 |
| hsa-miR-1226-star__st | hsa-mir-1226 | 0.000847071 | 16.1019 |
| hsa-miR-135a-star__st | hsa-mir-135a-2 // hsa-mir-135a-1 | 0.000142887 | 15.7096 |
| hsa-miR-130b__st | hsa-mir-130b | 4.63E−06 | 15.2999 |
| hsa-miR-498__st | hsa-mir-498 | 8.43E−06 | 14.7746 |
| hsa-miR-324-3p__st | hsa-mir-324 | 1.29E−05 | 14.3844 |
| hsa-miR-30b-star__st | hsa-mir-30b | 0.00170916 | 14.3131 |
| hsa-miR-92a-1-star__st | hsa-mir-92a-1 // hsa-mir-92a-2 | 0.00121319 | 14.1813 |
| hsa-miR-22__st | hsa-mir-22 | 3.09E−07 | 14.1611 |
| hsa-miR-210__st | hsa-mir-210 | 0.000164975 | 14.0979 |
| hsa-miR-652__st | hsa-mir-652 | 1.38E−05 | 14.0021 |
| hsa-let-7g__st | hsa-let-7g | 0.00176958 | 13.9158 |
| hsa-miR-15a__st | hsa-mir-15a | 0.000787008 | 13.5709 |
| hsa-miR-152__st | hsa-mir-152 | 3.22E−06 | 13.3912 |
| hsa-miR-140-5p__st | hsa-mir-140 | 1.83E−05 | 13.3794 |
| hsa-miR-512-3p__st | hsa-mir-512-1 // hsa-mir-512-2 | 0.00111791 | 13.1842 |
| hsa-miR-629__st | hsa-mir-629 | 0.000343276 | 12.5262 |
| hsa-miR-877__st | hsa-mir-877 | 8.96E−05 | 12.2348 |
| hsa-miR-886-5p__st | hsa-mir-886 | 7.54E−07 | 11.9645 |
| hsa-miR-20b__st | hsa-mir-20b | 1.29E−06 | 11.6251 |
| hsa-miR-532-5p__st | hsa-mir-532 | 5.01E−08 | 10.9735 |
| hsa-miR-222__st | hsa-mir-222 | 1.59E−09 | 10.6388 |
| hsa-miR-27a-star__st | hsa-mir-27a | 0.0016846 | 10.301 |
| hsa-miR-1323__st | hsa-mir-1323 | 0.000238 | 9.87272 |
| hsa-miR-519b-5p__st | hsa-mir-519b | 0.00130342 | 9.82561 |
| hsa-miR-324-5p__st | hsa-mir-324 | 1.62E−05 | 9.6257 |
| hsa-miR-425__st | hsa-mir-425 | 1.72E−05 | 9.35747 |
| hsa-miR-181b__st | hsa-mir-181b-1 // hsa-mir-181b-2 | 1.03E−05 | 8.80305 |
| hsa-miR-199b-3p__st | hsa-mir-199b | 0.000800773 | 8.67688 |
| hsa-miR-423-3p__st | hsa-mir-423 | 9.66E−06 | 8.58766 |
| hsa-miR-193b-star__st | hsa-mir-193b | 0.000462364 | 8.55467 |
| hsa-let-7a__st | hsa-let-7a-2 // hsa-let-7a-3 // hsa-let-7a-1 | 2.45E−05 | 8.42611 |
| hsa-miR-424-star__st | hsa-mir-424 | 0.000157474 | 8.23534 |
| hsa-miR-502-3p__rt | hsa-mir-502 | 7.66E−05 | 7.46927 |
| hsa-miR-30c-2-star__st | hsa-mir-30c-1 // hsa-mir-30c-2 | 0.000280572 | 7.44762 |
| hsa-miR-1231__st | hsa-mir-1231 | 2.43E−05 | 7.16585 |
| hsa-miR-221__st | hsa-mir-221 | 1.29E−07 | 7.1091 |
| hsa-miR-29a__st | hsa-mir-29a | 2.17E−05 | 7.03373 |
| hsa-miR-1307__st | hsa-mir-1307 | 0.000295605 | 6.6647 |
| hsa-miR-660__st | hsa-mir-660 | 0.000489615 | 6.59606 |
| hsa-miR-320c__st | hsa-mir-320c-1 // hsa-mir-320c-2 | 6.38E−06 | 6.42105 |
| hsa-miR-193a-5p__st | hsa-mir-193a | 5.59E−05 | 6.30261 |
| hsa-miR-665__st | hsa-mir-665 | 0.000413014 | 6.12525 |
| hsa-miR-25__st | hsa-mir-25 | 1.02E−05 | 6.08933 |
| hsa-miR-27a__st | hsa-mir-27a | 1.77E−06 | 5.90604 |
| hsa-miR-500-star__st | hsa-mir-500 | 0.000804433 | 5.68279 |
| hsa-miR-523-star__st | hsa-mir-523 | 0.000948735 | 5.54336 |
| hsa-miR-15b__st | hsa-mir-15b | 4.82E−06 | 5.29454 |
| hsa-miR-1180__st | hsa-mir-1180 | 0.000833146 | 4.74018 |
| hsa-miR-28-5p__st | hsa-mir-28 | 0.000639848 | 4.57202 |
| hsa-miR-94s0__st | hsa-mir-940 | 0.00178096 | 4.56052 |
| hsa-miR-106a__st | hsa-mir-106a | 8.16E−06 | 4.43263 |
| hsa-miR-28-3p__st | hsa-mir-28 | 7.20E−05 | 4.4045 |
| hsa-miR-151-5p__st | hsa-mir-151 | 2.32E−06 | 4.30919 |
| hsa-miR-191-star__st | hsa-mir-191 | 0.000678889 | 4.09067 |
| hsa-miR-181a__st | hsa-mir-181a-1 // hsa-mir-181a-2 | 2.30E−06 | 4.0121 |
| hsa-miR-1308__st | hsa-mir-1308 | 2.60E−05 | 3.98399 |
| hsa-miR-106b-star__st | hsa-mir-106b | 0.000235592 | 3.76911 |
| hsa-miR-16__st | hsa-mir-16-1 // hsa-mir-16-2 | 2.22E−08 | 3.72143 |
| hsa-miR-92a__st | hsa-mir-92a-1 // hsa-mir-92a-2 | 2.25E−05 | 3.68391 |
| hsa-miR-620__st | hsa-mir-620 | 0.000159954 | 3.58654 |
| hsa-miR-27b__St | hsa-mir-27b | 0.000937003 | 3.48137 |
| hsa-miR-601__st | hsa-mir-601 | 0.000416147 | 3.32931 |
| hsa-miR-17__st | hsa-mir-17 | 8.00E−05 | 3.29328 |
| hsa-miR-98__st | hsa-mir-98 | 0.0006643 | 3.02189 |
| hsa-miR-330-3p__st | hsa-mir-330 | 0.000508667 | 2.9645 |
| hsa-miR-1301__st | hsa-mir-1301 | 0.000145987 | 2.84978 |
| hsa-miR-125a-5p__st | hsa-mir-125a | 0.000861431 | 2.73428 |
| hsa-miR-923__st | hsa-mir-923 | 9.71E−05 | 2.70408 |
| hsa-miR-93__st | hsa-mir-93 | 0.000332297 | 2.67258 |
| hsa-miR-208a__st | hsa-mir-208a | 0.00100027 | 2.15041 |
| hsa-miR-200b__st | hsa-mir-200b | 0.000735376 | −2.35632 |
| hsa-miR-23b__st | hsa-mir-23b | 0.000145511 | −2.46459 |
| hsa-miR-146a__st | hsa-mir-146a | 8.76E−05 | −2.69393 |
| hsa-miR-433__st | hsa-mir-433 | 0.000797291 | −2.97062 |
| hsa-let-7d__st | hsa-let-7d | 2.71E−05 | −3.00489 |
| hsa-miR-186__st | hsa-mir-186 | 0.0018126 | −3.31305 |
| hsa-miR-429__st | hsa-mir-429 | 0.00153772 | −3.38207 |
| hsa-miR-136-star__st | hsa-mir-136 | 0.000960818 | −4.22928 |
| hsa-miR-302f__st | hsa-mir-302f | 0.001394 | −4.25339 |

TABLE 8-continued

Differentially expressed miRNAs in A375 exosomes versus HEMa-LP exosomes

| Probeset ID | Transcript ID | p-value | Fold change |
|---|---|---|---|
| hsa-miR-376a-star__st | hsa-mir-376a-2 // hsa-mir-376a-1 | 0.00129308 | −4.76854 |
| hsa-miR-74-star__st | hsa-mir-7-2 // hsa-mir-7-3 // hsa-mir-7-1 | 0.000885861 | −5.7772 |
| hsa-miR-646__st | hsa-mir-646 | 0.000680921 | −5.97694 |
| hsa-miR-511__st | hsa-mir-511-1 // hsa-mir-511-2 | 0.000104729 | −6.19338 |
| hsa-miR-551a__st | hsa-mir-551a | 0.000355265 | −6.23238 |
| hsa-miR-1282__st | hsa-mir-1282 | 0.000419911 | −6.52095 |
| hsa-miR-340-star__st | hsa-mir-340 | 0.00105972 | −6.86451 |
| hsa-miR-550-star__st | hsa-mir-550-1 // hsa-mir-550-2 | 0.000947093 | −6.88596 |
| hsa-miR-1184__st | hsa-mir-1184 // hsa-mir-1184 // hsa-mir-1184 | 0.000702152 | −7.12768 |
| hsa-miR-598__st | hsa-mir-598 | 0.0015775 | −7.24971 |
| hsa-miR-548d-3p__st | hsa-mir-548d-2 // hsa-mir-548d-1 | 4.36E−05 | −7.27992 |
| hsa-miR-1207-3p__st | hsa-mir-1207 | 0.000769104 | −8.02748 |
| hsa-miR-589__st | hsa-mir-589 | 0.000239178 | −8.03378 |
| hsa-miR-518d-3p__st | hsa-mir-518d | 0.000647638 | −8.17986 |
| hsa-miR-892b__st | hsa-mir-892b | 0.00143163 | −8.44038 |
| hsa-miR-345__st | hsa-mir-345 | 8.66E−08 | −8.52211 |
| hsa-miR-1281__st | hsa-mir-1281 | 0.000407935 | −8.52596 |
| hsa-miR-431__st | hsa-mir-431 | 0.00127159 | −8.55391 |
| hsa-miR-148a-star__st | hsa-mir-148a | 0.00120094 | −8.60528 |
| hsa-miR-30c__st | hsa-mir-30c-1 // hsa-mir-30c-2 | 5.21E−05 | −8.7249 |
| hsa-miR-181a-2-star__st | hsa-mir-181a-1 // hsa-mir-181a-2 | 8.22E−06 | −8.84383 |
| hsa-miR-182-star__st | hsa-mir-182 | 0.000294902 | −8.91097 |
| hsa-miR-499-3p__st | hsa-mir-499 | 0.000430822 | −9.46698 |
| hsa-miR-219-5p__st | hsa-mir-219-1 // hsa-mir-219-2 | 0.000261388 | −9.9485 |
| hsa-miR-770-5p__st | hsa-mir-770 | 0.001502 | −10.0632 |
| hsa-miR-603__st | hsa-mir-603 | 0.00102662 | −10.7806 |
| hsa-miR-1296__st | hsa-mir-1296 | 0.000220099 | −11.0339 |
| hsa-miR-1279__st | hsa-mir-1279 | 0.000457544 | −11.2268 |
| hsa-miR-299-5p__st | hsa-mir-299 | 0.00028146 | −13.8065 |
| hsa-miR-337-3p__st | hsa-mir-337 | 0.000542528 | −14.5948 |
| hsa-miR-631__st | hsa-mir-631 | 0.0015868 | −15.7695 |
| hsa-miR-431-star__st | hsa-mir-431 | 0.00110193 | −16.4517 |
| hsa-miR-30b__st | hsa-mir-30b | 0.000803366 | −16.8321 |
| hsa-miR-613__st | hsa-mir-613 | 0.000731338 | −18.1017 |
| hsa-miR-614__st | hsa-mir-614 | 0.000632223 | −18.2974 |
| hsa-miR-657__st | hsa-mir-457 | 8.23E−05 | −18.7241 |
| hsa-miR-205__st | hsa-mir-205 | 0.00138379 | −18.9218 |
| hsa-miR-197__st | hsa-mir-197 | 1.41E−05 | −20.2304 |
| hsa-miR-574-3p__st | hsa-mir-574 | 1.99E−05 | −20.2365 |
| hsa-miR-378-star__st | hsa-mir-378 | 3.62E−05 | −22.2091 |
| hsa-miR-605__st | hsa-mir-605 | 2.83E−05 | −22.2354 |
| hsa-miR-218-2-stat__st | hsa-mir-218-1 // hsa-mir-218-2 | 0.000505579 | −22.4836 |
| hsa-miR-1200__st | hsa-mir-1200 | 4.40E−05 | −24.0724 |
| hsa-miR-199a-5p__st | hsa-mir-199a-1 // hsa-mir-199a-2 | 0.000281009 | −24.2237 |
| hsa-miR-885-5p__st | hsa-mir-885 | 0.000103042 | −25.5669 |
| hsa-miR-618__st | hsa-mir-618 | 0.000286278 | −26.1404 |
| hsa-miR-609__st | hsa-mir-609 | 3.74E−05 | −27.927 |
| hsa-miR-576-5p__st | hsa-mir-576 | 0.00015573 | −28.0799 |
| hsa-miR-335-star__st | hsa-mir-335 | 0.00142341 | −28.9084 |
| hsa-miR-33a-star__st | hsa-mir-33a | 0.000254151 | −29.8004 |
| hsa-miR-504__st | hsa-mir-504 | 0.000463793 | −31.1698 |
| hsa-miR-218-1-stat__st | hsa-mir-218-1 // hsa-mir-218-2 | 0.00076827 | −32.6357 |
| hsa-let-7f-2-star__st | hsa-let-7f-1 // hsa-let-7f-2 | 2.68E−05 | −34.575 |
| hsa-miR-302e__st | hsa-mir-302e | 9.49E−06 | −38.0075 |
| hsa-miR-668__st | hsa-mir-668 | 0.000659835 | −38.4515 |
| hsa-miR-935__st | hsa-mir-935 | 2.58E−06 | −38.746 |
| hsa-let-7g-star__st | hsa-let-7g | 0.0013729 | −39.2665 |
| hsa-miR-597__st | hsa-mir-597 | 0.000753708 | −40.9511 |
| hsa-miR-640__st | hsa-mir-640 | 0.00150222 | −42.7494 |
| hsa-miR-1284__st | hsa-mir-1284 | 0.000293852 | −44.0038 |
| hsa-miR-671-3p__st | hsa-mir-671 | 0.000619384 | −44.4936 |
| hsa-miR-138-1-star__st | hsa-mir-138-2 // hsa-mir-138-1 | 7.97E−06 | −47.3233 |
| hsa-miR-29c-star__st | hsa-mir-29c | 1.50E−05 | −51.8072 |
| hsa-miR-509-3p__st | hsa-mir-509-2 // hsa-mir-509-3 // hsa-mir-509-1 | 2.81E−06 | −51.9599 |
| hsa-miR-149__st | hsa-mir-149 | 1.98E−05 | −67.5136 |
| hsa-miR-220a__st | hsa-mir-220a | 0.000119621 | −69.8681 |
| hsa-let-7e-star__st | hsa-let-7e | 3.94E−05 | −74.8668 |
| hsa-miR-212__st | hsa-mir-212 | 0.000565766 | −75.2433 |
| hsa-miR-432-star__st | hsa-mir-432 | 0.000128676 | −85.8363 |
| hsa-miR-34c-3p__st | hsa-mir-34c | 6.57E−05 | −90.7391 |
| hsa-miR-214-star__st | hsa-mir-214 | 5.98E−06 | −95.3038 |
| hsa-miR-1229__st | hsa-mir-1229 | 0.000806139 | −108.761 |
| hsa-miR-758__st | hsa-mir-758 | 9.19E−05 | −120.233 |
| hsa-let-7b-star__st | hsa-let-7b | 1.57E−05 | −123.021 |
| hsa-let-7d-star__st | hsa-let-7d | 0.0010806 | −141.371 |
| hsa-miR-654-3p__st | hsa-mir-654 | 4.31E−05 | −144.764 |
| hsa-miR-130b-star__st | hsa-mir-130b | 9.98E−06 | −149.159 |
| hsa-miR-185-star__st | hsa-mir-185 | 0.00117822 | −159.808 |
| hsa-miR-483-3p__st | hsa-mir-483 | 0.000642504 | −162.386 |
| hsa-miR-1178__st | hsa-mir-1178 | 2.05E−06 | −174.264 |
| hsa-miR-26b-star__st | hsa-mir-26b | 0.000412254 | −190.45 |
| hsa-miR-411-stat__st | hsa-mir-411 | 7.74E−06 | −208.439 |
| hsa-miR-211__st | hsa-mir-211 | 2.49E−05 | −213.089 |
| hsa-miR-485-3p__st | hsa-mir-485 | 1.53E−05 | −215.4 |
| hsa-miR-412__st | hsa-mir-412 | 0.000154358 | −245.148 |
| hsa-miR-744-star__st | hsa-mir-744 | 1.96E−05 | −288.359 |
| hsa-miR-34b__st | hsa-mir-34b | 7.95E−05 | −322.916 |
| hsa-miR-937__st | hsa-mir-937 | 1.44E−06 | −366.943 |
| hsa-miR-647__st | hsa-mir-647 | 0.00020118 | −505.16 |

Discussion

In the present study, the present inventors first investigated the mRNA signatures of melanoma cells and their exosomes and compared these signatures with those of normal melanocytes and their exosomes. The present inventors found large numbers of differentially expressed mRNAs in melanocytes compared with melanocyte-derived exosomes, and in melanoma cells compared with melanoma-derived exosomes. This is consistent with previous findings in glioblastoma microvesicles and their donor cells [14]. Exosomal mRNAs may transfer or shuttle signals between cells, and may contribute to important biological functions in normal cells, as well as malignant transformation in tumor cells [14, 15].

One interesting aspect of the findings was that when the present inventors examined the correlation of mRNA expression in cells compared with their exosomes, the present inventors noticed that melanoma cell-derived exosomes have a closer relationship with their originating melanoma cells than normal melanocyte-derived exosomes did with their originating non-cancer cells. This suggests that cancer-derived exosome mRNA profiles may more closely reflect mRNA profiles in cancer cells themselves, which would imply the potential of using exosomes as a biomarker for melanoma. By comparing mRNA profiles in melanoma exosomes with normal melanocyte-derived exosomes, the present inventors found that even though there are various biological processes and ontologies of those differentially expressed exosome mRNAs, many are linked to the advancement of melanoma. Indeed, several studies have shown that tumor exosomes have the ability to transport RNAs to promote tumor growth [14]. This finding also suggests the potential of using exosome profiles as biomarkers not only of the presence of disease, but also disease progression and response to therapy.

The present inventors then investigated miRNA signatures in melanoma cells and their exosomes and compared these signatures with those from normal melanocytes and their exosomes using miRNA arrays. The present inventors discovered that there are some differentially expressed miRNAs in melanocytes compared with melanocyte-derived exosomes, and also between melanoma cells compared with melanoma-derived exosomes. The present inventors also determined that many of these miRNA have important functions in cellular growth and proliferation, cellular development, cellular movement, and cell death. The findings confirm earlier studies showing that miRNAs in exosomes have important biological functions [14-17]. An important finding from the study came from looking at the correlation of miRNA expression in cells compared with exosomes. Both melanoma cell-derived and normal melanocyte-derived exosomes miRNA profiles were strongly correlated with their originating cells. However, there was much weaker correlation between miRNA expression in melanoma exosomes compared with miRNA expression in normal melanocyte-derived exosomes. This strongly suggests that there are distinctive miRNA profiles between melanoma exosomes and normal melanocyte exosomes, which confirms the rationale behind many of the current studies investigating the usefulness of exosomal miRNA as tumor biomarkers in diseases, such as lung cancer and ovarian cancer [9, 18]. The data show that differential expression of exosomal miRNA is more focused than mRNA expression. Furthermore, when the present inventors looked at the regression analysis of mRNA signals and miRNA signals between A375 and HEMa-LP exosomes, the present inventors showed that the difference of miRNA signals between A375 and HEMa-LP exosomes is much larger than that of mRNA signals. It is likely that this would be another advantage of using exosomal miRNA signatures in biomarker studies, instead of sophisticated and unbalanced mRNA data.

Through the proteomic approach, the present inventors identified exosomal proteins that are known to be associated with cell adhesion, migration, and invasion in melanoma. Some of these proteins have been identified by other researchers in similar studies. For example, Mears et al. compared the protein profiles of two melanoma cell lines, MeWo and SK-MEL-28 cells, with their exosomes [36]. They discovered several novel melanoma exosomal proteins, such as p120 catenin, radixin, and immunoglobulin superfamily member 8 (PGRL). Among the list of exosomal proteins they identified were syntenin 1 and annexin A2, which are also on the list of identified differentially expressed exosomal protein [36]. Although most reports have determined that syntenin-1 enhances melanoma cell migration, invasion and metastasis [37, 38], several discrepant findings have been observed about the role of syntenin-1 depending on the specific cellular environment investigated [39]. In the study, the present inventors observed that syntenin-1 protein expression was reduced in melanoma exosomes compared to normal melanocyte-derived exosomes. This is in line with findings in a B16 mouse melanoma model that show syntenin-1 has lower expression levels in melanoma secretomes, but cells exhibit a greater capacity for cell invasion [23].

Annexin A1 has also been shown to amplify the ability of cells to become invasive and to enhance melanoma dissemination [40]. It is a key regulator of pathological angiogenesis and physiological angiogenic balance [34]. Similarly, annexin A2 is upregulated in various tumors and has been shown to play multiple roles in regulating cellular function, including angiogenesis, proliferation, apoptosis, cell migration, invasion and adhesion [31]. In the study, the present inventors found that protein expression levels of annexin A1 were upregulated, whereas annexin A2 levels were downregulated in A375 melanoma exosomes. Grewal and Enrich have summarized the differences in various isoforms of annexin protein expression patterns, subcellular localization and mode of action. They suggest that annexins are likely to differentially contribute and cooperate in fine-tuning of the activity of epidermal growth factor receptor (EGFR), thus regulate the growth of a variety of tumor cells [41].

The study also revealed several novel proteins differentially expressed in exosomes that have not previously been identified in this context. The protein with the greatest differential expression in melanoma exosomes is hyaluronan and proteoglycan link protein 1 (HAPLN1). HAPLN1 is an extracellular matrix mucopolysaccharide that has been previously shown to promote metastasis in cancer cells, including B16F10 melanoma [42, 43]. HAPLN1 is also involved in melanoma development and extracellular matrix remodeling during the process of melanoma cell migration and melanoma progression [35, 44]. Further research investigating the role of HAPLN1 in exosomes may uncover novel mechanisms to explain potential roles for exosomes in melanoma progression. Additionally, HAPLN1 may also prove to be important clinically, as it is a specific exosomal protein that could be the focus of future melanoma biomarker studies.

Some differentially expressed exosomal proteins have already been explored as potential biomarkers in melanoma patients [1]. For example, Logozzi et al. designed an in-house sandwich ELISA (Exotest) and found that plasma exosomes expressing CD63 or caveolin-1 were significantly increased in melanoma patients compared to healthy donors. They further determined that the number of caveolin-1 positive plasma exosomes was significantly greater than the number of CD63 positive exosomes in melanoma patients [1]. Since then, CD63 has become commonly accepted as an exosome marker.

The present inventors are aware that studies such as ours that examine exosomal mRNA, miRNA, and protein profiles produce large amounts of data. Indeed, the mRNA expression profile resulted in identification of thousands of disparate differentially expressed genes. However, the present inventors were able to focus this information better when combining miRNA and protein profiles. Proteins are the end-point molecules that execute biological functions after undergoing several sophisticated genetic processes, including transcription, translation and post-translational/post-transcriptional modifications. The findings suggest that combining miRNA and protein profiles is a superior approach to identify future exosomal biomarker of disease. One example of how the data can be combined to provide potential new avenues of mechanistic melanoma research and biomarker studies is to look at interactions of highly differentially expressed proteins and miRNAs. In the study, HAPLN1, hsa-miR-23, and hsa-miR-21 were the three molecules at the top of the differentially expressed lists. TargetScan identified that HAPLN1 is targeted by hsa-miR-23, but HAPLN1 can also trigger upregulation of miR-21, which was previously shown to serve an essential role in the malignant progression of human gliomas [47]. Identifying how these three molecules interact in melanoma to contribute to metastasis and disease progression could potentially reveal new avenues of targeted therapy or biomarkers useful in diagnosis and prognosis.

Another novel finding of the study is that normal melanocytes can acquire invasiveness through the internalization of melanoma exosomes. The data suggest that mRNA and miRNA within melanoma exosomes may be actively transported into normal melanocytes and induce normal melanocyte invasion ability. Pre-treatment of melanoma exosomes with DNase and RNase A didn't affect the invasion ability of normal melanocytes rendered by melanoma exosome transfer. This excludes the possibility that DNA or RNA molecules in the cell supernatant might mediate this induced normal melanocyte invasion ability. It is exosome transportation that confers normal melanocytes' invasion ability. Pre-treatment of Protease K abolished the normal melanocytes' invasion ability rendered by the melanoma exosomes. The reason might be that Protease K disrupt the exosome membrane structure and affect the exosome transmission. A protein synthesis inhibitor was also able to inhibit normal melanocytes' invasion ability acquired through uptake of melanoma exosomes. This further suggests that the whole process of exosome uptake, molecule transmission, and promotion of invasion requires new protein synthesis.

Although it seems unlikely that circulating exosomes impart a malignant phenotype to normal melanocytes in vivo, it demonstrates the principle that potent intercellular signaling via melanoma exosomes may alter disease progression and metastatic potential. The findings are in accordance with results from other researchers showing that exosomes can transport RNA and proteins to other cells in order to promote tumor growth [14]. Exosomes released from melanoma cells can also prepare sentinel lymph nodes for tumor metastasis [48]. The present inventors attempted to use cytochalasin D to inhibit exosome uptake by HEMa-LP cells to further study the underlying mechanisms; however, cytochalasin D is toxic to the HEMa-LP cells (data not shown). This prevented obtaining useful data. Detailed mechanistic studies may clarify how the uptake of exosomes contributes to melanoma progression.

The present inventors also compared the method of combination of ultrafiltration and ultracentrifugation with another exosome isolation method, Exoquick-TC precipitation, to assess whether there were differences in the ability of the exosomes to induce migration/invasion. Exosomes isolated by Exoquick-TC precipitation were not able to affect the normal melanocyte invasion ability. The reason for a discrepancy between the effects of exosomes isolated by different methods might be that Exoquick-TC precipitation couldn't enrich enough exosomes. Indeed, the present inventors observed that sufficient exosomes are essential for the effective enhancement of normal melanocyte invasion ability (unpublished data).

The present inventors expected that after exosomes are taken up by normal melanocytes, those highly expressed genes in melanoma exosomes might also then be highly expressed in normal melanocytes. However, when assessing the gene expression changes of normal melanocyte after the uptake of melanoma cell-derived exosomes, the present inventors found minimal differential expression of those genes that were highly expressed in melanoma exosomes. The present inventors have considered two possible explanations for this finding. One is that, even though the invasive melanocytes significantly increased compared with control melanocytes, the portion of invasive melanocytes were a small part of the total melanocytes (about 10%, FIG. 8C).

The other reason is that after exosomes transfer into melanocytes, there were multiple cellular processes and signal pathways that would need to act cooperatively in order to alter cellular gene expression to reflect the original highly expressed genes in melanoma exosomes. The best approach to identify the differentially expressed genes in normal melanocytes after the uptake of exosomes would be through microarray screening.

Throughout this document, various references are mentioned. All such references are incorporated herein by reference, including the references set forth in the following list:

REFERENCES

1. Simpson R J, Lim J W, Moritz R L, Mathivanan S (2009) Exosomes: proteomic insights and diagnostic potential. Expert Rev Proteomics 6: 267-283.
2. Pan B T and Johnstone R M (1983) Fate of the transferrin receptor during maturation of sheep reticulocytes in vitro: Selective externalization of the receptor. Cell 33: 967-978.
3. Thery C, Regnault A, Garin J, Wolfers J, Zitvogel L, et al. (1999) Molecular characterization of dendritic cell-derived exosomes: selective accumulation of the heat shock protein hsc73. J Cell Biol 147: 599-610.
4. Raposo G, Nijman H W, Stoorvogel W, Liejendekker R, Harding C V, et al. (1996) B lymphocytes secrete antigen-presenting vesicles. J Exp Med 183: 1161-1172.
5. Blanchard N, Lankar D, Faure F, Regnault A, Dumont C, et al. (2002) TCR activation of human T cells induces the production of exosomes bearing the TCR/CD3/ζ complex. J Immunol 168: 3235-3241
6. Raposo G. Tenza D, Mecheri S, Peronet R, Bonnerot C, et al. (1997) Accumulation of major histocompatibility complex class II molecules in mast cell secretory granules and their release upon degranulation. Mol Biol Cell 8: 2631-2645
7. Van Niel G, Raposo G, Candalh C, Boussac M, Hershberg R, et al. (2001) Intestinal epithelial cells secrete exosome-like vesicles. Gastroenterology 121: 337-349
8. Logozzi M, De Milito A, Lugini L, Borghi M, Calabrò L, et al. (2009) High levels of exosomes expressing CD63 and caveolin-1 in plasma of melanoma patients. PLoS One 4:e5219.
9. Rabinowits G, Gercel-Taylor C, Day J M, Taylor D D, et al. (2009) Exosomal microRNA: a diagnostic marker for lung cancer. Clin Lung Cancer 10: 42-46.
10. Pisitkun T, Shen R F, Knepper M A (2004) Identification and proteomic profiling of exosomes in human urine. Proc Natl Acad Sci USA 101: 13368-13373.
11. Michael A, Bajracharya S D, Yuen P S, Zhou H, Star R A, et al. (2009) Exosomes from human saliva as a source of microRNA biomarkers. Oral Dis 16: 34-38.
12. Keller S, Rupp C, Stoeck A, Runz S, Fogel M, et al. (2007) CD24 is a marker of exosomes secreted into urine and amniotic fluid. Kidney Int 72: 1095-1102.
13. Andre F, Schartz N E, Movassagh M, Flament C, Pautier P, et al. (2002) Malignant effusions and immunogenic tumour-derived exosomes. Lancet 360: 295-305.
14. Skog J, Würdinger T, van Rijn S, Meijer D H, Gainche L, et al. (2008) Glioblastoma microvesicles transport RNA and proteins that promote tumour growth and provide diagnostic biomarkers. Nat Cell Biol 10:1470-1476
15. Valadi H, Ekstrom K, Bossios A, Sjostrand M, Lee J J, et al. (2007) Exosome-mediated transfer of mRNAs and microRNAs is a novel mechanism of genetic exchange between cells. Nat Cell Biol 9: 654-659.
16. Sandhu S, Garzon R (2011) Potential applications of microRNAs in cancer diagnosis, prognosis, and treatment. Semin Oncol 38: 781-787.
17. Lee T H, D'Asti E, Magnus N, Al-Nedawi K, Meehan B, et al. (2011) Microvesicles as mediators of intercellular communication in cancer—the emerging science of cellular 'debris'. Semin Immunopathol 33:455-467.
18. Taylor D D, Gercel-Taylor C (2008) MicroRNA signatures of tumor-derived exosomes as diagnostic biomarkers of ovarian cancer. Gynecol Oncol 110:13-21.
19. Atay S, Gercel-Taylor C, Taylor D D (2011) Human trophoblast-derived exosomal fibronectin induces pro-inflammatory Il-1b production by macrophages. Am J Reprod Immunol 66: 259-269.
20. Merchant M L, Powell D W, Wilkey D W, Cummins T D, Deegens J K, et al. (2010) Microfiltration isolation of human urinary exosomes for characterization by M S. Proteomics Clin Appl 4: 84-96.
21. Hao H, Dong Y, Bowling M T, Gomez-Gutierrez J G, Zhou H S, et al. (2007) E2F-1 induces melanoma cell apoptosis via PUMA up-regulation and Bax translocation. BMC Cancer 7: 24
22. Ma X, Piao S, Wang D, McAfee Q W, Nathanson K L, et al. (2011) Measurement of tumor cell autophagy predict invasiveness, resistance to chemotherapy, and survival in melanoma. Clin Cancer Res 17:3478-3489
23. Rondepierre F, Bouchon B, Bonnet M, Moins N, Chezal J M, et al. (2010) B16 melanoma secretomes and in vitro invasiveness: syntenin as an invasion modulator. Melanoma Res 20: 77-84.
24. Lässer C, Alikhani V S, Ekström K, Eldh M, Paredes P T, et al. (2011) Human saliva, plasma and breast milk exosomes contain RNA: uptake by macrophages. J Transl Med 9: 9.
25. Choi H, Ahn S, Chang H, Cho N S, Joo K, et al. (2007) Influence of N-glycan processing disruption on tyrosinase and melanin synthesis in HM3KO melanoma cells. Exp Dermatol 16:110-117.
26. Ogura T, Noguchi T, Murai-Takebe R, Hosooka T, Honma N, et al. (2004) Resistance of B16 melanoma cells to CD47-induced negative regulation of motility as a result of aberrant N-glycosylation of SHPS-1. J Biol Chem 279:13711-13720.
27. Yamauchi Y, Furukawa K, Hamamura K, Furukawa K (2011) Positive feedback loop between PI3K-Akt-mTORC1 signaling and the lipogenic pathway boosts Akt signaling: induction of the lipogenic pathway by a melanoma antigen. Cancer Res 71: 4989-4997.
28. Ryan D, Rafferty M, Hegarty S, O'Leary P, Faller W, et al. (2010) Topoisomerase I amplification in melanoma is associated with more advanced tumors and poor prognosis. Pigment Cell Melanoma Res 23: 542-553.
29. Journe F, Boufker H I, Van Kempen L, Galibert M D, Wiedig M, et al. (2011) TYRP1 mRNA expression in melanoma metastases correlates with clinical outcome. Br J Cancer 105:1726-1732.
30. Ma J and Frank M H (2010) Tumor initiation in human malignant melanoma and potential cancer therapies. Anti-cancer Agents Med Chem 10: 131-136.
31. Lokman N A, Ween M P, Oehler M K, Ricciardelli C (2011) The role of annexin A2 in tumorigenesis and cancer progression. Cancer Microenviron 4:199-208.
32. Greenberg E, Hershkovitz L, Itzhaki O, Hajdu S, Nemlich Y, et al. (2011) Regulation of cancer aggressive features in melanoma cells by microRNAs. PLoS One 6: e18936.
33. Migliore C, Petrelli A, Ghiso E, Corso S, Capparuccia L, et al. (2008) MicroRNAs impair MET-mediated invasive growth. Cancer Res 68:10128-10136.
34. Yi M and Schnitzer J E (2009) Impaired tumor growth, metastasis, angiogenesis and wound healing in annexin A1-null mice. Proc Natl Acad Sci USA 106: 17886-17891
35. Prakash M, Kale S, Ghosh I, Kundu G C, Datta K (2011) Hyaluronan-binding protein 1 (HABP1/p32/gClqR) induces melanoma cell migration and tumor growth by NF-kappa B dependent MMP-2 activation through integrin $\alpha(v)\beta(3)$ interaction. Cell Signal 23:1563-1577.
36. Mears R, Craven R A, Hanrahan S, Totty N, Upton C, et al. (2004) Proteomic analysis of melanoma-derived exosomes by two-dimensional polyacrylamide gel electrophoresis and mass spectrometry. Proteomics 4: 4019-4031
37. Hwangbo C, Kim J, Lee J J, Lee J H (2010) Activation of the integrin effector kinase focal adhesion kinase in cancer cells is regulated by crosstalk between protein kinase Calpha and the PDZ adapter protein mda-9/Syntenin. Cancer Res 70:1645-1655.
38. Boukerche H, Su Z Z, Prévot C, Sarkar D, Fisher P B (2008) mda-9/Syntenin promotes metastasis in human melanoma cells by activating c-Src. Proc Natl Acad Sci USA 105:15914-15919.
39. Sarkar D, Boukerche H, Su Z Z, Fisher P B (2008) mda-9/Syntenin: more than just a simple adapter protein when it comes to cancer metastasis. Cancer Res 68:3087-3093.
40. Rondepierre F, Bouchon B, Papon J, Bonnet-Duquennoy M, Kintossou R, et al. (2009) Proteomic studies of B16 lines: involvement of annexin A1 in melanoma dissemination. Biochim Biophys Acta 1794: 61-69.
41. Grewal T, Enrich C (2009) Annexins—modulators of EGF receptor signalling and trafficking. Cell Signal 21: 847-858
42. Toole B P (2002) Hyaluronan promotes the malignant phenotype. Glycobiology 12: 37R-42R.
43. Mummert M E, Mummert D I, Ellinger L, Takashima A (2003) Functional roles of hyaluronan in B16-F10 melanoma growth and experimental metastasis in mice. Mol Cancer Ther 2: 295-300.
44. Perrotta R, Bevelacqua Y, Malaguarnera G, Paladina I, Giordano M, et al. (2010) Serum markers of cutaneous melanoma. Front Biosci (Elite Ed) 2:1115-1122.
45. Graner M W, Alzate O, Dechkovskaia A M, Keene J D, Sampson J H, et al. (2009) Proteomic and immunologic analyses of brain tumor exosomes. FASEB J 23:1541-1557.
46. Vella L J, Greenwood D L, Cappai R, Scheerlinck J P, Hill A F (2008) Enrichment of prion protein in exosomes derived from ovine cerebral spinal fluid. Vet Immunol Immunopathol 124:385-393.
47. Kwak H J, Kim Y J, Chun K R, Woo Y M, et al. (2011) Downregulation of Spry2 by miR-21 triggers malignancy in human gliomas. Oncogene 30: 2433-2442.
48. Hood J L, San R S, Wickline S A (2011) Exosomes released by melanoma cells prepare sentinel lymph nodes for tumor metastasis. Cancer Res 71: 3792-3801.
49. Iorio M V, Visone R, Di Leva G, Donati V, Petrocca F, Casalini P, et al. MicroRNA signatures in human ovarian cancer. Cancer Res 2007; 67:8699-707.
50. De Cecco L, Marchionni L, Gariboldi M, Reid J F, Lagonigro M S, Caramuta S, et al. Gene expression profiling of advanced ovarian cancer: Characteristization of a molecular signature involving fibroblast growth factor 2. Oncogene 2004; 23:8171-83.
51. Calin G A, Croce C M. MicroRNA-cancer connection: the beginning of a new tale. Cancer Res 2006a; 66:7390-94.
52. Calin G A, Croce C M. MicroRNA signatures in human cancers. Nature Rev Cancer 2006b; 6:857-66.
53. Lu J, Getz G, Miska E A, Alvarez-Saavedra E, Lamb J, Peck D, et al. MicroRNA expression profiles classify human cancers. Nature 2005; 435: 834-8.
54. Taylor D D, Gercel-Taylor C. Tumour-derived exosomes as mediates of T-cell signaling defects. Brit Cancer 2005; 92:305-11.

What is claimed is:

1. A method for detecting miRNA in a subject suspected of having melanoma, comprising:
   (a) isolating miRNAs from extracellular melanoma-derived microvesicles contained in a sample from the subject suspected of having melanoma; and
   (b) detecting miRNAs consisting of let-7i, let-7a, hsa-miR-23a, hsa-miR-191, hsa-miR-1228, and HSA-miR-1825 in the sample comprising capturing the microRNAs with polynucleotide probes that each selectively bind each of the microRNAs, yielding an expression profile of the miRNAs.

2. The method of claim 1, and further comprising administering treatment for stage I melanoma to the subject.

3. The method of claim 2, and further comprising contacting the two or more miRNAs from the extracellular melanoma-derived microvesicles with two oligonucleotide primers that hybridize to each of the two or more miRNAs in a polymerase chain reaction.

4. The method of claim 1, wherein the extracellular melanoma-derived microvesicles are isolated in the sample from the subject by a method comprising a combination of ultrafiltration and ultracentrifugation.

* * * * *